(12) United States Patent
Goshorn et al.

(10) Patent No.: US 7,144,991 B2
(45) Date of Patent: Dec. 5, 2006

(54) STREPTAVIDIN EXPRESSED GENE FUSIONS AND METHODS OF USE THEREOF

(75) Inventors: Stephen Charles Goshorn, Shoreline, WA (US); Scott Stoll Graves, Monroe, WA (US); Joanne Elaine Schultz, Seattle, WA (US); Yukang Lin, Kenmore, WA (US); James Allen Sanderson, Seattle, WA (US); John M. Reno, Brier, WA (US)

(73) Assignee: Aletheon Pharmaceuticals, Inc., Seattle, WA (US)

( * ) Notice: Subject to any disclaimer, the term of this patent is extended or adjusted under 35 U.S.C. 154(b) by 0 days.

(21) Appl. No.: 10/013,173

(22) Filed: Dec. 7, 2001

(65) Prior Publication Data
US 2003/0095977 A1 May 22, 2003

Related U.S. Application Data

(63) Continuation-in-part of application No. 09/589,870, filed on Jun. 5, 2000, now abandoned.

(60) Provisional application No. 60/168,976, filed on Dec. 3, 1999, provisional application No. 60/137,900, filed on Jun. 7, 1999.

(51) Int. Cl.
C07K 16/46 (2006.01)
(52) U.S. Cl. ................ 530/391.7; 530/350; 530/387.3; 530/387.7; 530/388.8; 536/23.4
(58) Field of Classification Search ................ 530/350, 530/387.3, 387.7, 391.7, 388.8; 536/23.4
See application file for complete search history.

(56) References Cited

U.S. PATENT DOCUMENTS

| | | | |
|---|---|---|---|
| 4,839,293 A | 6/1989 | Cantor et al. | ................ 435/320 |
| 4,867,973 A | 9/1989 | Goers et al. | ............. 424/85.91 |
| 4,975,369 A | 12/1990 | Beavers et al. | ............ 435/69.1 |
| 5,169,939 A | 12/1992 | Gefter et al. | ............. 530/387.3 |
| 5,272,254 A | 12/1993 | Meade et al. | ................ 530/350 |
| 5,328,985 A | 7/1994 | Sano et al. | .................. 530/350 |
| 5,334,532 A | 8/1994 | Tackney et al. | ........ 435/252.33 |
| 5,395,609 A | 3/1995 | Stuttle | ....................... 424/1.69 |
| 5,530,101 A | 6/1996 | Queen et al. | ............ 530/387.3 |
| 5,630,996 A | 5/1997 | Reno et al. | ................. 424/1.49 |
| 5,696,237 A | 12/1997 | FitzGerald et al. | ...... 530/387.3 |
| 5,837,816 A | 11/1998 | Ciardelli et al. | ............ 530/350 |
| 5,863,745 A | 1/1999 | Fitzgerald et al. | ......... 435/7.21 |
| 6,156,321 A | 12/2000 | Thorpe et al. | ........... 424/198.1 |
| 6,204,023 B1 | 3/2001 | Robinson et al. | .......... 435/71.3 |
| 6,451,995 B1 * | 9/2002 | Cheung et al. | .......... 536/23.53 |

FOREIGN PATENT DOCUMENTS

| | | |
|---|---|---|
| EP | 682 040 A1 | 11/1995 |
| EP | 496 074 B1 | 11/1996 |
| WO | WO 86/02077 | 4/1986 |
| WO | WO 87/05026 | 8/1987 |
| WO | WO 93/24631 | 12/1993 |
| WO | WO 95/15770 | 6/1995 |
| WO | WO 95/25167 | 9/1995 |
| WO | WO 97/18314 | 5/1997 |
| WO | WO 97/19957 | 6/1997 |
| WO | WO 97/34634 | 9/1997 |
| WO | WO 98/50432 | 11/1998 |

OTHER PUBLICATIONS

Critchfield GC. Disease Markers. 1999; 15: 108-11.*
Tockman MS, et al. Cancer Res. 1992; 52 (Suppl.): 2711s-2718s.*
Ward AM. Developmental Oncol. 1985; 21: 90-106.*
Skolnick J, et al. Trends Biotechnol 2000 Jan; 18 (1): 34-9.*
Rudikoff S, et al. Proc Natl Acad Sci USA. Mar. 1982; 79; 1979-83.*
Sidransky D. Science. Nov. 7, 1997; 278 (5340): 1054-9.*
Kashmiri SV, et al. Hybridoma. Oct. 1995; 14 (5): 461-73.*
Sharkey RM, et al. Bioconj Chem. Jul.-Aug. 1997; 8 (4): 595-604.*
Epivatanos A, et al. Oral Dis. Mar. 2000; 6 (2): 112-7.*
Karacay H, et al. Bioconjug Chem. Jul.-Aug. 1997; 8 (4): 585-94.*
Bowie et al., "Deciphering the message in protein sequences: tolerance to amino acid substitutions," *Science* 247(4948):1306-1310, Mar. 16, 1990.
Burgess et al., "Possible dissociation of the heparin-binding and mitogenic activities of heparin-binding (acidic fibroblast) growth factor-1 from its receptor-binding activities by site-directed mutagenesis of a single lysine residue," *J. Cell Biol.* 111:2129-2138, Nov. 1990.
Lazar et al., "Transforming growth factor alpha: mutation of aspartic acid 47 and leucine 48 results in different biological activities," *Mol. Cell Biol.* 8(3):1247-1252, Mar. 1988.
Alfthan et al., "Properties of a Single-Chain Antibody Containing Different Linker Peptides," *Protein Eng*, 8(7):725-731, 1995.

(Continued)

*Primary Examiner*—Stephen L. Rawlings
(74) *Attorney, Agent, or Firm*—Seed IP Law Group PLLC

(57) ABSTRACT

The present invention provides vectors for expressing genomic streptavidin fusion cassettes. In the various embodiments, fusion proteins produced from these vectors are provided. In particular embodiments, fusion proteins comprising a single chain antibody and genomic streptavidin are provided as are vectors encoding the same. Also provided, are methods of using the fusion proteins of the present invention, and in particular, the use of scFvSA fusion proteins as diagnostic markers or as a cell specific targeting agents.

1 Claim, 25 Drawing Sheets

OTHER PUBLICATIONS

Anderson et al., "A Primatized Mab to human CD4 causes receptor modulation, without marked reduction in CD4+ T cells in chimpanzees," *Clinical Immunology and Immunopathology* 84: 73-84, 1997.

Argaraña et al., "Molecular Cloning and Nucleotide Sequence of the Streptavidin Gene," *Nucl. Acids Res.* 14(4):1871-1882, 1986.

Axworthy et al., "Antibody pretargeting for radioimmunotherapy: a three-step approach in tumored nude mice," *J. Nucl. Med.* 33 (5 SUPPL.): 880, 1992.

Axworthy et al., "Cure of human carcinoma xenografts by a single dose of pretargeted yttrium-90 with negligle toxicity," *Proc. Natl. Acad. Sci. USA* 97: 1802-1807, 2000.

Better, "T-Cell-Targeted Immunofusion Proteins From *E. Coli*," *Annals N. Y. Acad. Sci.* 782:544-54, 1996.

Bird et al., "Single-Chain Antigen-Binding Proteins," *Science* 242:423-426, 1988.

Bodey et al., "Failure of cancer vaccines: the significant limitations of this approach to immunotherapy," *Anticancer Research* 20(4) : 2665-2676, Jul./Aug. 2000.

Boleti et al., "Construction, Expression and Characterization of a Single-Chain Anti-Tumour Antibody (scFv)-IL-2 Fusion Protein," *Annals Oncol.* 6:945-947, 1995.

Buchegger et al., "Radiolabeled Chimeric Anit-CEA Monoclonal Antibody Compared with the original Mouse Monoclonal Antibody for Surgically Treated Colorectal Carcinoma," *The Journal of Nuclear Medicine* 36(3):420-429, 1995.

Chilkoti et al., "Engineered chimeric streptavidin tetramers as novel tools for bioseparations and drug delivery," *Bio/Technology* 13: 1198-1204, 1995.

Curti, B.D., "Physical barriers to drug delivery tumors," *Critical Reviews in Hematology/Oncology* 14: 29-39, 1993.

Darveau et al., "Expression of Antibody Fragments in *Escherichia coli*," *J. Clin. Immunoassay* 15(1):25-29, 1992.

DeNardo et al., "Strategies for developing effective radioimmunotherapy for solid tumors," *Clinical Cancer Research* 5: 3219s-3223s, 1999.

Desplancq et al., "Multimerization Behaviour of Single Chain Fv Variants for the Tumour-Binding Antibody B72.3," *Protein Eng.* 7(8):1027-1033, 1994.

Dübel et al., "Bifunctional and Multimeric Complexes of Streptavidin Fused to Single-Chain Antibodies (scFv)," *J. Immunol. Meth.* 178:201-209, 1995.

Fell et al., "Genetic Construction and Characterization of a Fusion Protein Consisting of a Chimeric F(ab') with Specificity for Carcinomas and Human IL-2," *The Journal of Immunology* 146(7):2446-2452, 1991.

Filpula et al., "Engineering of Immunoglobulin Fc and Single-Chain Fv Proteins in *Escherichia coli*," Antibody Expression and Engineering, ACS Symposium Series No. 604, Chap. 6, pp. 71-82, American Chemical Society: Washington, D.C., 1995.

Gallizia et al., "Production of a Soluble and Functional Recombinant Streptavidin in *Escherichia coli*," *Protein Expr. Purif.* 14:192-196, 1998.

Goodwin and Hnatowich, "Tumor Imaging with Indium-Labeled Biotin. Letter to the Editor and Reply," *The Journal of Nuclear Medicine* 32(4):750-751, 1991.

Goodwin et al., "Pharmacokinetics of Biotin-Chelate Conjugates for Pretargeted Avidin-Biotin Immunoscintigraphy," *The Journal of Nuclear Medicine* 33(Suppl. 5):p. 880, Abstract No. 232, 1992.

Goshorn et al., "Genetic Construction, Expression, and Characterization of a Single-Chain Anti-Carcinoma Antibody Fused to β-Lactamase," *Cancer Res.* 53:2123-2127, 1993.

Gura, T., "Systems for identifying drugs are often faulty," *Science* 278: 1041-1042, 1997.

Hand et al., "Comparitive Biological Properties of a Recombinant Chimeric Anti-Carcinoma mAb and a Recombinant Aglycosylated Variant," *Cancer Immunology Immunotherapy* 35:165-174, 1992.

Hnatawich et al., "Investigations of avidin and biotin for imaging applications," *Journal of Nuclear Medicine* 28: 1294-1302, 1987.

Huston et al., "Antigen Recognition and Targeted Delivery by the Single-Chain Fv," *Cell Biophys.* 22:189-224, 1993.

Huston et al., "Protein Engineering of Antibody Binding Sites: Recovery of Specific Activity in an Anti-Digoxin Single-Chain Fv Analogue Produced in *Escherichia coli*," *Proc. Natl. Acad. Sci.* 85:5879-5883, 1988.

Huston et al., "Protein Engineering of Single-Chain Fv Analogs and Fusion Proteins," *meth. Enzymol.*203:46-89, 1991.

Jain, R.K., "Barriers to drug delivery in solid tumors," *Scientific American* 271: 58-65, 1994.

Kalofonos et al., "Imaging of Tumor in Patients with Indium-111-Labeled Biotin and Streptavidin-Conjugated Antibodies: Preliminary Communication," *J. Nucl. Med.* 31:1791-1796, 1990.

Karp et al., "Identification of Biotinylated Molecules Using a Baculovirus-Expressed Luciferase-Streptavidin Fusion Protein," *Biotechniques* 20:452-459, 1996.

Kerschbaurner et al., "Single-Chain Fv Fusion Proteins Suitable as Coating and Detecting Reagents ina Double Antibody Sandwich Enzyme-Linked Immunosorbent Assay," *Analyt. Biochem.* 249:219-227, 1997.

Kipriyanov et al., "Single-Chain Antibody Streptavidin Fusions: Tetrameric Bifunctional scFv- Complexes with Biotin Activity and Enhanced Affinity to Antigen," *Hum. Antibody Hybridomas* 6(3):93-101, 1995.

Kipriyanov, et al., "Affinity Enhancement of a Recombinant Antibody: Formation of Complexes with Multiple Valency by a Single-Chain Fv Fragment—Core Streptavidin Fusion,"*J Protein Eng.* 9(2):203-211, 1996.

Kobayashi et al., "Improved Clearance of Radiolabeled Biotinylated Monoclonal Antibody Following the Infusion of Avidin as a 'Chase' Without Decreased Accumulation in the Target Tumor," *J. Nucl. Med.* 35:1677-1684, 1994.

Koch and Macke, "$^{99m}$-Tc Labeled biotin conjugates in a Tumor 'Pretargeting' Approach with Monoclonal Antibodies," *Angew. Chem. Int. Ed. Engl.* 31(11): 1507-1509, 1992.

Koo et al., "Construction and Expression of a Bifunctional Single-Chain Antibody Against *Bacillus cereus* Spores," *Appl. Environ. Microbiol.* 64(7):2490-2496, 1998.

Koo et al., "Development of a Streptavidin-Conjugated Single-Chain Antibody That Binds *Bacillus cereus* Spores," *Appl. Environ. Microbiol.* 64(7):2497-2502, 1998.

Kortt et al., "Single-Chain Fv fragments of Anti-Neurminidase Antibody NC10 Containing Five- and Ten-Residue Linkers Form Dimers and with Zero-Residue Linker a Trimer," *Protein Eng.* 10(4):423-433, 1997.

Le et al., "A Streptavidin-Cellulose-Binding Domain Fusion Protein that Binds Biotinylated Proteins to Cellulose," *Enzyme Microb. Technol.* 16:496-500, 1994.

Li et al., "Genetically Engineered Brain Drug Delivery Vectors: Cloning, Expression and *in vivo* Application of an Anti-transferrin Receptor Single Chain Antibody —Streptavidin Fusion Gene and Protein," *Protein Eng.*12(9):787-796, 1999.

Lin et al., "A Single Chain Antibody-Streptavidin Fusion Protein for Pretargeted Lymphoma Therapy," Abstract, Antibody Engineering, 10th Anniversary Meeting, Dec. 6-9, 1999, La Jolla, CA.

McCloskey et al., "Human Constant Regions Influence the Antibody-Binding Characteristics of Mouse-Human Chimeric IgG Subclass," *Immunology* 88:169-173, 1996.

McLaughlin et al., "Clinical status and optimal use of Rituximab for B-cell lymphomas," *Oncology* 12: 1763-1769, 1998.

Morrison, "Genetically Engineered (Chimeric) Antibodies," *Hospital Pratice*:65-80, Oct. 15, 1989.

Ohno and Meruelo, "Multi-Drug Delivery System Using Streptavidin-Transforming Growth Factor-α Chimeric Protein," *DNA Cell Bio.*, 15(5):401-406, 1996.

Ohno et al., "Cell-Specific, Multidrug Delivery System Using Streptavidin-Protein A Fusion Protein," *Biochem. Molec. Med.* 58:227-233, 1996.

Paganelli et al., "Intraperitoneal Radio-Localization of Tumors Pre-Targeted by Biotinylated Monoclonal Antiodies," *Int. J. Cancer* 45: 1184-1189, 1990.

Paganelli et al., "Monoclonal Antibody Pretargeting Techniques for Tumour Localization: The Avidin-Biotin," *Nuclear Medicine Communications* 12:211-234, 1991.

Paganelli et al., "Pilot Therapy Trial of CEA Positive Tumours Using a Three-Step Pretargeting Approach," *Tumor Targeting* 3:96-104, 1998.

Paganelli et al., "Two-Step Tumour Targetting in Ovarian Cancer Patients Using Biotinylated Monoclonal Antibodies and Radioactive Streptavidin," *European Journal of Nuclear Medicine* 19:322-329, 1992.

Pahler et al., "Characterization and crystallization of core streptavidin," *Journal of Biological Chemistry* 262: 13933-13937, 1987.

Pearce et al., "Linear Gene Fusions of Antibody Fragments with Streptavidin can be Linked to Biotin Labelled Secondary Molecules to Form Bispecific Reagents," *Biochem. Molec. Biol. Intl.* 42(6):1179-1188, 1997.

Plückthun, "Antibodies from *Escherichia coli*," *Nature* 347:497-498, 1990.

Plückthun, "Antibody Engineering: Advances from the Use of *Escherichia coli* Expression Systems," *Biotechnol.* 9:545-551, 1991.

Plückthun and Pack, "New Protein Engineering Approaches to Multivalent and Bispecific Antibody Fragments," *Immunotechnology* 3:83-105, 1997.

Press et al., "Treatment of Refractory Non-Hodgkin's Lymphoma With Radiolabeled MB-1 (Anti-CD37) Antibody," *Journal of Clinical Oncology* 7(8):1027-1038, 1989.

Presta et al., "Humanization of an Antibody Directed Against IgE," *The Journal of Immunology* 151(5):2623-2632, 1993.

Raag and Whitlow, "Single-chain Fvs," *FASEB Journal* 9:73-80, 1995.

Railo et al., "The prognostic value of insulin-like growth factor-1 in breast cancer patients, results of a follow-up study of 126 patients," *European Journal of Cancer* 30A: 307-311, 1994.

Sano and Cantor "Expression Vectors for Streptavidin-Containing Chimeric Proteins," *Biochem. Biophys. Res. Commun.* 176(2):571-577, 1991.

Sano and Cantor, "A Streptavidin-Protein A Chimera that Allows One-Step Production of a Variety of Specific Antibody Conjugates," *Biotechnol.* 9:1378-1381, 1991.

Sano and Cantor, "Expression of a Cloned Streptavidin Gene in *Escherichia coli*," *Proc. Natl. Acad. Sci.* 87:142-146, 1990.

Sano et al., "A Streptavidin Mutant Containing a Cysteine Stretch That Facilitates Production of a Variety of Specific Streptavidin Conjugates," *Bio/Technology* 11:201-206, 1993.

Sano et al., "A Streptavidin-Metallothionein Chimera that Allows Specific Labeling of Biological Materials with many Different Heavy Metal Ions," *Proc. Natl. Acad. Sci.* 89:1534-1538, 1992.

Sano et al., "Genetic Engineering of Streptavidin, a Versatile Affinity Tag," *J. Chromatogr. B* 715:85-91, 1998.

Sano et al., "Molecular Engineering of Streptavidin," *Ann. N.Y. Acad. Sci.* 799:383-390, 1996.

Sawyer and Blattner, "Rapid Detection of Antigen Binding by Antibody Fragments Expressed in the Periplasm of *Escherichia coli*," *Protein Eng.* 4(8):947-953, 1991.

Sawyer et al., "The Effects of Induction Conditions on Production of a Soluble Anti-Tumor sFv in *Escherichia coli*," *Protein Eng.* 7(11):1401-1406, 1994.

Schultz et al., "A tetravalent single-chain antibody-streptavidin fusion protein for pretargeted lymphoma therapy," *Cancer Research* 60: 6663-6669, 2000.

Shan et al., "Characterization of scFv-Ig Constructs Generated from the Anti-CD20 mAb 1F5 Using Linker Peptides of Varying Lengths," *J. Immunol.* 162(11):6589-6595, 1999.

Shin et al., "Functional and Pharmacokinetic Properties of Antibody-Avidin Fusion Proteins," *J. Immunol.* 158(10):4797-4804, 1997.

Skerra et al., "The Functional Expression of Antibody Fv Fragments in *Escherichia coli*: Improved Vectors and a Generally Applicable Purification Technique," *Biotechnol.* 9(3):273-8, 1991.

Spooner et al., "Expression of Immunoglobulin Heavy Chain-Ricin a Chain Fusions in Mammalian Cells," *Molecular Immunology* 31(2):117-125, 1994.

Spooner et al., "Genetically Engineered Antibodies for Diagnostic Pathology," *Hum. Pathol* 25:606-614, 1994.

Stickney et al., "Bifunctional Antibody: A Binary Radiopharmaceutical Delivery System for Imaging Colorectal Carcinoma," *Cancer Research* 51:6650-6655, 1991.

Tang et al., "Selection of linkers for a catalytic single-chain antibody using phage display technology," *Journal of Biological Chemistry* 271: 15682-15686, 1996.

Thompson and Weber, "Construction and Expression of a Synthetic Streptavidin-Encoding Gene in *Escherichia coli*," *Gene* 136:243-246, 1993.

Trang et al., "Pharmacokinetics of a Mouse/Human Chimeric Monoclonal Antibody (C-17-1A) in Metastatic Adenocarcinoma Patients," *Pharmaceutical Research* 7(6):587-592, 1990.

Turner et al., "Importance of the Linker in Expression of Single-Chain Fv Antibody Fragments: Optimisation of Peptide Sequence Using Phage Display Technology," *J. Immunol. Meth.* 205:43-54, 1997.

Vitetta et al., "Monoclonal antibodies as agonists: an expanded role for their use in cancer therapy," *Cancer Research* 54: 5301-5309, 1994.

Walsh et al., "An *Escherichia coli* Plasmid Vector System for Production of Streptavidin Fusion Proteins: Expression and Bioselective Adsorption of Streptavidin-β-Galactosidase," *Biotechnol. Bioeng.* 44:1348-1354, 1994.

Weiden et al., "Rhenium-186-Labeled Chimeric Antibody NR-LU-13: Pharmacokinetics, Biodistribution and Immunogenecity Relative to Murine Analog NR-LU-10," *J. Nucl. Med.* 34:2111-2119, 1993.

Whitlow and Filpula, "Single-Chain Fv Proteins and Their Fusion Proteins," *Methods: A Companion to Methods in Enzymology* 2(2):97-105, 1991.

Whitlow et al., "An Improved Linker for Single-Chain Fv with Reduced Aggregation and Enhanced Proteolytic Stability," *Protein Eng.* 6(8):989-995, 1993.

Whitlow et al., "Multivalent Fvs: Characterization of Single-Chain Fc Oligomers and Preparation of a Bispecific Fv," *Protein Eng.* 7(8):1017-1026, 1994.

Wilcher and Bayer, "Indtroduction to Avidin-Biotin Technology," *Meth. Enzymol.* 184:5-13, 1990.

Dillman, R.O., "Monoclonal Antibody Therapy for Lymphoma," *Cancer Practice* 9(2): 71-80, Mar./Apr. 2001.

Schultz, J. et al., "A Tetravalent Single-chain Antibody-Streptavidin Fusion Protein for Pretargeted Lymphoma Therapy," *Cancer Research* 60: 6663-6669, Dec. 1, 200.

Zhang, M. et al., "Pretargeting radioimmunotherapy of a murine model of adult T-cell leukemia with the α-emitting radionuclide, bismuth 213," *Blood* 100(1): 208-216, Jul. 1, 2002.

Zhang, M. et al., "Pretarget radiotherapy with an anti-CD25 antibody-streptavidin fusion protein was effective in therapy of leukemia/lymphoma xenografts," *Proc. Natl. Acad. Sci.* 100(4): 1891-1895, Feb. 18, 2003.

\* cited by examiner

5'  CCCTCCGTCCCCGCCGGGCAACAACTAGGGAGTATTTTTCGTGTCTCAC

```
                              -20                        -10
               Met Arg Lys Ile Val Val Ala Ala Ile Ala Val Ser Leu Thr Thr
Signal         ATG CGC AAG ATC GTC GTT GCA GCC ATC GCC GTT TCC CTG ACC ACG
sequence           Mst I                          1
               Val Ser Ile Thr Ala Ser Ala Ser Ala Asp Pro Ser Lys Asp Ser
               GTC TCG ATT ACG GCC AGC GCT TCG GCA GAC CCC TCC AAG GAC TCG
                               10                        20
               Lys Ala Gln Val Ser Ala Ala Glu Ala Gly Ile Thr Gly Thr Trp
               AAG GCC CAG GTC TCG GCC GCC GAG GCC GGC ATC ACC GGC ACC TGG
                                        30
               Tyr Asn Gln Leu Gly Ser Thr Phe Ile Val Thr Ala Gly Ala Asp
               TAC AAC CAG CTC GGC TCG ACC TTC ATC GTG ACC GCG GGC GCC GAC
                               40                        50
               Gly Ala Leu Thr Gly Thr Tyr Glu Ser Ala Val Gly Asn Ala Glu
               GGC GCC CTG ACC GGA ACC TAC GAG TCG GCC GTC GGC AAC GCC GAG
                                        60
               Ser Arg Tyr Val Leu Thr Gly Arg Tyr Asp Ser Ala Pro Ala Thr
               AGC CGC TAC GTC CTG ACC GGT CGT TAC GAC AGC GCC CCG GCC ACC
                               70                        80
               Asp Gly Ser Gly Thr Ala Leu Gly Trp Thr Val Ala Trp Lys Asn
               GAC GGC AGC GGC ACC GCC CTC GGT TGG ACG GTG GCC TGG AAG AAT
                                        90
               Asn Tyr Arg Asn Ala His Ser Ala Thr Thr Trp Ser Gly Gln Tyr
               AAC TAC CGC AAC GCC CAC TCC GCG ACC ACG TGG AGC GGC CAG TAC
                               100                       110
               Val Gly Gly Ala Glu Ala Arg Ile Asn Thr Gln Trp Leu Leu Thr
               GTC GGC GGC GCC GAG GCG AGG ATC AAC ACC CAG TGG CTG CTG ACC
                                        120
               Ser Gly Thr Thr Glu Ala Asn Ala Trp Lys Ser Thr Leu Val Gly
               TCC GGC ACC ACC GAG GCC AAC GCC TGG AAG TCC ACG CTG GTC GGC
                               130                       140
               His Asp Thr Phe Thr Lys Val Lys Pro Ser Ala Ala Ser Ile Asp
               CAC GAC ACC TTC ACC AAG GTG AAG CCG TCC GCC GCC TCC ATC GAC
                                        150
               Ala Ala Lys Lys Ala Gly Val Asn Asn Gly Asn Pro Leu Asp Ala
               GCG GCG AAG AAG GCC GGC GTC AAC AAC GGC AAC CCG CTC GAC GCC
                                             Hind II
               Val Gln Gln Stop
               GTT CAG CAG TAG TCGCGTCCCGGCACCGGCGGGTGCCGGGACCTCGGCC  3'
```

*Fig. 4* pEX94B EcoRI-BamHI fragment

```
GAATTCACGA AGTAACCGAC AGGACTCGGC CATTCTTTGG CCGAAATTCC TTTGCAGAAA  ⎫
                                                                    ⎪
ATGTTGTTGA GAACCCTCCG ATGGCTAGTA CGATTTACAC CGAACATGTG CCCTTGGCAA  ⎪
                                                                    ⎪  Streptavidin
CCATCGACCC GGACCTCGAC CATCCAGTTC TGCCGCCAAA GACACATGCC GCACTGCTGT  ⎬  regulatory
                                                                    ⎪  region
TTGTTCACCG ACACCGTCAG GTGCACGGCC GAGGTCACAA ACCTTGACGG GCGGGATACG  ⎪
                                                                    ⎪
GACGGCGCAC GCCACAGCGC GCCCTCCGTC CCCCGCCGGG CAACAACTAG GGGAGTATTTTT⎭

CGTGTCTCAC ATGCGCAAGA TCGTCGTTGC AGCCATCGCC GTTTCCCTGA CCACGGTCTC  ⎫ Streptavidin
          M  R  K  I  V  V  A  A  I  A  V  S  L  T  T  V  S       ⎬ signal sequence
                                                                    ⎭
```

```
GATTACGGCC ATGGCTGACA TCCAGATGAC TCAGTCTCCA TCGTCCTTGT CTGCCTCTGT  ⎫
 I  T  A  M  A│D  I  Q  M  T  Q  S  P  S  S  L  S  A  S  V         ⎪
              signal peptidase                                      ⎪
GGGAGACAGA GTCACGATCA CTTGTCGGGC TAGTCAGGGC ATTAGAGGTA ATTTAGACTG  ⎪
 G  D  R  V  T  I  T  C  R  A  S  Q  G  I  R  G  N  L  D  W        ⎪
                                                                    ⎪
GTATCAGCAG AAACCTGGTA AGGGACCGAA ACTCCTAATC TACTCCACAT CCAATTTAAA  ⎪
 Y  Q  Q  K  P  G  K  G  P  K  L  L  I  Y  S  T  S  N  L  N        ⎬ V_L
                                                                    ⎪
TTCTGGTGTC CCATCAAGGT TCAGTGGCAG TGGGTCTGGG TCAGATTATA CTCTCACCAT  ⎪
 S  G  V  P  S  R  F  S  G  S  G  S  G  S  D  Y  T  L  T  I        ⎪
                                                                    ⎪
CAGCAGCCTT CAGCCTGAAG ATTTCGCAAC GTATTACTGT CTACAGCGTA ATGCGTATCC  ⎪
 S  S  L  Q  P  E  D  F  A  T  Y  Y  C  L  Q  R  N  A  Y  P        ⎭

GTACACGTTC GGACAAGGGA CCAAGCTGGA GATCAAGATC TCTGGTGGCG GTGGCTCGGG
 Y  T  F  G  Q  G  T  K  L  E  I  K  I  S  G  G  G  G  S  G
                                   ├───────────────────────────
───────linker──────────┤
CGGTGGTGGG TCGGGTGGCG GAGGCTCGAG CCAGGTTCAG CTGGTCCAGT CTGGGGCAGA  ⎫
 G  G  G  S  G  G  G  S  S  Q  V  Q  L  V  Q  S  G  A  E          ⎪
                                                                    ⎪
GGTGAAAAAG CCAGGGGCCT CAGTCAAGGT GTCCTGCAAG GCTTCTGGCT TCAACATTAA  ⎪
 V  K  K  P  G  A  S  V  K  V  S  C  K  A  S  G  F  N  I  K        ⎪
                                                                    ⎬ V_H
AGACACCTAT ATGCACTGGG TGAGGCAGGC ACCTGGACAG GGCCTGCAGT GGATGGGAAG  ⎪
 D  T  Y  M  H  W  V  R  Q  A  P  G  Q  G  L  Q  W  M  G  R        ⎪
                                                                    ⎪
GATTGATCCT GCGAATGGTA ATACTAAATC CGACCTGTCC TTCCAGGGCA GGGTGACTAT  ⎪
 I  D  P  A  N  G  N  T  K  S  D  L  S  F  Q  G  R  V  T  I        ⎭
```

*Fig. 10A*

```
AACAGCAGAC ACGTCCATCA ACACAGCCTA CATGGAACTC AGCAGCCTGA GGTCTGACGA
  T  A  D   T  S  I    N  T  A  Y  M  E  L    S  S  L    R  S  D  D

CACTGCCGTC TATTACTGTT CTAGAGAGGT CCTAACTGGG ACGTGGTCTT TGGACTACTG
  T  A  V   Y  Y  C   S  R  E  V   L  T  G   T  W  S    L  D  Y  W
                                        ├——linker——┤
GGGTCAAGGA ACCTTAGTCA CCGTGAGCTC TGGCTCTGGT TCGGCAGACC CCTCCAAGGA
 G  Q  G   T  L  V   T  V  S  S │ G  S  G   S  A  D    P  S  K  D
                              10 11
                          ┌——core——→
CTCGAAGGCC CAGGTCTCGG CCGCCGAGGC CGGCATCACC GGCACCTGGT ACAACCAGCT
  S  K  A   Q  V  S   A  A │ E  A   G  I  T   G  T  W    Y  N  Q  L CGGCTCGACC TTCATCGTGA CCGCGGGCGC CGACGGCGCC CTGACCGGAA CCTACGAGTC
  G  S  T   F  I  V   T  A  G  A   D  G  A    L  T  G   T  Y  E  S GGCCGTCGGC AACGCCGAGA GCCGCTACGT CCTGACCGGT CGTTACGACA GCGCCCCGGC
  A  V  G   N  A  E   S  R  Y  V   L  T  G   R  Y  D    S  A  P  A CACCGACGGC AGCGGCACCG CCCTCGGTTG GACGGTGGCC TGGAAGAATA ACTACCGCAA
  T  D  G   S  G  T   A  L  G  W   T  V  A    W  K  N   N  Y  R  N CGCCCACTCC GCGACCACGT GGAGCGGCCA GTACGTCGGC GGCGCCGAGG CGAGGATCAA
  A  H  S   A  T  T   W  S  G  Q    Y  V  G   G  A  E    A  R  I  N CACCCAGTGG CTGCTGACCT CCGGCACCAC CGAGGCCAAC GCCTGGAAGT CCACGCTGGT
  T  Q  W   L  L  T   S  G  T  T   E  A  N   A  W  K    S  T  L  V
                    ┌——core——┐
CGGCCACGAC ACCTTCACCA AGGTGAAGCC GTCCGCCGCC TCCATCGACG CGGCGAAGAA
  G  H  D   T  F  T    K  V  K  P   S  A  A    S  I  D   A  A  K  K GGCCGGCGTC AACAACGGCA ACCCGCTCGA CGCCGTTCAG CAGTAAGGAT CC
  A  G  V   N  N  G   N  P  L  D   A  V  Q  Q  *
```

} Streptavidin 1-159

*Fig. 10B*

GACATCGTGC TGTCGCAGTC TCCAGCAATC CTGTCTGCAT CTCCAGGGGA GAA
GGTCACAATG ACTTGCAGGG CCAGCTCAAG TGTAAGTTAC ATGCACTGGT ACCAGCAGAA
GCCAGGATCC TCCCCCAAAC CCTGGATTTA TGCCACATCC AACCTGGCTT CTGGAGTCCC
TGCTCGCTTC AGTGGCAGTG GGTCTGGGAC CTCTTACTCT CTCACAATCA GCAGAGTGGA
GGCTGAAGAT GCTGCCACTT ATTACTGCCA GCAGTGGATT AGTAACCCAC CCACGTTCGG
TGCTGGGACC AAGCTGGAGC TGAAGATCTC TGGTCTGGAA GGCAGCCCGG AAGCAGGTCT
GTCTCCGGAC GCAGGTTCCG GCTCAGCCA GGTTCAGCTG GTCCAGTCAG GGGCTGAGCT
GGTGAAGCCT GGGGCCTCAG TGAAGATGTC CTGCAAGGCT TCTGGCTACA CATTTACCAG
TTACAATATG CACTGGGTAA AGCAGACACC TGGACAGGGC CTGGAATGGA TTGGAGCTAT
TTATCCAGGA AATGGTGATA CTTCCTACAA TCAGAAGTTC AAAGGCAAGG CCACATTGAC
TGCAGACAAA TCCTCCAGCA CAGCCTACAT GCAGCTCAGC AGCCTGACAT CTGAGGACTC
TGCGGTCTAT TACTGTGCAA GAGCGCAATT ACGACCTAAC TACTGGTACT TCGATGTCTG
GGGCGCAGGG ACCACGGTCA CCGTGAGCTC TGGCTCTGGT TCGGCAGACC CCTCCAAGGA
CTCGAAGGCC CAGGTCTCGG CCGCCGAGGC CGGCATCACC GGCACCTGGT ACAACCAGCT
CGGCTCGACC TTCATCGTGA CCGCGGGCGC CGACGGCGCC CTGACCGGAA CCTACGAGTC
GGCCGTCGGC AACGCCGAGA GCCGCTACGT CCTGACCGGT CGTTACGACA GCGCCCCGGC
CACCGACGGC AGCGGCACCG CCCTCGGTTG GACGGTGGCC TGGAAGAATA ACTACCGCAA
CGCCCACTCC GCGACCACGT GGAGCGGCCA GTACGTCGGC GGCGCCGAGG CGAGGATCAA
CACCCAGTGG CTGCTGACCT CCGGCACCAC CGAGGCCAAC GCCTGGAAGT CCACGCTGGT
CGGCCACGAC ACCTTCACCA AGGTGAAGCC GTCCGCCGCC TCCATCGACG CGGCGAAGAA
GGCCGGCGTC AACAACGGCA ACCCGCTCGA CGCCGTTCAG CAGTAA

Fig. 11A

Translation of B9E9pKOD scFvSA

DIVLSQSPAIL SASPGEKVTM TCRASSSVSY MHWYQQKPGS SPKPWIYATS NLASGVPARF  V_L
SGSGSGTSYS LTISRVEAED AATYYCQQWI SNPPTFGAGT KLELKISGLE GSPEAGLSPD   pKOD
AGSGSSQVQL VQSGAELVKP GASVKMSCKA SGYTFTSYNM HWVKQTPGQG LEWIGAIYPG
NGDTSYNQKF KGKATLTADK SSSTAYMQLS SLTSEDSAVY YCARAQLRPN YWYFDVWGAG   V_H
TTVTVSSGSG SADPSKDSKA QVSAAEAGIT GTWYNQLGST FIVTAGADGA LTGTYESAVG   Linker2
NAESRYVLTG RYDSAPATDG SGTALGWTVA WKNNYRNAHS ATTWSGQYVG GAEARINTQW   SA
LLTSGTTEAN AWKSTLVGHD TFTKVKPSAA SIDAAKKAGV NNGNPLDAVQ Q*

Fig. 11B

E31-2-20 plasmid: NcoI-BamHf fragment containing B9E9 Vh-linker-Vl-Sa gene

```
    CCATGGCT|CAGGTTCAGCTGGTCCAGTCAGGGGCTGAGCTGGTGAAGCCTGGGGCCTCAG
     M  A  | Q  V  Q  L  V  Q  S  G  A  E  L  V  K  P  G  A  S  V

V_H  TGAAGATGTCCTGCAAGGCTTCTGGCTACACATTTACCAGTTACAATATGCACTGGGTAA
      K  M  S  C  K  A  S  G  Y  T  F  T  S  Y  N  M  H  W  V  K

AGCAGACACCTGGACAGGGCCTGGAATGGATTGGAGCTATTTATCCAGGAAATGGTGATA
      Q  T  P  G  Q  G  L  E  W  I  G  A  I  Y  P  G  N  G  D  T

CTTCCTACAATCAGAAGTTCAAAGGCAAGGCCACATTGACTGCAGACAAATCCTCCAGCA
      S  Y  N  Q  K  F  K  G  K  A  T  L  T  A  D  K  S  S  S  T

CAGCCTACATGCAGCTCAGCAGCCTGACATCTGAGGACTCTGCGGTCTATTACTGTGCAA
      A  Y  M  Q  L  S  S  L  T  S  E  D  S  A  V  Y  Y  C  A  R

GAGCGCAATTACGACCTAACTACTGGTACTTCGATGTCTGGGGCGCAGGGACCACGGTCA
      A  Q  L  R  P  N  Y  W  Y  F  D  V  W  G  A  G  T  T  V  T

CCGTGAGCAAGATCTCTGGT|GGCGGTGGCTCGGGCGGTGGTGGGTCGGGTGGCGGCGGCT
      V  S  K  I  S  G  | G  G  G  S  G  G  G  G  S  G  G  G  G  S
                       |——————————————— linker ——————————
     CGGGTGGTGGTGGGTCGGGCGGCGGCGGCTCG|AGCGACATCGTGCTGTCGCAGTCTCCAG
      G  G  G  S  G  G  G  G  S  | S  D  I  V  L  S  Q  S  P  A CAATCCTGTCTGCATCTCCAGGGGAGAAGGTCACAATGACTTGCAGGGCCAGCTCAAGTG
      I  L  S  A  S  P  G  E  K  V  T  M  T  C  R  A  S  S  S  V TAAGTTACATGCACTGGTACCAGCAGAAGCCAGGATCCTCCCCCAAACCCTGGATTTATG
      S  Y  M  H  W  Y  Q  Q  K  P  G  S  S  P  K  P  W  I  Y  A V_L  CCACATCCAACCTGGCTTCTGGAGTCCCTGCTCGCTTCAGTGGCAGTGGGTCTGGGACCT
       T  S  N  L  A  S  G  V  P  A  R  F  S  G  S  G  S  G  T  S
```

Fig. 11C

```
                    CTTACTCTCTCACAATCAGCAGAGTGGAGGCTGAAGATGCTGCCACTTATTACTGCCAGC
                     Y  S  L  T  I  S  R  V  E  A  E  D  A  A  T  Y  Y  C  Q  Q

AGTGGATTAGTAACCCACCCACGTTCGGTGCTGGGACCAAGCTGGAGCTGAAGAGCTCTG
                     W  I  S  N  P  P  T  F  G  A  G  T  K  L  E  L  K  S  S  G

GCTCTGGTTCGGCAGACCCCTCCAAGGACTCGAAGGCCCAGGTCTCGGCCGCCGAGGCCG
                      S  G  S  A  D  P  S  K  D  S  K  A  Q  V  S  A  A  E  A  G
                     ─linker─

GCATCACCGGCACCTGGTACAACCAGCTCGGCTCGACCTTCATCGTGACCGCGGGCGCCG
                     I  T  G  T  W  Y  N  Q  L  G  S  T  F  I  V  T  A  G  A  D

ACGGCGCCCTGACCGGAACCTACGAGTCGGCCGTCGGCAACGCCGAGAGCCGCTACGTCC
   Streptavidin      G  A  L  T  G  T  Y  E  S  A  V  G  N  A  E  S  R  Y  V  L TGACCGGTCGTTACGACAGCGCCCCGGCCACCGACGGCAGCGGCACCGCCCTCGGTTGGA
                     T  G  R  Y  D  S  A  P  A  T  D  G  S  G  T  A  L  G  W  T CGGTGGCCTGGAAGAATAACTACCGCAACGCCCACTCCGCGACCACGTGGAGCGGCCAGT
                     V  A  W  K  N  N  Y  R  N  A  H  S  A  T  T  W  S  G  Q  Y ACGTCGGCGGCGCCGAGGCGAGGATCAACACCCAGTGGCTGCTGACCTCCGGCACCACCG
                     V  G  G  A  E  A  R  I  N  T  Q  W  L  L  T  S  G  T  T  E AGGCCAACGCCTGGAAGTCCACGCTGGTCGGCCACGACACCTTCACCAAGGTGAAGCCGT
                     A  N  A  W  K  S  T  L  V  G  H  D  T  F  T  K  V  K  P  S CCGCCGCCTCCATCGACGCGGCGAAGAAGGCCGGCGTCAACAACGGCAACCCGCTCGACG
                     A  A  S  I  D  A  A  K  K  A  G  V  N  N  G  N  P  L  D  A

CCGTTCAGCAGTAAGGATCC
                     V  Q  Q  *  G  S
```

*Fig. 11D*

```
                                  signal peptidase
CACAGCGCGCCCTCCGTCCCCGCCGGGCAACAACTAGGGGAGTATTTTTCGTGTCTCAC
ATGCGCAAGATCGTCGTTGCAGCCATCGCCGTTTCCCTGACCACGGTCTCGATTACGGCC
 M   R   K   I   V   V   A   A   I   A   V   S   L   T   T   V   S   I   T   A
ATGGCTCAGGTTCAGTTGCAGCAGTCTGATGCTGAATTGGTGAAACCGGGTGCTTCAGTG
 M   A   Q   V   Q   L   Q   Q   S   D   A   E   L   V   K   P   G   A   S   V
AAAATTTCCTGCAAAGCTTCTGGCTACACCTTCACCGATCATGCAATTCATTGGGTGAAA
 K   I   S   C   K   A   S   G   Y   T   F   T   D   H   A   I   H   W   V   K
CAGAACCCGGAACAGGGCCTGGAATGGATTGGTTATTTCTCTCCGGGTAATGATGATTTC
 Q   N   P   E   Q   G   L   E   W   I   G   Y   F   S   P   G   N   D   D   F     V_H
AAATACAATGAACGTTTCAAAGGCAAAGCCACGCTGACCGCAGATAAATCCTCCAGCACC
 K   Y   N   E   R   F   K   G   K   A   T   L   T   A   D   K   S   S   S   T
GCCTACGTGCAGCTCAACAGCCTGACGTCTGAAGATTCTGCAGTGTATTTCTGTACGCGT
 A   Y   V   Q   L   N   S   L   T   S   E   D   S   A   V   Y   F   C   T   R
TCCCTGAATATGGCCTACTGGGGTCAAGGTACCTCAGTCACCGTCTCCAAGATCTCTGGT
 S   L   N   M   A   Y   W   G   Q   G   T   S   V   T   V   S   K   I   S   G
GGCGGTGGCTCGGGCGGTGGTGGGTCGGGTGGCGGCGGCTCGGGTGGTGGTGGGTCGGGC
 G   G   G   S   G   G   G   S   G   G   G   S   G   G   G   S
GGCGGCGGCTCGAGCGATATTGTGATGTCACAGTCTCCGTCCTCCCTACCGGTGTCAGTT
 G   G   G   S   D   I   V   M   S   Q   S   P   S   S   L   P   V   S   V
GGCGAAAAAGTTACCTTGAGCTGCAAATCCAGTCAGAGCCTTTTATATAGTGGTAATCAG
 G   E   K   V   T   L   S   C   K   S   S   Q   S   L   L   Y   S   G   N   Q
AAAAACTACTTGGCCTGGTACCAGCAGAAACCGGGTCAGTCTCCGAAACTGCTGATTTAC     V_L
 K   N   Y   L   A   W   Y   Q   Q   K   P   G   Q   S   P   K   L   L   I   Y
TGGGCATCCGCTCGTGAATCTGGGGTCCCGGATCGCTTCACCGGCAGTGGTTCTGGGACC
 W   A   S   A   R   E   S   G   V   P   D   R   F   T   G   S   G   S   G   T
GATTTCACCCTCTCCATCAGCAGTGTGAAAACCGAAGACCTGGCAGTTTATTACTGTCAG
 D   F   T   L   S   I   S   S   V   K   T   E   D   L   A   V   Y   Y   C   Q
CAGTATTATAGCTATCCGCTCACGTTCGGTGCTGGGACCAAACTGGTGCTGAAGAGCTCT
 Q   Y   Y   S   Y   P   L   T   F   G   A   G   T   K   L   V   L   K   S   S
GGCTCTGGTTCGGCAGACCCCTCCAAGGACTCGAAGGCCCAGGTCTCGGCCGCCGAGGCC
 G   S   G   S   A   D   P   S   K   D   S   K   A   Q   V   S   A   A   E   A
GGCATCACCGGCACCTGGTACAACCAGCTCGGCTCGACCTTCATCGTGACCGCGGGCGCC
 G   I   T   G   T   W   Y   N   Q   L   G   S   T   F   I   V   T   A   G   A
GACGGCGCCCTGACCGGAACCTACGAGTCGGCCGTCGGCAACGCCGAGAGCCGCTACGTC
 D   G   A   L   T   G   T   Y   E   S   A   V   G   N   A   E   S   R   Y   V
CTGACCGGTCGTTACGACAGCGCCCCGGCCACCGACGGCAGCGGCACCGCCCTCGGTTGG
 L   T   G   R   Y   D   S   A   P   A   T   D   G   S   G   T   A   L   G   W
ACGGTGGCCTGGAAGAATAACTACCGCAACGCCCACTCCGCGACCACGTGGAGCGGCCAG     SA
 T   V   A   W   K   N   N   Y   R   N   A   H   S   A   T   T   W   S   G   Q
TACGTCGGCGGCGCCGAGGCGAGGATCAACACCCAGTGGCTGCTGACCTCCGGCACCACC
 Y   V   G   G   A   E   A   R   I   N   T   Q   W   L   L   T   S   G   T   T
GAGGCCAACGCCTGGAAGTCCACGCTGGTCGGCCACGACACCTTCACCAAGGTGAAGCCG
 E   A   N   A   W   K   S   T   L   V   G   H   D   T   F   T   K   V   K   P
TCCGCCGCCTCCATCGACGCGGCGAAGAAGGCCGGCGTCAACAACGGCAACCCGCTCGAC
 S   A   A   S   I   D   A   A   K   K   A   G   V   N   N   G   N   P   L   D
GCCGTTCAGCAGTAAGGATCCGGCTGCTAACAAAGCCCGAAAGGAAGCTGAGTTGGCTGC
 A   V   Q   Q   *
TGCCACCGCTGAGCAATAACTAGCATA
```

*FIG. 22*

SEQUENCE LISTING

<160> NUMBER OF SEQ ID NOS: 69

<210> SEQ ID NO 1
<211> LENGTH: 638
<212> TYPE: DNA
<213> ORGANISM: Streptomyces avidinii

<400> SEQUENCE: 1

```
ccctccgtcc ccgccgggca acaactaggg agtatttttc gtgtctcaca tgcgcaagat      60
cgtcgttgca gccatcgccg tttccctgac cacggtctcg attacggcca gcgcttcggc     120
agacccctcc aaggactcga aggcccaggt ctcggccgcc gaggccggca tcaccggcac     180
ctggtacaac cagctcggct cgaccttcat cgtgaccgcg ggcgccgacg gcgccctgac     240
cggaacctac gagtcggccg tcggcaacgc cgagagccgc tacgtcctga ccggtcgtta     300
cgacagcgcc ccggccaccg acggcagcgg caccgccctc ggttggacgg tggcctggaa     360
gaataactac cgcaacgccc actccgcgac cacgtggagc ggccagtacg tcggcggcgc     420
cgaggcgagg atcaacaccc agtggctgct gacctccggc accaccgagg ccaacgcctg     480
gaagtccacg ctggtcggcc acgacacctt caccaaggtg aagccgtccg ccgcctccat     540
cgacgcggcg aagaaggccg gcgtcaacaa cggcaacccg ctcgacgccg ttcagcagta     600
gtcgcgtccc ggcaccggcg ggtgccggga cctcggcc                             638
```

<210> SEQ ID NO 2
<211> LENGTH: 183
<212> TYPE: PRT
<213> ORGANISM: Streptomyces avidinii

<400> SEQUENCE: 2

Met Arg Lys Ile Val Val Ala Ala Ile Ala Val Ser Leu Thr Thr Val
1               5                   10                  15

Ser Ile Thr Ala Ser Ala Ser Ala Asp Pro Ser Lys Asp Ser Lys Ala
            20                  25                  30

Gln Val Ser Ala Ala Glu Ala Gly Ile Thr Gly Thr Trp Tyr Asn Gln

```
                35                  40                  45
Leu Gly Ser Thr Phe Ile Val Thr Ala Gly Ala Asp Gly Ala Leu Thr
        50                  55                  60
Gly Thr Tyr Glu Ser Ala Val Gly Asn Ala Glu Ser Arg Tyr Val Leu
 65                  70                  75                  80
Thr Gly Arg Tyr Asp Ser Ala Pro Ala Thr Asp Gly Ser Gly Thr Ala
                85                  90                  95
Leu Gly Trp Thr Val Ala Trp Lys Asn Asn Tyr Arg Asn Ala His Ser
            100                 105                 110
Ala Thr Thr Trp Ser Gly Gln Tyr Val Gly Gly Ala Glu Ala Arg Ile
        115                 120                 125
Asn Thr Gln Trp Leu Leu Thr Ser Gly Thr Thr Glu Ala Asn Ala Trp
    130                 135                 140
Lys Ser Thr Leu Val Gly His Asp Thr Phe Thr Lys Val Lys Pro Ser
145                 150                 155                 160
Ala Ala Ser Ile Asp Ala Ala Lys Lys Ala Gly Val Asn Asn Gly Asn
                165                 170                 175
Pro Leu Asp Ala Val Gln Gln
            180

<210> SEQ ID NO 3
<211> LENGTH: 1614
<212> TYPE: DNA
<213> ORGANISM: Artificial Sequence
<220> FEATURE:
<223> OTHER INFORMATION: huNR-LU-10 single chain antibody-genomic
      streptavidin fusion.

<400> SEQUENCE: 3
gaattcacga agtaaccgac aggactcggc cattctttgg ccgaaattcc tttgcagaaa      60
atgttgttga gaaccctccg atggctagta cgatttacac cgaacatgtg cccttggcaa     120
ccatcgaccc ggacctcgac catccagttc tgccgccaaa gacacatgcc gcactgctgt     180
ttgttcaccg acaccgtcag gtgcacggcc gaggtcacaa accttgacgg gcgggatacg     240
gacggcgcac gccacagcgc gccctccgtc ccccgccggg caacaactag ggagtatttt     300
tcgtgtctca catgcgcaa gatcgtcgtt gcagccatcg ccgtttccct gaccacggtc       360
tcgattacgg ccatggctga catccagatg actcagtctc catcgtcctt gtctgcctct     420
gtgggagaca gagtcacgat cacttgtcgg gctagtcagg gcattagagg taatttagac     480
tggtatcagc agaaacctgg taagggaccg aaactcctaa tctactccac atccaattta     540
aattctggtg tcccatcaag gttcagtggc agtgggtctg ggtcagatta tactctcacc     600
atcagcagcc ttcagcctga agatttcgca acgtattact gtctacagcg taatgcgtat     660
ccgtacacgt tcggacaagg gaccaagctg gagatcaaga tctctggtgg cggtggctcg     720
ggcggtggtg ggtcggtgg cggaggctcg agccaggttc agctggtcca gtctggggca     780
gaggtgaaaa agccaggggc ctcagtcaag gtgtcctgca aggcttctgg cttcaacatt     840
aaagacacct atatgcactg ggtgaggcag gcacctggac agggcctgca gtggatggga     900
aggattgatc ctgcgaatgg taatactaaa tccgacctgt ccttccaggg cagggtgact     960
ataacagcag acacgtccat caacacagcc tacatggaac tcagcagcct gaggtctgac    1020
gacactgccg tctattactg ttctagagag gtcctaactg ggacgtggtc tttggactac    1080
tggggtcaag gaaccttagt caccgtgagc tctggctctg gttcggcaga ccccctccaag   1140
gactcgaagg cccaggtctc ggccgccgag gccggcatca ccggcacctg gtacaaccag    1200
```

```
ctcggctcga ccttcatcgt gaccgcgggc gccgacggcg ccctgaccgg aacctacgag    1260
tcggccgtcg gcaacgccga gagccgctac gtcctgaccg gtcgttacga cagcgcccg     1320 gccaccgacg gcagcggcac cgccctcggt tggacggtgg cctggaagaa taactaccgc    1380
aacgcccact ccgcgaccac gtggagcggc cagtacgtcg gcggcgccga ggcgaggatc    1440
aacacccagt ggctgctgac ctccggcacc accgaggcca acgcctggaa gtccacgctg    1500
gtcggccacg acaccttcac caaggtgaag ccgtccgccg cctccatcga cgcggcgaag    1560
aaggccggcg tcaacaacgg caacccgctc gacgccgttc agcagtaagg atcc          1614
```

<210> SEQ ID NO 4
<211> LENGTH: 431
<212> TYPE: PRT
<213> ORGANISM: Artificial Sequence
<220> FEATURE:
<223> OTHER INFORMATION: Predicted amino acid sequence for huNR-LU-10
      single chain antibody-genomic streptavidin fusion.

<400> SEQUENCE: 4

```
Met Arg Lys Ile Val Val Ala Ile Ala Val Ser Leu Thr Thr Val
 1               5                  10                  15

Ser Ile Thr Ala Met Ala Asp Ile Gln Met Thr Gln Ser Pro Ser
                20                  25                  30

Leu Ser Ala Ser Val Gly Asp Arg Val Thr Ile Thr Cys Arg Ala Ser
                35                  40                  45

Gln Gly Ile Arg Gly Asn Leu Asp Trp Tyr Gln Gln Lys Pro Gly Lys
    50                  55                  60

Gly Pro Lys Leu Leu Ile Tyr Ser Thr Ser Asn Leu Asn Ser Gly Val
65                  70                  75                  80

Pro Ser Arg Phe Ser Gly Ser Gly Ser Gly Ser Asp Tyr Thr Leu Thr
                85                  90                  95

Ile Ser Ser Leu Gln Pro Glu Asp Phe Ala Thr Tyr Tyr Cys Leu Gln
                100                 105                 110

Arg Asn Ala Tyr Pro Tyr Thr Phe Gly Gln Gly Thr Lys Leu Glu Ile
            115                 120                 125

Lys Ile Ser Gly Gly Gly Gly Ser Gly Gly Gly Gly Ser Gly Gly Gly
            130                 135                 140

Gly Ser Ser Gln Val Gln Leu Val Gln Ser Gly Ala Glu Val Lys Lys
145                 150                 155                 160

Pro Gly Ala Ser Val Lys Val Ser Cys Lys Ala Ser Gly Phe Asn Ile
                165                 170                 175

Lys Asp Thr Tyr Met His Trp Val Arg Gln Ala Pro Gly Gln Gly Leu
                180                 185                 190

Gln Trp Met Gly Arg Ile Asp Pro Ala Asn Gly Asn Thr Lys Ser Asp
            195                 200                 205

Leu Ser Phe Gln Gly Arg Val Thr Ile Thr Ala Asp Thr Ser Ile Asn
            210                 215                 220

Thr Ala Tyr Met Glu Leu Ser Ser Leu Arg Ser Asp Asp Thr Ala Val
225                 230                 235                 240

Tyr Tyr Cys Ser Arg Glu Val Leu Thr Gly Thr Trp Ser Leu Asp Tyr
                245                 250                 255

Trp Gly Gln Gly Thr Leu Val Thr Val Ser Ser Gly Ser Gly Ser Ala
            260                 265                 270

Asp Pro Ser Lys Asp Ser Lys Ala Gln Val Ser Ala Ala Glu Ala Gly
            275                 280                 285
```

```
Ile Thr Gly Thr Trp Tyr Asn Gln Leu Gly Ser Thr Phe Ile Val Thr
    290                 295                 300

Ala Gly Ala Asp Gly Ala Leu Thr Gly Thr Tyr Glu Ser Ala Val Gly
305                 310                 315                 320

Asn Ala Glu Ser Arg Tyr Val Leu Thr Gly Arg Tyr Asp Ser Ala Pro
                325                 330                 335

Ala Thr Asp Gly Ser Gly Thr Ala Leu Gly Trp Thr Val Ala Trp Lys
            340                 345                 350

Asn Asn Tyr Arg Asn Ala His Ser Ala Thr Thr Trp Ser Gly Gln Tyr
        355                 360                 365

Val Gly Gly Ala Glu Ala Arg Ile Asn Thr Gln Trp Leu Leu Thr Ser
    370                 375                 380

Gly Thr Thr Glu Ala Asn Ala Trp Lys Ser Thr Leu Val Gly His Asp
385                 390                 395                 400

Thr Phe Thr Lys Val Lys Pro Ser Ala Ala Ser Ile Asp Ala Ala Lys
                405                 410                 415

Lys Ala Gly Val Asn Asn Gly Asn Pro Leu Asp Ala Val Gln Gln
            420                 425                 430

<210> SEQ ID NO 5
<211> LENGTH: 1239
<212> TYPE: DNA
<213> ORGANISM: Artificial Sequence
<220> FEATURE:
<223> OTHER INFORMATION: B9E9 single chain antibody-genomic streptavidin
      fusion

<400> SEQUENCE: 5
gacatcgtgc tgtcgcagtc tccagcaatc ctgtctgcat ctccagggga gaaggtcaca      60
atgacttgca gggccagctc aagtgtaagt tacatgcact ggtaccagca gaagccagga     120
tcctccccca aaccctggat ttatgccaca tccaacctgg cttctggagt ccctgctcgc     180
ttcagtggca gtgggtctgg gacctcttac tctctcacaa tcagcagagt ggaggctgaa     240
gatgctgcca cttattactg ccagcagtgg attagtaacc cacccacgtt cggtgctggg     300
accaagctgg agctgaagat ctctggtctg aaggcagcc cggaagcagg tctgtctccg     360
gacgcaggtt ccggctcgag ccaggttcag ctggtccagt caggggctga gctggtgaag     420
cctggggcct cagtgaagat gtcctgcaag gcttctggct acacatttac cagttacaat     480
atgcactggg taaagcagac acctggacag ggcctggaat ggattggagc tatttatcca     540
ggaaatggtg atacttccta caatcagaag ttcaaaggca aggccacatt gactgcagac     600
aaatcctcca gcacagccta catgcagctc agcagcctga tctgaggac ctctgcggtc     660 tattactgtg caagagcgca attacgacct aactactggt acttcgatgt ctggggcgca     720
gggaccacgg tcaccgtgag ctctggctct ggttcggcag ccccctccaa ggactcgaag     780
gcccaggtct cggccgccga ggccggcatc accggcacct ggtacaacca gctcggctcg     840
accttcatcg tgaccgcggg cgccgacggc ccctgaccg aacctacga gtcggccgtc     900 ggcaacgccg agagccgcta cgtcctgacc ggtcgttacg acagcgcccc ggccaccgac     960
ggcagcggca ccgccctcgg ttggacggtg gcctggaaga ataactaccg caacgcccac    1020
tccgcgacca cgtggagcgg ccagtacgtc ggcggcgccg aggcgaggat caacacccag    1080
tggctgctga cctccggcac caccgaggcc aacgcctgga gtccacgct ggtcggccac    1140 gacaccttca ccaaggtgaa gccgtccgcc gcctccatcg acgcggcgaa gaaggccggc    1200
```
gtcaacaacg gcaacccgct cgacgccgtt cagcagtaa            1239

<210> SEQ ID NO 6
<211> LENGTH: 412
<212> TYPE: PRT
<213> ORGANISM: Artificial Sequence
<220> FEATURE:
<223> OTHER INFORMATION: Predicted amino acid sequence of B9E9 single
    chain antibody-genomic streptavidin fusion

<400> SEQUENCE: 6

```
Asp Ile Val Leu Ser Gln Ser Pro Ala Ile Leu Ser Ala Ser Pro Gly
 1               5                  10                  15

Glu Lys Val Thr Met Thr Cys Arg Ala Ser Ser Val Ser Tyr Met
             20                  25                  30

His Trp Tyr Gln Gln Lys Pro Gly Ser Ser Pro Lys Pro Trp Ile Tyr
         35                  40                  45

Ala Thr Ser Asn Leu Ala Ser Gly Val Pro Ala Arg Phe Ser Gly Ser
     50                  55                  60

Gly Ser Gly Thr Ser Tyr Ser Leu Thr Ile Ser Arg Val Glu Ala Glu
 65                  70                  75                  80

Asp Ala Ala Thr Tyr Tyr Cys Gln Gln Trp Ile Ser Asn Pro Pro Thr
                 85                  90                  95

Phe Gly Ala Gly Thr Lys Leu Glu Leu Lys Ile Ser Gly Leu Glu Gly
            100                 105                 110

Ser Pro Glu Ala Gly Leu Ser Pro Asp Ala Gly Ser Gly Ser Ser Gln
        115                 120                 125

Val Gln Leu Val Gln Ser Gly Ala Glu Leu Val Lys Pro Gly Ala Ser
    130                 135                 140

Val Lys Met Ser Cys Lys Ala Ser Gly Tyr Thr Phe Thr Ser Tyr Asn
145                 150                 155                 160

Met His Trp Val Lys Gln Thr Pro Gly Gln Gly Leu Glu Trp Ile Gly
                165                 170                 175

Ala Ile Tyr Pro Gly Asn Gly Asp Thr Ser Tyr Asn Gln Lys Phe Lys
            180                 185                 190

Gly Lys Ala Thr Leu Thr Ala Asp Lys Ser Ser Ser Thr Ala Tyr Met
        195                 200                 205

Gln Leu Ser Ser Leu Thr Ser Glu Asp Ser Ala Val Tyr Tyr Cys Ala
    210                 215                 220

Arg Ala Gln Leu Arg Pro Asn Tyr Trp Tyr Phe Asp Val Trp Gly Ala
225                 230                 235                 240

Gly Thr Thr Val Thr Val Ser Ser Gly Ser Gly Ser Ala Asp Pro Ser
                245                 250                 255

Lys Asp Ser Lys Ala Gln Val Ser Ala Ala Glu Ala Gly Ile Thr Gly
            260                 265                 270

Thr Trp Tyr Asn Gln Leu Gly Ser Thr Phe Ile Val Thr Ala Gly Ala
        275                 280                 285

Asp Gly Ala Leu Thr Gly Thr Tyr Glu Ser Ala Val Gly Asn Ala Glu
    290                 295                 300

Ser Arg Tyr Val Leu Thr Gly Arg Tyr Asp Ser Ala Pro Ala Thr Asp
305                 310                 315                 320

Gly Ser Gly Thr Ala Leu Gly Trp Thr Val Ala Trp Lys Asn Asn Tyr
                325                 330                 335

Arg Asn Ala His Ser Ala Thr Thr Trp Ser Gly Gln Tyr Val Gly Gly
            340                 345                 350
```

Ala Glu Ala Arg Ile Asn Thr Gln Trp Leu Leu Thr Ser Gly Thr Thr
            355                 360                 365

Glu Ala Asn Ala Trp Lys Ser Thr Leu Val Gly His Asp Thr Phe Thr
        370                 375                 380

Lys Val Lys Pro Ser Ala Ala Ser Ile Asp Ala Ala Lys Lys Ala Gly
385                 390                 395                 400

Val Asn Asn Gly Asn Pro Leu Asp Ala Val Gln Gln
                405                 410

<210> SEQ ID NO 7
<211> LENGTH: 1280
<212> TYPE: DNA
<213> ORGANISM: Artificial Sequence
<220> FEATURE:
<223> OTHER INFORMATION: B9E9 single chain antibody-genomic streptavidin
      fusion construct encoding VH-linker-VL-linker-Streptavidin

<400> SEQUENCE: 7
ccatggctca ggttcagctg gtccagtcag gggctgagct ggtgaagcct ggggcctcag      60
tgaagatgtc ctgcaaggct tctggctaca catttaccag ttacaatatg cactgggtaa     120
agcagacacc tggacagggc ctggaatgga ttggagctat ttatccagga aatggtgata     180
cttcctacaa tcagaagttc aaaggcaagg ccacattgac tgcagacaaa tcctccagca     240
cagcctacat gcagctcagc agcctgacat ctgaggactc tgcggtctat tactgtgcaa     300
gagcgcaatt acgacctaac tactggtact cgatgtctg gggcgcaggg accacggtca     360
ccgtgagcaa gatctctggt ggcggtggct cgggcggtgg tgggtcgggt ggcggcggct     420
cgggtggtgg tgggtcgggc ggcggcggct cgagcgacat cgtgctgtcg cagtctccag     480
caatcctgtc tgcatctcca ggggagaagg tcacaatgac ttgcagggcc agctcaagtg     540
taagttacat gcactggtac cagcagaagc aggatcctc ccccaaaccc tggatttatg     600
ccacatccaa cctggcttct ggagtccctg ctcgcttcag tggcagtggg tctgggacct     660
cttactctct cacaatcagc agagtggagg ctgaagatgc tgccacttat tactgccagc     720
agtggattag taacccaccc acgttcggtg ctggaccaa gctggagctg aagagctctg     780
gctctggttc ggcagacccc tccaaggact cgaaggccca ggtctcggcc gccgaggccg     840
gcatcaccgg cacctggtac aaccagctcg gctcgacctt catcgtgacc gcgggcgccg     900
acggcgccct gaccggaacc tacgagtcgg ccgtcggcaa cgccgagagc cgctacgtcc     960
tgaccggtcg ttacgacagc gccccggcca ccgacgcag cggcaccgcc ctcggttgga    1020
cggtggcctg gaagaataac taccgcaacg cccactccgc gaccacgtgg agcggccagt    1080
acgtcggcgg cgccgaggcg aggatcaaca cccagtggct gctgacctcc ggcaccaccg    1140
aggccaacgc ctggaagtcc acgctggtcg gccacgacac cttcaccaag gtgaagccgt    1200
ccgccgcctc catcgacgcg gcgaagaagg ccggcgtcaa caacggcaac ccgctcgacg    1260
ccgttcagca gtaaggatcc                                               1280

<210> SEQ ID NO 8
<211> LENGTH: 423
<212> TYPE: PRT
<213> ORGANISM: Artificial Sequence
<220> FEATURE:
<223> OTHER INFORMATION: Predicted amino acid sequence of B9E9 single
      chain antibody- genomic streptavidin fusion construct encoding
      VH-linker-VL-linker- Streptavidin

<400> SEQUENCE: 8

```
Met Ala Gln Val Gln Leu Val Gln Ser Gly Ala Glu Leu Val Lys Pro
1               5                   10                  15
Gly Ala Ser Val Lys Met Ser Cys Lys Ala Ser Gly Tyr Thr Phe Thr
            20                  25                  30
Ser Tyr Asn Met His Trp Val Lys Gln Thr Pro Gly Gln Gly Leu Glu
        35                  40                  45
Trp Ile Gly Ala Ile Tyr Pro Gly Asn Gly Asp Thr Ser Tyr Asn Gln
50                  55                  60
Lys Phe Lys Gly Lys Ala Thr Leu Thr Ala Asp Lys Ser Ser Ser Thr
65                  70                  75                  80
Ala Tyr Met Gln Leu Ser Ser Leu Thr Ser Glu Asp Ser Ala Val Tyr
            85                  90                  95
Tyr Cys Ala Arg Ala Gln Leu Arg Pro Asn Tyr Trp Tyr Phe Asp Val
        100                 105                 110
Trp Gly Ala Gly Thr Thr Val Thr Val Ser Lys Ile Ser Gly Gly Gly
        115                 120                 125
Gly Ser Gly Gly Gly Gly Ser Gly Gly Gly Ser Gly Gly Gly Gly
    130                 135                 140
Ser Gly Gly Gly Gly Ser Ser Asp Ile Val Leu Ser Gln Ser Pro Ala
145                 150                 155                 160
Ile Leu Ser Ala Ser Pro Gly Glu Lys Val Thr Met Thr Cys Arg Ala
            165                 170                 175
Ser Ser Ser Val Ser Tyr Met His Trp Tyr Gln Gln Lys Pro Gly Ser
        180                 185                 190
Ser Pro Lys Pro Trp Ile Tyr Ala Thr Ser Asn Leu Ala Ser Gly Val
    195                 200                 205
Pro Ala Arg Phe Ser Gly Ser Gly Ser Gly Thr Ser Tyr Ser Leu Thr
        210                 215                 220
Ile Ser Arg Val Glu Ala Glu Asp Ala Ala Thr Tyr Tyr Cys Gln Gln
225                 230                 235                 240
Trp Ile Ser Asn Pro Pro Thr Phe Gly Ala Gly Thr Lys Leu Glu Leu
            245                 250                 255
Lys Ser Ser Gly Ser Gly Ser Ala Asp Pro Ser Lys Asp Ser Lys Ala
        260                 265                 270
Gln Val Ser Ala Ala Glu Ala Gly Ile Thr Gly Thr Trp Tyr Asn Gln
    275                 280                 285
Leu Gly Ser Thr Phe Ile Val Thr Ala Gly Ala Asp Gly Ala Leu Thr
        290                 295                 300
Gly Thr Tyr Glu Ser Ala Val Gly Asn Ala Glu Ser Arg Tyr Val Leu
305                 310                 315                 320
Thr Gly Arg Tyr Asp Ser Ala Pro Ala Thr Asp Gly Ser Gly Thr Ala
            325                 330                 335
Leu Gly Trp Thr Val Ala Trp Lys Asn Asn Tyr Arg Asn Ala His Ser
        340                 345                 350
Ala Thr Thr Trp Ser Gly Gln Tyr Val Gly Gly Ala Glu Ala Arg Ile
    355                 360                 365
Asn Thr Gln Trp Leu Leu Thr Ser Gly Thr Thr Glu Ala Asn Ala Trp
        370                 375                 380
Lys Ser Thr Leu Val Gly His Asp Thr Phe Thr Lys Val Lys Pro Ser
385                 390                 395                 400
Ala Ala Ser Ile Asp Ala Ala Lys Lys Ala Gly Val Asn Asn Gly Asn
            405                 410                 415
Pro Leu Asp Ala Val Gln Gln
```

```
                420

<210> SEQ ID NO 9
<211> LENGTH: 18
<212> TYPE: PRT
<213> ORGANISM: Artificial Sequence
<220> FEATURE:
<223> OTHER INFORMATION: pKOD linker

<400> SEQUENCE: 9

Gly Leu Glu Gly Ser Pro Glu Ala Gly Leu Ser Pro Asp Ala Gly Ser
 1               5                   10                  15

Gly Ser

<210> SEQ ID NO 10
<211> LENGTH: 15
<212> TYPE: PRT
<213> ORGANISM: Artificial Sequence
<220> FEATURE:
<223> OTHER INFORMATION: Linker used to create a scFvSA version of
      anti-CD20mAb, B9E9 in the VLVH orientation

<400> SEQUENCE: 10

Gly Gly Gly Gly Ser Gly Gly Gly Ser Gly Gly Gly Gly Ser
 1               5                   10                  15

<210> SEQ ID NO 11
<211> LENGTH: 25
<212> TYPE: PRT
<213> ORGANISM: Artificial Sequence
<220> FEATURE:
<223> OTHER INFORMATION: Linker used to create a  version of B9E9 scFvSA
      in the VHVL orientation

<400> SEQUENCE: 11

Gly Gly Gly Gly Ser Gly Gly Gly Gly Ser Gly Gly Gly Gly Ser Gly
 1               5                   10                  15

Gly Gly Gly Ser Gly Gly Gly Gly Ser
            20                  25

<210> SEQ ID NO 12
<211> LENGTH: 32
<212> TYPE: DNA
<213> ORGANISM: Artificial Sequence
<220> FEATURE:
<223> OTHER INFORMATION: Oligonucleotide primer

<400> SEQUENCE: 12
tgccgtgaat tcgtsmarct gcagsartcw gg                                    32

<210> SEQ ID NO 13
<211> LENGTH: 31
<212> TYPE: DNA
<213> ORGANISM: Artificial Sequence
<220> FEATURE:
<223> OTHER INFORMATION: Oligonucleotide primer

<400> SEQUENCE: 13
tgccgtgaat tccattswgc tgaccartct c                                     31

<210> SEQ ID NO 14
<211> LENGTH: 35
<212> TYPE: DNA
<213> ORGANISM: Artificial Sequence
<220> FEATURE:
<223> OTHER INFORMATION: Oligonucleotide primer
```

```
<400> SEQUENCE: 14
tagctggcgg ccgccctgtt gaagctcttg acaat                              35

<210> SEQ ID NO 15
<211> LENGTH: 34
<212> TYPE: DNA
<213> ORGANISM: Artificial Sequence
<220> FEATURE:
<223> OTHER INFORMATION: Oligonucleotide primer

<400> SEQUENCE: 15
tagctggcgg ccgctttctt gtccaccttg gtgc                               34

<210> SEQ ID NO 16
<211> LENGTH: 47
<212> TYPE: DNA
<213> ORGANISM: Artificial Sequence
<220> FEATURE:
<223> OTHER INFORMATION: Oligonucleotide primer

<400> SEQUENCE: 16
ttacggccat ggctgacatc gtgctgcagt ctccagcaat cctgtct                 47

<210> SEQ ID NO 17
<211> LENGTH: 32
<212> TYPE: DNA
<213> ORGANISM: Artificial Sequence
<220> FEATURE:
<223> OTHER INFORMATION: Oligonucleotide primer

<400> SEQUENCE: 17
caccagagat cttcagctcc agcttggtcc ca                                 32

<210> SEQ ID NO 18
<211> LENGTH: 52
<212> TYPE: DNA
<213> ORGANISM: Artificial Sequence
<220> FEATURE:
<223> OTHER INFORMATION: Oligonucleotide primer

<400> SEQUENCE: 18
cggaggctcg agccaggttc agctggtcca gtcaggggct gagctggtga ag           52

<210> SEQ ID NO 19
<211> LENGTH: 38
<212> TYPE: DNA
<213> ORGANISM: Artificial Sequence
<220> FEATURE:
<223> OTHER INFORMATION: Oligonucleotide primer

<400> SEQUENCE: 19
gagccagagc tcacggtgac cgtggtccct gcgcccca                           38

<210> SEQ ID NO 20
<211> LENGTH: 58
<212> TYPE: DNA
<213> ORGANISM: Artificial Sequence
<220> FEATURE:
<223> OTHER INFORMATION: Oligonucleotide primer

<400> SEQUENCE: 20
gatctctggt ctggaaggca gcccggaagc aggtctgtct ccggacgcag gttccggc     58

<210> SEQ ID NO 21
```

```
<211> LENGTH: 58
<212> TYPE: DNA
<213> ORGANISM: Artificial Sequence
<220> FEATURE:
<223> OTHER INFORMATION: Oligonucleotide primer

<400> SEQUENCE: 21
tcgagccgga acctgcgtcc ggagacagac ctgcttccgg gctgccttcc agaccaga         58

<210> SEQ ID NO 22
<211> LENGTH: 50
<212> TYPE: DNA
<213> ORGANISM: Artificial Sequence
<220> FEATURE:
<223> OTHER INFORMATION: Oligonucleotide primer

<400> SEQUENCE: 22
ttacggccat ggctgacatc gtgctgtcgc agtctccagc aatcctgtct                  50

<210> SEQ ID NO 23
<211> LENGTH: 37
<212> TYPE: DNA
<213> ORGANISM: Artificial Sequence
<220> FEATURE:
<223> OTHER INFORMATION: Oligonucleotide primer

<400> SEQUENCE: 23
ttccggctcg agcgacatcg tgctgtcgca gtctcca                                37

<210> SEQ ID NO 24
<211> LENGTH: 32
<212> TYPE: DNA
<213> ORGANISM: Artificial Sequence
<220> FEATURE:
<223> OTHER INFORMATION: Oligonucleotide primer

<400> SEQUENCE: 24
gagccagagc tcttcagctc cagcttggtc cc                                     32

<210> SEQ ID NO 25
<211> LENGTH: 35
<212> TYPE: DNA
<213> ORGANISM: Artificial Sequence
<220> FEATURE:
<223> OTHER INFORMATION: Oligonucleotide primer

<400> SEQUENCE: 25
ttacggccat ggctcaggtt cagctggtcc agtca                                  35

<210> SEQ ID NO 26
<211> LENGTH: 35
<212> TYPE: DNA
<213> ORGANISM: Artificial Sequence
<220> FEATURE:
<223> OTHER INFORMATION: Oligonucleotide primer

<400> SEQUENCE: 26
agaccagaga tcttgctcac ggtgaccgtg gtccc                                  35

<210> SEQ ID NO 27
<211> LENGTH: 79
<212> TYPE: DNA
<213> ORGANISM: Artificial Sequence
<220> FEATURE:
<223> OTHER INFORMATION: Oligonucleotide primer

<400> SEQUENCE: 27
```

-continued

```
gatctctggt ggcggtggct cgggcggtgg tgggtcgggt ggcggcggct cgggtggtgg    60
tgggtcgggc ggcggcggc                                                  79
```

<210> SEQ ID NO 28
<211> LENGTH: 79
<212> TYPE: DNA
<213> ORGANISM: Artificial Sequence
<220> FEATURE:
<223> OTHER INFORMATION: Oligonucleotide primer

<400> SEQUENCE: 28

```
tcgagccgcc gccgcccgac ccaccaccac ccgagccgcc gccacccgac ccaccaccgc    60
ccgagccacc gccaccaga                                                  79
```

<210> SEQ ID NO 29
<211> LENGTH: 18
<212> TYPE: PRT
<213> ORGANISM: Artificial Sequence
<220> FEATURE:
<223> OTHER INFORMATION: Linker sequence

<400> SEQUENCE: 29

Gly Gly Gly Gly Ser Gly Gly Gly Gly Ser Gly Gly Gly Gly Ser Gly
 1               5                  10                  15

Gly Ser

<210> SEQ ID NO 30
<211> LENGTH: 35
<212> TYPE: PRT
<213> ORGANISM: Artificial Sequence
<220> FEATURE:
<223> OTHER INFORMATION: Linker sequence

<400> SEQUENCE: 30

Gly Gly Gly Gly Ser Gly Gly Gly Gly Ser Gly Gly Gly Gly Ser Gly
 1               5                  10                  15

Gly Gly Gly Ser Gly Gly Gly Gly Ser Gly Gly Gly Ser Gly Gly
            20                  25                  30

Gly Gly Ser
        35

<210> SEQ ID NO 31
<211> LENGTH: 18
<212> TYPE: PRT
<213> ORGANISM: Artificial Sequence
<220> FEATURE:
<223> OTHER INFORMATION: Linker sequence pKOD2

<400> SEQUENCE: 31

Gly Leu Glu Gly Ser Pro Glu Ala Gly Leu Ser Pro Asp Ala Gly Ser
 1               5                  10                  15

Asp Ser

<210> SEQ ID NO 32
<211> LENGTH: 21
<212> TYPE: DNA
<213> ORGANISM: Artificial Sequence
<220> FEATURE:
<223> OTHER INFORMATION: Oligonucleotide primer

<400> SEQUENCE: 32

```
acgacggttg ctgcggcggt c                                               21
```

<210> SEQ ID NO 33
<211> LENGTH: 21
<212> TYPE: DNA
<213> ORGANISM: Artificial Sequence
<220> FEATURE:
<223> OTHER INFORMATION: Oligonucleotide primer

<400> SEQUENCE: 33
aggctcatta atgatgcggg t                                              21

<210> SEQ ID NO 34
<211> LENGTH: 33
<212> TYPE: DNA
<213> ORGANISM: Artificial Sequence
<220> FEATURE:
<223> OTHER INFORMATION: Oligonucleotide primer

<400> SEQUENCE: 34
ggatccaagc ttacgatcac ggtcatgaac acg                                 33

<210> SEQ ID NO 35
<211> LENGTH: 33
<212> TYPE: DNA
<213> ORGANISM: Artificial Sequence
<220> FEATURE:
<223> OTHER INFORMATION: Oligonucleotide primer

<400> SEQUENCE: 35
ctcgagaagc tttaactaaa ttaatacagc gga                                 33

<210> SEQ ID NO 36
<211> LENGTH: 783
<212> TYPE: DNA
<213> ORGANISM: Artificial Sequence
<220> FEATURE:
<223> OTHER INFORMATION: T84.66 single chain antibody-genomic
    Streptavidin fusion construct

<400> SEQUENCE: 36
gaggttcagc tgcagcagtc cggggcagag cttgtggagc caggggcctc agtcaagttg     60
tcctgcacag cttctggctt caacattaaa gacacctata tgcactgggt gaagcagagg    120
cctgaacagg gcctggaatg gattggaagg attgatcctg cgaatggtaa tagtaaatat    180
gtcccgaagt tccagggcaa ggccactata acagcagaca catcctccaa cacagcctac    240
ctgcagctca ccagcctgac atctgaggac actgccgtct attattgtgc tccgtttggt    300
tactacgtgt ctgactatgc tatggcctac tggggtcaag aacctcagt caccgtctcc    360 tcaaagatct ctggtggcgg tggctcgggc ggtggtgggt cgggtggcgg cggctcgggt    420
ggtggtgggt cgggcggcgg cggctcgagc gacattgtgc tgacccaatc tccagcttct    480
ttggctgtgt ctcttgggca gagggccact atgtcctgca gagccggtga agtgttgat    540 attttggcg ttgggttttt gcactggtac cagcagaaac caggacagcc acccaaactc    600
ctcatctatc gtgcatccaa cctagaatct gggatccctg tcaggttcag tggcactggg    660
tctaggacag acttcaccct catcattgat cctgtggagg ctgatgatgt tgccacctat    720
tactgtcagc aaactaatga ggatccgtac acgttcggag ggggaccaa gctggaaata    780 aag                                                                 783

<210> SEQ ID NO 37
<211> LENGTH: 786

```
<212> TYPE: DNA
<213> ORGANISM: Artificial Sequence
<220> FEATURE:
<223> OTHER INFORMATION: Col-1 single chain antibody-genomic
      Streptavidin fusion construct

<400> SEQUENCE: 37
gaagttcagc tgcagcagtc tggggcagaa cttgtgcgtt cagggggcctc agtcaaaatg      60 tcctgcaccg cttctggctt caacattaaa gattactata tgcattgggt gaaacagcgt     120
ccggaacagg gcctggaatg gattggttgg attgatccgg aaaatggtga taccgaatat     180
gccccgaaat tccagggcaa agccacgatg accaccgata cctcctccaa caccgcctac     240
ctgcagctca gcagcctgac ctctgaagat accgccgtct attactgtaa tacccgtggt     300
ctatctacca tgattacgac gcgttggttc ttcgatgtct ggggcgcagg gaccacggtc     360
accgtctcca agatctctgg tggcggtggc tcgggcggtg gtgggtcggg tggcggcggc     420
tcgggtggtg gtgggtcggg cggcggcggc tcgagcgata ttgtgctgac ccagtctccg     480
gcttccttaa ccgtatctct gggtctgcgt gccaccatct catgccgtgc agcaaaagt     540 gtcagtgcat ctggctatag ttatatgcat tggtaccaac agcgtccggg tcagccgccg     600
aaactcctca tctatcttgc atccaaccta caatctggtg tcccggcccg tttcagtggc     660
agtgggtctg ggaccgattt cacccctcaac atccatccgg tggaagaaga agatgctgca     720
acctattact gtcagcatag tcgtgaactt ccgacgttcg gtggtggcac caaactggaa     780
atcaag                                                               786

<210> SEQ ID NO 38
<211> LENGTH: 771
<212> TYPE: DNA
<213> ORGANISM: Artificial Sequence
<220> FEATURE:
<223> OTHER INFORMATION: PR1A3 single chain antibody-genomic
      Streptavidin fusion construct

<400> SEQUENCE: 38
caggtgaagc tgcagcagtc aggtccggag ttgaagaagc cgggtgagac cgtcaagatc      60
agctgcaagg cttctggtta taccttcacc gtgtttggta tgaactgggt gaagcaggct     120
ccgggcaagg gtttaaagtg gatgggctgg attaacacca aaactggtga agcaaccctat     180 gttgaagagt ttaagggtcg cttttgccttc tctttggaga cctctgccac cactgcctat     240
ttgcagatca caaacctcaa aaatgaggac acggctaaat atttctgtgc acgttgggac     300
ttctatgatt acgtggaagc tatggattac tggggccaag gaccacggt caccgtctcc     360 aagatctctg gtggcggtgg ctcgggcggt ggtgggtcgg gtggcggcgg ctcgggtggt     420
ggtgggtcgg gcggcggcgg ctcgagcgat attgtgatga cccagtctca acgtttcatg     480
tccacttcag taggtgatcg tgtcagcgtc acctgcaaag ccagtcagaa tgtgggtacg     540
aatgttgcct ggtatcaaca gaaaccgggt caatccccga agcactgat ttactcggca     600 tcctaccgtt acagtggtgt cccggatcgc ttcaccggca gtggttctgg gaccgatttc     660
acgctcacca tcagcaatgt acagtctgaa gacttggcgg agtatttctg tcatcaatat     720
tacacctatc cgttattcac gttcggctcg gggaccaagt tggaaatgaa g             771

<210> SEQ ID NO 39
<211> LENGTH: 762
<212> TYPE: DNA
<213> ORGANISM: Artificial Sequence
<220> FEATURE:
```

```
<223> OTHER INFORMATION: MFE-23 single chain antibody-genomic
      Streptavidin fusion construct

<400> SEQUENCE: 39
caggtgaaac tgcagcagtc tggtgcagaa cttgtgcgtt cagggacctc agtcaaattg      60
tcctgcaccg cttctggctt caacattaaa gattcctata tgcattggtt gcgtcagggt     120
ccggaacagg gcctggaatg gattggttgg attgatccgg agaatggtga tactgaatat     180
gcaccgaagt tccagggcaa agccaccttt actaccgata cctcctccaa caccgcctac     240
ctgcagctca gcagcctgac ctctgaagat actgccgtct attattgtaa tgaagggact     300
ccgactggtc cgtactactt tgattactgg ggtcaaggga ccacggtcac cgtctccaag     360
atctctggtg gcggtggctc gggcggtggt gggtcgggtg gcggcggctc gggtggtggt     420
gggtcgggcg gcggcggctc gagcgaaaat gtgctcaccc agtctccggc aatcatgtct     480
gcatctccgg gtgagaaagt caccattacc tgcagtgcca gctcaagtgt aagttacatg     540
cattggttcc agcagaaacc gggtacttct ccgaaactct ggatttatag cacctccaac     600
ctggcttctg gtgttccggc tcgcttcagt ggcagtggtt ctgggacctc ttactctctc     660
accatcagcc gtatggaagc tgaagatgct gccacttatt actgccagca acgtagtagt     720
tatccgctca cgttcggtgc tggcaccaaa ctggaactga ag                        762

<210> SEQ ID NO 40
<211> LENGTH: 765
<212> TYPE: DNA
<213> ORGANISM: Artificial Sequence
<220> FEATURE:
<223> OTHER INFORMATION: Nrco-2 single chain antibody-genomic
      Streptavidin fusion construct

<400> SEQUENCE: 40
caggtccaac tacagcagtc agggggagac ttagtgaagc ctggagggtc cctaaaattc      60
tcctgtgcag cctctggatt cccctttcaat cgctatgcca tgtcttgggt tcgccagact    120
ccagagaaga ggctggagtg ggtcgcattc attagtagtg atggtatcgc ctactatgca     180
gacagtgtga agggccgatt caccatctcc agagataatg ccaggaacat cctgtaccta     240
caaatgagca gtctgaggtc tgaggacacg gccatgtatt actgtgcaag agtttattac     300
tacggtagta gttactttga ctactggggc caagggacca cggtcaccgt gagcaagatc     360
tctggtggcg gtggctcggg cggtggtggg tcgggtggcg gcggctcggg tggtggtggg     420
tcgggcggcg gcggctcgag cgacatccag atgactcagt ctccaaaatt catgcccaca     480
tcagtaggag acagggtcag cgtcacctgc aaggccagtc agaatgcggg tactaatgta     540
gcctggtatc aacagaaacc aggcaatct cctaaagcac tgatttactc ggcatcgtct     600
cggaacagtg gagtccctga tcgcttcaca ggcagtggat ctgggacaga tttcactctc     660
accatcagca atgtgcagtc tgaagacttg gcagagtatt tctgtcagca atataacagc     720
tatcctctgg tcacgttcgg tgctgggacc aagctggaaa taaag                     765

<210> SEQ ID NO 41
<211> LENGTH: 768
<212> TYPE: DNA
<213> ORGANISM: Artificial Sequence
<220> FEATURE:
<223> OTHER INFORMATION: CC49 single chain antibody-genomic
      Streptavidin fusion construct

<400> SEQUENCE: 41
```

```
caggttcagt tgcagcagtc tgatgctgaa ttggtgaaac cgggtgcttc agtgaaaatt      60
tcctgcaaag cttctggcta caccttcacc gatcatgcaa ttcattgggt gaaacagaac     120
ccggaacagg gcctggaatg gattggttat ttctctccgg gtaatgatga tttcaaatac     180
aatgaacgtt tcaaaggcaa agccacgctg accgcagata atcctccag caccgcctac      240 gtgcagctca acagcctgac gtctgaagat tctgcagtgt atttctgtac gcgttccctg     300
aatatggcct actgggtca aggtacctca gtcaccgtct ccaagatctc tggtggcggt      360
ggctcgggcg gtggtgggtc gggtggcggc gctcgggtg gtggtgggtc gggcggcggc      420
ggctcgagcg atattgtgat gtcacagtct ccgtcctccc taccgtgtc agttggcgaa      480 aaagttacct tgagctgcaa atccagtcag agccttttat atagtggtaa tcagaaaaac     540
tacttggcct ggtaccagca gaaaccgggt cagtctccga actgctgat ttactgggca      600 tccgctcgtg aatctggggt cccggatcgc ttcaccggca gtggttctgg gaccgatttc     660
accctctcca tcagcagtgt gaaaaccgaa gacctggcag tttattactg tcagcagtat     720
tatagctatc cgctcacgtt cggtgctggg accaaactgg tgctgaag               768

<210> SEQ ID NO 42
<211> LENGTH: 765
<212> TYPE: DNA
<213> ORGANISM: Artificial Sequence
<220> FEATURE:
<223> OTHER INFORMATION: BrE-3 single chain antibody-genomic
      Streptavidin fusion construct

<400> SEQUENCE: 42
gaagtgaaac ttgaagagtc tggtggtggc ttggtgcaac cgggtggctc catgaaactc      60
tcttgtgctg cttctggctt cacctttagt gatgcctgga tggattgggt ccgccagtct     120
ccggagaaag ggcttgaatg ggttgctgaa attcgtaaca aagccaataa tcatggtacc     180
tattatgatg agtctgtgaa agggcgcttc accatctcac gtgatgattc caaaagtcgt     240
gtgtacctgc aaatgattag cttacgtgct gaagataccg gctttatta ctgtaccggg      300 gaatttgcta ctggggcca ggggacgctg gtcaccgtct ctaagatctc tggtggcggt      360
ggctcgggcg gtggtgggtc gggtggcggc ggctcgggtg gtggtgggtc gggcggcggc     420
ggctcgagcg atgttgtgat gacccaaact ccgctctccc tgccggtcac tcttggtgat     480
caagcttcca tctcttgccg ttctagtcag aaccttgtac ataacaatgg taacacctat     540
ttatattggt tcctgcagaa atcaggccag tctccgaaac tgctgattta cgcgcatcc      600 atccgctttt ctggtgtccc ggatcgcttc agtggcagtg gttcagaaac cgatttcacg     660
ctcaagatca gccgtgtgga agctgaagac ctgggtgttt atttctgctt tcaaggtacg     720
catgttccgt ggacgttcgg tggtggcacc aaactggaaa tcaag                     765

<210> SEQ ID NO 43
<211> LENGTH: 741
<212> TYPE: DNA
<213> ORGANISM: Artificial Sequence
<220> FEATURE:
<223> OTHER INFORMATION: ICR12 single chain antibody-genomic
      Streptavidin fusion construct

<400> SEQUENCE: 43
caggtgcagc ttcaggagtc aggacctggc cttgtgaaac cctcacagtc actctccctc      60
acctgttccg tcactggtta ctccatcact actgattact ggggctggat ccggaagttc     120
ccaggaaata aaatggagtg gatgggatac ataagctaca gtggtagcac tggctacaac     180
```

```
ccatctctca aaagtcgaat ctccattact agagacacat cgaagagtca gttcttcctg    240
cagttgaact ctgtaactac tgaggacaca gccacatatt actgtgcaag atacagtagc    300
cttgattact ggggccgagg agtcatggtc gcagtctcca agatctctgg tggcggtggc    360
tcgggcggtg gtgggtcggg tggcggcggc tcgggtggtg gtgggtcggg cggcggcggc    420
tcgagcgatg ttgtgatgac ccagacacca ccgtctttgt cggttgccat tggacaatca    480
gtctccatct cttgcaagtc aagtcagagc ctcgtatata gtgatggaaa gacatatttg    540
cattggttat tacagagtcc tggcaggtct ccgaagcgcc taatctatca ggtgtctaat    600
ctgggctctg gagtccctga caggttcagt ggcactggat cacagaaaga ttttacactt    660
aaaatcagca gagtggaggc tgaggatttg ggagtttact actgcgcgca aactacacat    720
tttcctctca cgttcggttc g                                              741
```

<210> SEQ ID NO 44
<211> LENGTH: 765
<212> TYPE: DNA
<213> ORGANISM: Artificial Sequence
<220> FEATURE:
<223> OTHER INFORMATION: B9E9 single chain antibody-genomic
      Streptavidin fusion construct

<400> SEQUENCE: 44

```
caggttcagc tggtccagtc aggggctgag ctggtgaagc ctggggcctc agtgaagatg    60
tcctgcaagg cttctggcta cacatttacc agttacaata tgcactgggt aaagcagaca    120
cctggacagg gcctggaatg gattggagct atttatccag gaaatggtga tacttcctac    180
aatcagaagt tcaaaggcaa ggccacattg actgcagaca atcctccag cacagcctac    240 atgcagctca gcagcctgac atctgaggac tctgcggtct attactgtgc aagagcgcaa    300
ttacgaccta actactggta cttcgatgtc tggggcgcag gaccacggt caccgtgagc    360 aagatctctg gtggcggtgg ctcgggcggt ggtgggtcgg gtggcggcgg ctcgggtggt    420
ggtgggtcgg gcggcggcgg ctcgagcgac atcgtgctgt cgcagtctcc agcaatcctg    480
tctgcatctc cagggagaa ggtcacaatg acttgcaggg ccagctcaag tgtaagttac    540
atgcactggt accagcagaa gccaggatcc tcccccaaac cctggattta tgccacatcc    600
aacctggctt ctggagtccc tgctcgcttc agtggcagtg gtgtctggga ctcttactct    660
ctcacaatca gcagagtgga ggctgaagat gctgccactt attactgcca gcagtggatt    720
agtaacccac ccacgttcgg tgctgggacc aagctggagc tgaag                   765
```

<210> SEQ ID NO 45
<211> LENGTH: 765
<212> TYPE: DNA
<213> ORGANISM: Artificial Sequence
<220> FEATURE:
<223> OTHER INFORMATION: C2B8 single chain antibody-genomic
      Streptavidin fusion construct

<400> SEQUENCE: 45

```
caggttcagc tgcaacagcc aggggctgag ctggtgaagc ctggggcctc agtgaagatg    60
tcctgcaagg cttctggcta cacatttacc agttacaata tgcactgggt aaagcagaca    120
cctggacagg gcctggaatg gattggagct atttatccag gaaatggtga tacttcctac    180
aatcagaagt tcaaaggcaa ggccacattg actgcagaca atcctccag cacagcctac    240 atgcagctca gcagcctgac atctgaggac tctgcggtct attactgtgc aagaagcacc    300
```

```
tattacggcg gtgattggta cttcaacgtc tggggcgcag ggaccacggt caccgtgagc     360
aagatctctg gtggcggtgg ctcgggcggt ggtgggtcgg gtggcggcgg ctcgggtggt     420
ggtgggtcgg gcggcggcgg ctcgagccag atcgtgctgt cgcagtctcc agcaatcctg     480
tctgcatctc cagggagaa ggtcacaatg acttgcaggg ccagctcaag tgtaagttac     540
attcactggt ttcagcagaa gccaggatcc tcccccaaac cctggattta tgccacatcc     600
aacctggctt ctggagtccc tgtgcgcttc agtggcagtg gtctgggac ctcttactct     660 ctcacaatca gcagagtgga ggctgaagat gctgccactt attactgcca gcagtggacc     720
agtaacccac ccacgttcgg tggcgggacc aagctggaga tcaag                    765

<210> SEQ ID NO 46
<211> LENGTH: 780
<212> TYPE: DNA
<213> ORGANISM: Artificial Sequence
<220> FEATURE:
<223> OTHER INFORMATION: BC8 single chain antibody-genomic
      Streptavidin fusion construct

<400> SEQUENCE: 46
caggttcagc tggtggaatc aggaggtggc ctggtgcagc ctggaggatc cctgaaactc      60
tcctgtgcag cctcaggatt cgatttcagt agatactgga tgagttgggt ccggcaggct     120
ccagggaaag ggctagaatg gattggagag attaatccaa ctagcagtac gataaacttt     180
acgccatctc taaaggataa agtcttcatc tccagagaca cgccaaaaa tacgctgtac     240 ctgcaaatga gcaaagtgag atccgaggac acagcccttt attactgtgc aagagggaac     300
tactataggt acggagatgc tatggactac tggggtcaag gaacctcagt caccgtgagc     360
aagatctctg gtggcggtgg ctcgggcggt ggtgggtcgg gtggcggcgg ctcgggtggt     420
ggtgggtcgg gcggcggcgg ctcgagcgac atcgtgctga cccagtctcc tgcttcctta     480
gctgtatctc tgggacagag ggccaccatc tcatgcaggg ccagcaaaag tgtcagtaca     540
tctggctata gttatctgca ctggtaccaa cagaaaccag gacagccacc caaactcctc     600
atctatcttg catccaacct agaatctggg gtccctgcca ggttcagtgg cagtgggtct     660
gggacagact tcaccctcaa catccatcct gtggaggagg aggatgctgc aacctattac     720
tgtcagcaca gtagggagct tccattcacg ttcggctcgg ggacaaagtt ggaaataaag     780

<210> SEQ ID NO 47
<211> LENGTH: 5
<212> TYPE: PRT
<213> ORGANISM: Artificial Sequence
<220> FEATURE:
<223> OTHER INFORMATION: Gly Ser linker

<400> SEQUENCE: 47

Gly Gly Gly Gly Ser
1               5

<210> SEQ ID NO 48
<211> LENGTH: 1467
<212> TYPE: DNA
<213> ORGANISM: Artificial Sequence
<220> FEATURE:
<223> OTHER INFORMATION: CC49 single chain antibody-genomic streptavidin
      fusion sequence

<400> SEQUENCE: 48
cacagcgcgc cctccgtccc ccgccgggca acaactaggg gagtattttt cgtgtctcac      60
```

```
atgcgcaaga tcgtcgttgc agccatcgcc gtttccctga ccacggtctc gattacggcc     120
atggctcagg ttcagttgca gcagtctgat gctgaattgg tgaaaccggg tgcttcagtg     180
aaaatttcct gcaaagcttc tggctacacc ttcaccgatc atgcaattca ttgggtgaaa     240
cagaacccgg aacagggcct ggaatggatt ggttatttct ctccgggtaa tgatgatttc     300
aaatacaatg aacgtttcaa aggcaaagcc acgctgaccg cagataaatc ctccagcacc     360
gcctacgtgc agctcaacag cctgacgtct gaagattctg cagtgtattt ctgtacgcgt     420
tccctgaata tggcctactg gggtcaaggt acctcagtca ccgtctccaa gatctctggt     480
ggcggtggct cgggcggtgg tgggtcgggt ggcggcggct cgggtggtgg tgggtcgggc     540
ggcggcggct cgagcgatat tgtgatgtca cagtctccgt cctccctacc ggtgtcagtt     600
ggcgaaaaag ttaccttgag ctgcaaatcc agtcagagcc ttttatatag tggtaatcag     660
aaaaactact ggcctggta ccagcagaaa ccgggtcagt ctccgaaact gctgatttac     720
tgggcatccg ctcgtgaatc tggggtcccg gatcgcttca ccggcagtgg ttctgggacc     780
gatttcaccc tctccatcag cagtgtgaaa accgaagacc tggcagttta ttactgtcag     840
cagtattata gctatccgct cacgttcggt gctgggacca aactggtgct gaagagctct     900
ggctctggtt cggcagaccc ctccaaggac tcgaaggccc aggtctcggc cgccgaggcc     960
ggcatcaccg gcacctggta caaccagctc ggctcgacct catcgtgac cgcgggcgcc    1020
gacggcgccc tgaccggaac ctacgagtcg gccgtcggca acgccgagag ccgctacgtc    1080
ctgaccggtc gttacgacag cgccccggcc accgacggca gcggcaccgc cctcggttgg    1140
acggtggcct ggaagaataa ctaccgcaac gcccactccg cgaccacgtg gagcggccag    1200
tacgtcggcg gcgccgaggc gaggatcaac acccagtggc tgctgacctc cggcaccacc    1260
gaggccaacg cctggaagtc cacgctggtc ggccacgaca ccttcaccaa ggtgaagccg    1320
tccgccgcct ccatcgacgc ggcgaagaag gccggcgtca acaacggcaa cccgctcgac    1380
gccgttcagc agtaaggatc cggctgctaa caaagcccga aggaagctg agttggctgc    1440
tgccaccgct gagcaataac tagcata                                       1467
```

<210> SEQ ID NO 49
<211> LENGTH: 444
<212> TYPE: PRT
<213> ORGANISM: Artificial Sequence
<220> FEATURE:
<223> OTHER INFORMATION: Predicted amino acid sequence for the CC49
single chain antibody-genomic streptavidin fusion sequence

<400> SEQUENCE: 49

```
Met Arg Lys Ile Val Val Ala Ala Ile Ala Val Ser Leu Thr Thr Val
 1               5                  10                  15

Ser Ile Thr Ala Met Ala Gln Val Gln Leu Gln Gln Ser Asp Ala Glu
            20                  25                  30

Leu Val Lys Pro Gly Ala Ser Val Lys Ile Ser Cys Lys Ala Ser Gly
        35                  40                  45

Tyr Thr Phe Thr Asp His Ala Ile His Trp Val Lys Gln Asn Pro Glu
    50                  55                  60

Gln Gly Leu Glu Trp Ile Gly Tyr Phe Ser Pro Gly Asn Asp Asp Phe
65                  70                  75                  80

Lys Tyr Asn Glu Arg Phe Lys Gly Lys Ala Thr Leu Thr Ala Asp Lys
                85                  90                  95

Ser Ser Ser Thr Ala Tyr Val Gln Leu Asn Ser Leu Thr Ser Glu Asp
            100                 105                 110
```

```
Ser Ala Val Tyr Phe Cys Thr Arg Ser Leu Asn Met Ala Tyr Trp Gly
        115                 120                 125

Gln Gly Thr Ser Val Thr Val Ser Lys Ile Ser Gly Gly Gly Gly Ser
    130                 135                 140

Gly Gly Gly Gly Ser Gly Gly Gly Ser Gly Gly Gly Gly Ser Gly
145                 150                 155                 160

Gly Gly Gly Ser Ser Asp Ile Val Met Ser Gln Ser Pro Ser Ser Leu
                165                 170                 175

Pro Val Ser Val Gly Glu Lys Val Thr Leu Ser Cys Lys Ser Ser Gln
            180                 185                 190

Ser Leu Leu Tyr Ser Gly Asn Gln Lys Asn Tyr Leu Ala Trp Tyr Gln
        195                 200                 205

Gln Lys Pro Gly Gln Ser Pro Lys Leu Leu Ile Tyr Trp Ala Ser Ala
    210                 215                 220

Arg Glu Ser Gly Val Pro Asp Arg Phe Thr Gly Ser Gly Ser Gly Thr
225                 230                 235                 240

Asp Phe Thr Leu Ser Ile Ser Ser Val Lys Thr Glu Asp Leu Ala Val
                245                 250                 255

Tyr Tyr Cys Gln Gln Tyr Tyr Ser Tyr Pro Leu Thr Phe Gly Ala Gly
            260                 265                 270

Thr Lys Leu Val Leu Lys Ser Ser Gly Ser Gly Ser Ala Asp Pro Ser
        275                 280                 285

Lys Asp Ser Lys Ala Gln Val Ser Ala Ala Glu Ala Gly Ile Thr Gly
    290                 295                 300

Thr Trp Tyr Asn Gln Leu Gly Ser Thr Phe Ile Val Thr Ala Gly Ala
305                 310                 315                 320

Asp Gly Ala Leu Thr Gly Thr Tyr Glu Ser Ala Val Gly Asn Ala Glu
                325                 330                 335

Ser Arg Tyr Val Leu Thr Gly Arg Tyr Asp Ser Ala Pro Ala Thr Asp
            340                 345                 350

Gly Ser Gly Thr Ala Leu Gly Trp Thr Val Ala Trp Lys Asn Asn Tyr
        355                 360                 365

Arg Asn Ala His Ser Ala Thr Thr Trp Ser Gly Gln Tyr Val Gly Gly
    370                 375                 380

Ala Glu Ala Arg Ile Asn Thr Gln Trp Leu Leu Thr Ser Gly Thr Thr
385                 390                 395                 400

Glu Ala Asn Ala Trp Lys Ser Thr Leu Val Gly His Asp Thr Phe Thr
                405                 410                 415

Lys Val Lys Pro Ser Ala Ala Ser Ile Asp Ala Ala Lys Lys Ala Gly
            420                 425                 430

Val Asn Asn Gly Asn Pro Leu Asp Ala Val Gln Gln
        435                 440

<210> SEQ ID NO 50
<211> LENGTH: 60
<212> TYPE: DNA
<213> ORGANISM: Artificial Sequence
<220> FEATURE:
<223> OTHER INFORMATION: Oligonucleotide primer

<400> SEQUENCE: 50
caggttcagt tgcagcagtc tgatgctgaa ttggtgaaac cgggtgcttc agtgaaaatt      60

<210> SEQ ID NO 51
<211> LENGTH: 60
```

```
<212> TYPE: DNA
<213> ORGANISM: Artificial Sequence
<220> FEATURE:
<223> OTHER INFORMATION: Oligonucleotide primer

<400> SEQUENCE: 51
tgcatgatcg gtgaaggtgt agccagaagc tttgcaggaa attttcactg aagcacccgg    60

<210> SEQ ID NO 52
<211> LENGTH: 60
<212> TYPE: DNA
<213> ORGANISM: Artificial Sequence
<220> FEATURE:
<223> OTHER INFORMATION: Oligonucleotide primer

<400> SEQUENCE: 52
tacaccttca ccgatcatgc aattcattgg gtgaaacaga acccggaaca gggcctggaa    60

<210> SEQ ID NO 53
<211> LENGTH: 60
<212> TYPE: DNA
<213> ORGANISM: Artificial Sequence
<220> FEATURE:
<223> OTHER INFORMATION: Oligonucleotide primer

<400> SEQUENCE: 53
tttgaaatca tcattacccg gagagaaata accaatccat tccaggccct gttccgggtt    60

<210> SEQ ID NO 54
<211> LENGTH: 60
<212> TYPE: DNA
<213> ORGANISM: Artificial Sequence
<220> FEATURE:
<223> OTHER INFORMATION: Oligonucleotide primer

<400> SEQUENCE: 54
ccgggtaatg atgatttcaa atacaatgaa cgtttcaaag gcaaagccac gctgaccgca    60

<210> SEQ ID NO 55
<211> LENGTH: 60
<212> TYPE: DNA
<213> ORGANISM: Artificial Sequence
<220> FEATURE:
<223> OTHER INFORMATION: Oligonucleotide primer

<400> SEQUENCE: 55
gctgttgagc tgcacgtagg cggtgctgga ggatttatct gcggtcagcg tggctttgcc    60

<210> SEQ ID NO 56
<211> LENGTH: 60
<212> TYPE: DNA
<213> ORGANISM: Artificial Sequence
<220> FEATURE:
<223> OTHER INFORMATION: Oligonucleotide primer

<400> SEQUENCE: 56
gcctacgtgc agctcaacag cctgacgtct gaagattctg cagtgtattt ctgtacgcgt    60

<210> SEQ ID NO 57
<211> LENGTH: 60
<212> TYPE: DNA
<213> ORGANISM: Artificial Sequence
<220> FEATURE:
<223> OTHER INFORMATION: Oligonucleotide primer

<400> SEQUENCE: 57
```

```
gactgaggta ccttgacccc agtaggccat attcagggaa cgcgtacaga aatacactgc    60
```

<210> SEQ ID NO 58
<211> LENGTH: 35
<212> TYPE: DNA
<213> ORGANISM: Artificial Sequence
<220> FEATURE:
<223> OTHER INFORMATION: Oligonucleotide primer

<400> SEQUENCE: 58

```
gaattcccat ggctcaggtt cagttgcagc agtct                               35
```

<210> SEQ ID NO 59
<211> LENGTH: 43
<212> TYPE: DNA
<213> ORGANISM: Artificial Sequence
<220> FEATURE:
<223> OTHER INFORMATION: Oligonucleotide primer

<400> SEQUENCE: 59

```
caccagagat cttggagacg gtgactgagg taccttgacc cca                      43
```

<210> SEQ ID NO 60
<211> LENGTH: 60
<212> TYPE: DNA
<213> ORGANISM: Artificial Sequence
<220> FEATURE:
<223> OTHER INFORMATION: Oligonucleotide primer

<400> SEQUENCE: 60

```
gatattgtga tgtcacagtc tccgtcctcc ctaccggtgt cagttggcga aaaagttacc    60
```

<210> SEQ ID NO 61
<211> LENGTH: 60
<212> TYPE: DNA
<213> ORGANISM: Artificial Sequence
<220> FEATURE:
<223> OTHER INFORMATION: Oligonucleotide primer

<400> SEQUENCE: 61

```
accactatat aaaaggctct gactggattt gcagctcaag gtaactttt cgccaactga     60
```

<210> SEQ ID NO 62
<211> LENGTH: 60
<212> TYPE: DNA
<213> ORGANISM: Artificial Sequence
<220> FEATURE:
<223> OTHER INFORMATION: Oligonucleotide primer

<400> SEQUENCE: 62

```
cagagccttt tatatagtgg taatcagaaa aactacttgg cctggtacca gcagaaaccg    60
```

<210> SEQ ID NO 63
<211> LENGTH: 60
<212> TYPE: DNA
<213> ORGANISM: Artificial Sequence
<220> FEATURE:
<223> OTHER INFORMATION: Oligonucleotide primer

<400> SEQUENCE: 63

```
agcggatgcc cagtaaatca gcagtttcgg agactgaccc ggtttctgct ggtaccaggc    60
```

<210> SEQ ID NO 64
<211> LENGTH: 60
<212> TYPE: DNA
<213> ORGANISM: Artificial Sequence

```
<220> FEATURE:
<223> OTHER INFORMATION: Oligonucleotide primer

<400> SEQUENCE: 64
ctgatttact gggcatccgc tcgtgaatct ggggtcccgg atcgcttcac cggcagtggt      60

<210> SEQ ID NO 65
<211> LENGTH: 60
<212> TYPE: DNA
<213> ORGANISM: Artificial Sequence
<220> FEATURE:
<223> OTHER INFORMATION: Oligonucleotide primer

<400> SEQUENCE: 65
tttcacactg ctgatggaga gggtgaaatc ggtcccagaa ccactgccgg tgaagcgatc      60

<210> SEQ ID NO 66
<211> LENGTH: 60
<212> TYPE: DNA
<213> ORGANISM: Artificial Sequence
<220> FEATURE:
<223> OTHER INFORMATION: Oligonucleotide primer

<400> SEQUENCE: 66
ctctccatca gcagtgtgaa aaccgaagac ctggcagttt attactgtca gcagtattat      60

<210> SEQ ID NO 67
<211> LENGTH: 60
<212> TYPE: DNA
<213> ORGANISM: Artificial Sequence
<220> FEATURE:
<223> OTHER INFORMATION: Oligonucleotide primer

<400> SEQUENCE: 67
caccagtttg gtcccagcac cgaacgtgag cggatagcta taatactgct gacagtaata      60

<210> SEQ ID NO 68
<211> LENGTH: 34
<212> TYPE: DNA
<213> ORGANISM: Artificial Sequence
<220> FEATURE:
<223> OTHER INFORMATION: Oligonucleotide primer

<400> SEQUENCE: 68
cggcggctcg agcgatattg tgatgtcaca gtct                                  34

<210> SEQ ID NO 69
<211> LENGTH: 38
<212> TYPE: DNA
<213> ORGANISM: Artificial Sequence
<220> FEATURE:
<223> OTHER INFORMATION: Oligonucleotide primer

<400> SEQUENCE: 69
gagccagagc tcttcagcac cagtttggtc ccagcacc                              38
```

STREPTAVIDIN EXPRESSED GENE FUSIONS AND METHODS OF USE THEREOF

TECHNICAL FIELD

The present invention relates generally to streptavidin expressed gene fusion constructs, and more particularly, to genomic streptavidin expressed gene fusions and methods of using these constructs in diagnostic and therapeutic applications.

BACKGROUND OF THE INVENTION

Streptavidin ("SA") is a 159 amino acid protein produced by *Streptomyces avidinii*, and which specifically binds water-soluble biotin (Chaiet et al., *Arch. Biochem. Biophys.* 106:1–5, 1964). Streptavidin is a nearly neutral 64,000 dalton tetrameric protein. Accordingly, it consists of four identical subunits each having an approximate molecular mass of 16,000 daltons (Sano and Cantor, *Proc. Natl. Acad. Sci. USA* 87:142–146, 1990). Streptavidin shares some common characteristics with avidin, such as molecular weight, subunit composition, and capacity to bind biotin with high affinity ($K_D \approx 10^{-15}$) (Green, *Adv. Prot. Chem.* 29:85–133, 1975). Further, while streptavidin and avidin differ in their amino acid compositions, both have an unusually high content of threonine and tryptophan. In addition, streptavidin differs from avidin in that it is much more specific for biotin at physiological pH, likely due to the absence of carbohydrates on streptavidin. Various comparative properties and isolation of avidin and streptavidin are described by Green et al., *Methods in Enzymology* 184:51–67, 1990 and Bayer et al., *Methods in Enzymology* 184:80–89, 1990.

The streptavidin gene has been cloned and expressed in *E. coli* (Sano and Cantor, *Proc. Natl. Acad. Sci. USA* 87(1): 142–146, 1990; Agarana, et al., *Nucleic Acids Res.* 14(4): 1871–1882, 1986). Fusion constructs of streptavidin, and truncated forms thereof, with various proteins, including single-chain antibodies, have also been expressed in *E. coli* (Sano and Cantor, *Biotechnology* (NY) 9(12):1378–1381, 1991; Sano and Cantor, *Biochem. Biophys. Res. Commun.* 176(2):571–577, 1991; Sano, et al., *Proc. Natl. Acad. Sci. USA* 89(5):1534–1538, 1992; Walsh and Swaisgood, *Biotech. Bioeng.* 44:1348–1354, 1994; Le, et al., *Enzyme Microb. Technol.* 16(6):496–500, 1994; Dubel, et al., *J. Immunol. Methods* 178(2):201–209, 1995; Kipriyanov, et al., *Hum. Antibodies Hybridomas* 6(3):93–101, 1995; Kipriyanov, et al., *Protein Eng.* 9(2):203–211, 1996; Ohno, et al., *Biochem. Mol. Med.* 58(2):227–233, 1996; Ohno and Meruelo, *DNA Cell Biol.* 15(5):401–406, 1996; Pearce, et al. *Biochem. Mol. Biol. Int.* 42(6):1179–1188, 1997; Koo, et al., *Applied Environ. Microbiol.* 64(7):2497–2502, 1998) and in other organisms (Karp, et al., *Biotechniques* 20(3):452–459, 1996). Sano and Cantor (PNAS, supra) found that expression of full-length forms of streptavidin was lethal to *E. coli* host cells and, when capable of being expressed in truncated forms (e.g., under a T7 promoter system), only poor and varied expression was observed and the protein remained in inclusion bodies. However, there are also published reports of the expression of soluble streptavidin in *E. coli* (Gallizia et al., *Protein Expr. Purif.* 14(2):192–196, 1998; Veiko et al., *Bioorg. Khim.* 25(3):184–188, 1999). Those of skill in the art have frequently used "core streptavidin" (residues 14–136), or similar truncated forms, in the preparation of fusion constructs. The basis of the use of core residues 14–136 has been the observation that streptavidin preparations purified from the culture medium of *S. avidinii* have usually undergone proteolysis at both the N- and C-termini to produce this core structure, or functional forms thereof (Argarana et al., supra).

Presently, preparations of streptavidin expressed gene fusions are usually made by expressing a core streptavidin-containing construct in bacteria, wherein inclusion bodies are formed. Such production has several disadvantages, including the rigor and expense of purifying from inclusion bodies, the necessity of using harsh denaturing agents such as guanidine hydrochloride, and the difficulty in scaling up in an economical fashion. To a lesser extent, there has also been reported periplasmic expression of core streptavidin-containing constructs in soluble form (Dubel et al., supra).

Therefore, there exists a need in the art for easy, cost effective, and scaleable methods for the production of streptavidin fusion proteins. Accordingly, the present invention provides several key advantages. For example, in one embodiment, a genomic streptavidin expressed gene fusion is expressed as a soluble protein into the periplasmic space of bacteria and undergoes spontaneous folding. Accordingly, such expression offers the advantage that the periplasm is a low biotin environment and one need not purify and refold the protein under harsh denaturing conditions that may prove fatal to the polypeptide encoded by a heterologous nucleic acid molecule fused to the genomic streptavidin nucleic acid molecule. The present invention fulfills this need, while further providing other related advantages.

SUMMARY OF THE INVENTION

The present invention generally provides expression cassettes and fusion constructs encoded thereby comprising genomic streptavidin. In one aspect, the present invention provides a vector construct for the expression of streptavidin fusion proteins, comprising a first nucleic acid sequence encoding at least 129 amino acids of streptavidin (FIG. 4), or a functional variant thereof, a promoter operatively linked to the first nucleic acid sequence, and a cloning site for, or with, insertion of a second nucleic acid sequence encoding a polypeptide to be fused with streptavidin, interposed between the promoter and the first nucleic acid sequence. Alternatively, the second nucleic acid may encode the streptavidin portion of the construct and the first nucleic acid encodes a polypeptide to be fused with streptavidin.

In certain embodiments, the promoter is inducible or constitutive. In other embodiments, the first nucleic acid sequence encodes at least amino acids 14 to 150, 14 to 151, 14 to 152, 14 to 153, 14 to 154, 14 to 155, 14 to 156, 14 to 157, 14 to 158, or 14 to 159 of streptavidin, FIG. 4, including all integer values within these ranges. In yet other embodiments, the first nucleic acid sequence encodes at least amino acids 5 to 150–159 of FIG. 4 or 1 to 150–159 of FIG. 4, including all integer values within these ranges.

Host cells containing genomic streptavidin expression cassettes are also provided as are fusion proteins expressed by the same. In certain embodiments fusion proteins comprising single chain antibodies are provided. In yet other embodiments the single chain antibodies are directed to a cell surface antigen. In yet other embodiments the single chain antibodies are directed to cell surface antigens, or cell-associated stromal or matrix antigens, including, but not limited to, CD20, CD22, CD45, CD52, CD56, CD57, EGP40 (or EPCAM or KSA), NCAM, CEA, TAG-72, mucins (MUC-1 through MUC-7), β-HCG, EGF receptor, IL-2 receptor, her2/neu, Lewis Y, GD2, GM2, tenascin, sialylated tenascin, somatostatin, activated tumor stromal antigen, or neoangiogenic antigens.

In other aspects of the present invention, methods for targeting a tumor cell are provided, comprising the administration of a fusion protein, said fusion protein comprising at least a first and a second polypeptide joined end to end, wherein said first polypeptide comprises at least 129 amino acids of streptavidin (FIG. 4), or conservatively substituted variants thereof, wherein said second polypeptide is a polypeptide which binds a cell surface protein on a tumor cell, wherein the fusion protein binds the cell surface protein on a tumor cell and wherein the streptavidin portion of the fusion protein is capable of binding biotin. In certain embodiments, the second polypeptide is an antibody or antigen-binding fragment thereof. In yet further embodiments the at least 129 amino acids comprises "core streptavidin".

In other aspects of the present invention, pharmaceutical compositions, comprising genomic streptavidin fusion constructs are provided.

These and other aspects of the present invention will become evident upon reference to the following detailed description and attached drawings.

BRIEF DESCRIPTION OF THE DRAWINGS

FIG. 4 is the sequence of genomic streptavidin (SEQ ID NO: 1) including the signal sequence and predicted amino acid sequence (SEQ ID NO: 2).

FIGS. 10A–10B represent the determined nucleic acid sequence (SEQ ID NO: 3) and predicted amino acid sequence (SEQ ID NO: 4) for the huNR-LU-10 single chain antibody-genomic streptavidin fusion. The streptavidin regulatory region, signal sequence, and coding sequence are noted as are the various linkers and light and heavy chains of the single chain antibody.

FIGS. 11A and 11B are the determined nucleic acid (SEQ ID NO: 5) and predicted amino acid sequences (SEQ ID NO: 6) of a B9E9 scFvSA fusion construct, with the pKOD linker between $V_L$ and $V_H$. Linkers are boxed and the orientation is $V_L$-linker-$V_H$-linker-Streptavidin.

FIGS. 11C–11D are an expression cassette comprising the nucleic acid sequences (SEQ ID NO: 7) and predicted amino acid sequences (SEQ ID NO: 8) of a B9E9 scFvSA fusion construct encoding $V_H$-linker-$V_L$-linker-Streptavidin.

FIG. 22 represents the determined nucleic acid sequence (SEQ ID NO: 48) and predicted amino acid sequence (SEQ ID NO: 49) for the CC49 single chain antibody-genomic streptavidin fusion. The streptavidin regulatory region, signal sequence, and coding sequence are noted as are the various linkers and light and heavy chains of the single chain antibody.

DETAILED DESCRIPTION OF THE INVENTION

Prior to setting forth the invention, it may be helpful to an understanding thereof to set forth definitions of certain terms that will be used hereinafter.

Figure 3:
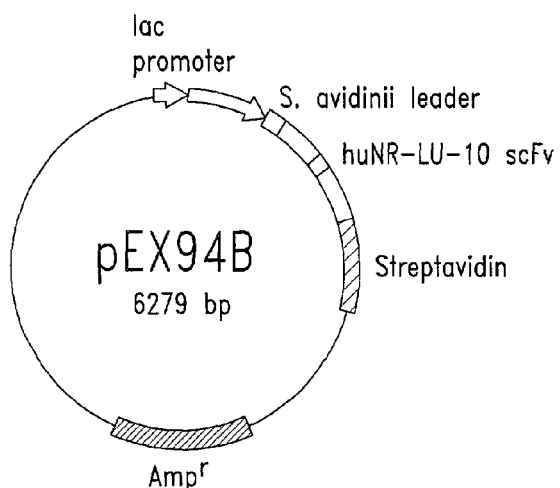
FIG. 3 is a schematic representation of the pEX94B expression vector containing a single chain antibody (huNR-LU-10)-genomic streptavidin fusion construct.
Figure 5:
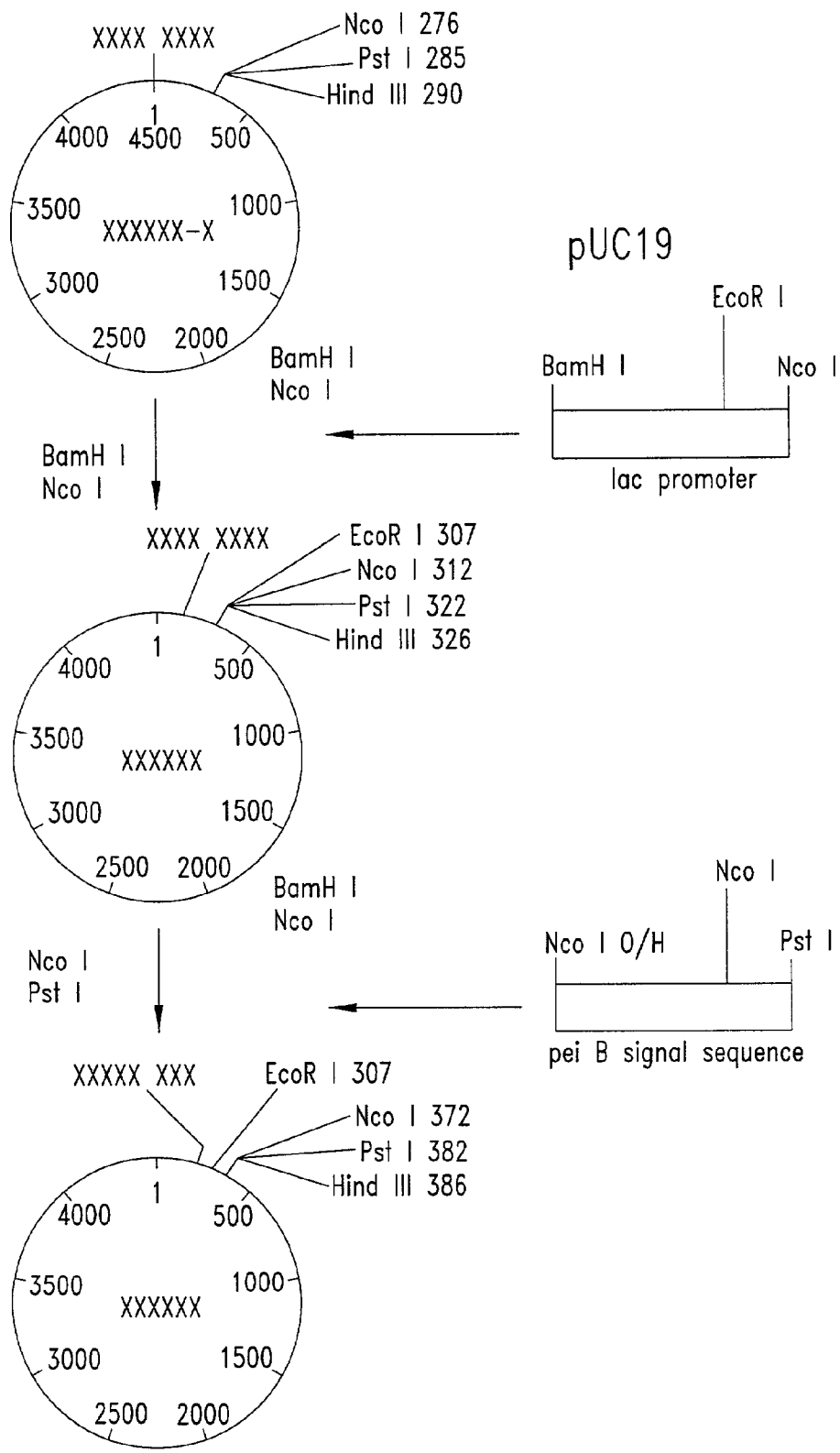
FIG. 5 is a schematic representation of the construction of the pKKlac/pelB vector.

"Core streptavidin," as used herein, refers to a streptavidin molecule consisting of the central amino acid residues 14–136 of streptavidin of FIG. 4 and also of FIG. 3 of U.S. Pat. No. 4,839,293 and deposited at ATCC number X03591, as well as that disclosed by U.S. Pat. Nos. 5,272,254 and 5,168,049 (all incorporated herein by reference).

"Genomic streptavidin," as used herein, refers to a sequence comprising at least 129 residues of the sequence set forth in FIG. 4, wherein the at least 129 residues contains the core streptavidin sequence therein. Accordingly, genomic streptavidin refers to core streptavidin molecules comprising N-terminal, C-terminal, or both N- and C-terminal extensions. The N- and C-terminal extensions may comprise any number of amino acids selected from residues 1 to 13, 137 to 159 and all integer values between these numbers, and in some cases any number of the amino acids −1 to −24 of FIG. 4, such as −5 to −24 and any integer values therebetween.

The genomic streptavidin molecules of the subject invention also include variants (including alleles) of the native protein sequence. Briefly, such variants may result from natural polymorphisms or may be synthesized by recombinant DNA methodology, and differ from wild-type protein by one or more amino acid substitutions, insertions, deletions, or the like. Variants generally have at least 75% nucleotide identity to native sequence, preferably at least 80%–85%, and most preferably at least 90% nucleotide identity. Typically, when engineered, amino acid substitutions will be conservative, i.e., substitution of amino acids within groups of polar, non-polar, aromatic, charged, etc. amino acids. With respect to homology to the native sequence, variants should preferably have at least 90% amino acid sequence identity, and within certain embodiments, greater than 92%, 95%, or 97% identity. Such amino acid sequence identity may be determined by standard methodologies, including use of the National Center for Biotechnology Information BLAST search methodology.

The identity methodologies most preferred are those described in U.S. Pat. No. 5,691,179 and Altschul et al., *Nucleic Acids Res.* 25:3389–3402, 1997.

As will be appreciated by those skilled in the art, a nucleotide sequence and the encoded genomic streptavidin or variant thereof may differ from known native sequence, due to codon degeneracies, nucleotide polymorphisms, or amino acid differences. In certain embodiments, variants will preferably hybridize to the native nucleotide sequence at conditions of normal stringency, which is approximately 25–30° C. below Tm of the native duplex (e.g., 5× SSPE, 0.5% SDS, 5× Denhardt's solution, 50% formamide, at 42° C. or equivalent conditions; see generally, Sambrook et al., *Molecular Cloning: A Laboratory Manual*, 2nd ed., Cold Spring Harbor Press, 1989; Ausubel et al., *Current Protocols in Molecular Biology*, Greene Publishing, 1995). By way of comparison, low stringency hybridizations utilize conditions approximately 40° C. below Tm, and high stringency hybridizations utilize conditions approximately 10° C. below Tm.

A "polypeptide," as used herein, refers to a series of amino acids of five or more.

An "isolated nucleic acid molecule" refers to a polynucleotide molecule in the form of a separate fragment or as a component of a larger nucleic acid construct, that has been separated from its source cell (including the chromosome it normally resides in) at least once, and preferably in a substantially pure form. Nucleic acid molecules may be comprised of a wide variety of nucleotides, including DNA, RNA, nucleotide analogues, or combination thereof.

The term "heterologous nucleic acid sequence", as used herein, refers to at least one structural gene operably associated with a regulatory sequence such as a promoter. The nucleic acid sequence originates in a foreign species, or, in the same species if substantially modified from its original form. For example, the term "heterologous nucleic acid sequence" includes a nucleic acid originating in the same species, where such sequence is operably associated with a promoter that differs from the natural or wild-type promoter.

An "antibody," as used herein, includes both polyclonal and monoclonal antibodies; humanized; Primatized® (ie., Macaque variable region fused to human constant domains; murine; mouse-human; human-primate; mouse-primate; and chimeric; and may be an intact molecule, a fragment thereof (such as scFv, Fv, Fd, Fab, Fab' and F(ab)'$_2$ fragments), or multimers or aggregates of intact molecules and/or fragments; and may occur in nature or be produced, e.g., by immunization, synthesis or genetic engineering; an "antibody fragment," as used herein, refers to fragments, derived from or related to an antibody, which bind antigen and which in some embodiments may be derivatized to exhibit structural features that facilitate clearance and uptake, e.g., by the incorporation of galactose residues. This includes, e.g., F(ab), F(ab)'$_2$, scFv, light chain variable region ($V_L$), heavy chain variable region ($V_H$), and combinations thereof.

A molecule/polypeptide is said to "specifically bind" to a particular polypeptide (e.g., antibody-ligand binding) if it binds at a detectable level with the particular polypeptide, but does not bind significantly with another polypeptide containing an unrelated sequence. Such that one of skill in the art of what recognize such as not substantially cross-reactive with another polypeptide/molecule. An "unrelated sequence," as used herein, refers to a sequence that is at most 10% identical to a reference sequence. In certain embodiments the binding affinity for the target will be at least $10^{-6}$ M, $10^{-7}$M, or at least $10^{-8}$M.

The term "protein," as used herein, includes proteins, polypeptides and peptides; and may be an intact molecule, a fragment thereof, or multimers or aggregates of intact molecules and/or fragments; and may occur in nature or be produced, e.g., by synthesis (including chemical and/or enzymatic) or genetic engineering.

A. Streptavidin Genes and Gene Products

1. Streptavidin Nucleic Acid Molecules and Variants Thereof

The present invention provides streptavidin fusion constructs that include streptavidin nucleic acid molecules of various lengths, which, in certain embodiments, are constructed from full-length genomic streptavidin nucleic acid molecules available in the art and specifically described in U.S. Pat. Nos. 4,839,293; 5,272,254, 5,168,049 and ATCC Accession number X03591.

Variants of streptavidin nucleic acid molecules, provided herein, may be engineered from natural variants (e.g., polymorphisms, splice variants, mutants), synthesized or constructed. Many methods have been developed for generating mutants (see, generally, Sambrook et al., *Molecular Cloning: A Laboratory Manual,* Cold Spring Harbor Press, 1989, and Ausubel, et al. *Current Protocols in Molecular Biology,* Greene Publishing Associates and Wiley-Interscience, New York, 1995). Briefly, preferred methods for generating nucleotide substitutions utilize an oligonucleotide that spans the base or bases to be mutated and contains the mutated base or bases. The oligonucleotide is hybridized to complementary single stranded nucleic acid and second strand synthesis is primed from the oligonucleotide. The double-stranded nucleic acid is prepared for transformation into host cells, typically *E. coli,* but alternatively, other prokaryotes, yeast or other eukaryotes. Standard methods of screening and isolation and sequencing of DNA were used to identify mutant sequences.

Similarly, deletions and/or insertions of the streptavidin nucleic acid molecule may be constructed by any of a variety of known methods as discussed, supra. For example, the nucleic acid molecule can be digested with restriction enzymes and religated, thereby deleting or religating a sequence with additional sequences (e.g., linkers), such that an insertion or large substitution is made. Other means of generating variant sequences may be employed using methods known in the art, for example those described in Sambrook et al., supra; Ausubel et al., supra. Verification of variant sequences is typically accomplished by restriction enzyme mapping, sequence analysis, or probe hybridization. In certain aspects, variants of streptavidin nucleic acid molecules whose encoded product is capable of binding biotin, are useful in the context of the subject invention. In other aspects, the ability of the variant streptavidin to bind biotin may be increased, decreased or substantially similar to that of native streptavidin. In yet other embodiments, the ability to bind biotin is not required, provided that the variant form retains the ability to self-assemble into a typical tetrameric structure similar to that of native streptavidin. Such tetrameric structures have a variety of uses such as the formation of tetravalent antibodies when fused to sequences encoding an antibody or fragment thereof.

2. Genomic Streptavidin and Expression Cassettes Containing the Same

A genomic streptavidin fusion construct expression cassette of the present invention may be generated by utilizing the full gene sequence of the streptavidin gene, or variant thereof. In certain embodiments, the expression cassette contains a nucleic acid sequence encoding at least 129 contiguous amino acids of and including at least residues 14–136 of FIG. 4 or functional variants thereof. In various other embodiments, the nucleic acid sequence encodes at least amino acid residues 14 to 140 of FIG. 4. In a further embodiment, the nucleic acid sequence encodes at least amino acids 14 to 150, 14 to 151, 14 to 152, 14 to 153, 14 to 154, 14 to 155, 14 to 156, 14 to 157, 14 to 158, or 14 to 159 of streptavidin, FIG. 4. In yet other embodiments, the nucleic acid sequence encodes at least amino acids 10 to 150–158 of FIG. 4, or 5 to 150–158 of FIG. 4 or 1 to 150–158 of FIG. 4. In yet other embodiments, the nucleic acid sequence encodes at least amino acid residues 1 to 159 of FIG. 4. In still yet other embodiments, the expression cassette comprises a nucleic acid sequence that encodes genomic streptavidin and at least 10 contiguous amino acids of residues selected from those set forth −1 to −24 of FIG. 4, such as −1 to −10, −1 to −15, −1 to −20, −5 to −15, −5 to −20, −5 to −24, or any integer value between these numbers.

As noted above, the genomic streptavidin encoding nucleic acid molecules of the subject invention may be constructed from available streptavidin sequences by a variety of methods known in the art. A preferred method is amplification (e.g., polymerase chain reaction (PCR)) to selectively amplify the individual regions and place these in cloning vectors such as pCR2.1 (Invitrogen). Moreover, such PCR reactions can be performed in a variety of ways such that the primers used for amplification contain specific restriction endonuclease sites to facilitate insertion into a vector.

Further, a variety of other methodologies besides PCR may be used to attain the desired construct For example, one skilled in the art may employ isothermal methods to amplify the nucleotide sequence of interest, using existing restriction endonuclease sites present in the nucleotide sequence to excise and insert sequences, or by the introduction of distinct restriction endonuclease sites by site-directed mutagenesis followed by excision and insertion. These and other methods are described in Sambrook et al., supra; Ausubel, et al., supra. Briefly, one methodology is to generate single-stranded streptavidin encoding DNA, followed by annealing a primer, which is complementary except for the desired alteration (e.g., a small insertion, deletion, or mutation such that a unique restriction site is created between the domains). Bacterial cells are transformed and screened for those cells which contain the desired construct. This construct is then digested to liberate the desired sequences, which can then be purified and religated into the appropriate orientation.

One of skill in the art would recognize that the absolute length of the genomic streptavidin is only a secondary consideration when designing an expression cassette, as compared to utilizing a form which is capable of binding biotin, if so desired, and capable of expressing into the periplasmic space of a bacterial host. In certain embodiments, the expressed genomic streptavidin polypeptide fusion is present within the periplasm in a statistically significant amount as compared to heterologous fusions to core streptavidin. For any particular fusion construct of the present invention, increased localization to the periplasmic space refers in certain embodiments to the percentage of total expressed polypeptide in the periplasmic space that is at least two-fold greater than the percentage of total expressed core fusion proteins in the periplasmic space. Further, such constructs can be readily tested for their ability to bind biotin and maintain solubility in the periplasmic space by assays known in the art and those described herein. Accordingly, experiments such as, measuring biotin binding capacity and biotin dissociation rate are well known in the art and applicable in this regard. Briefly, such constructs can be tested for their ability to bind biotin by a variety of means, including labeling the fusion protein with a subsaturating level of radiolabeled biotin, then adding a 100-fold saturating level of biocytin to initiate dissociation. The free radiolabeled biotin is measured at timed intervals.

B. Vectors, Host Cells and Methods of Expressing and Producing Protein

The expression cassette of the present invention need not necessarily contain a promoter, but upon insertion into a vector system the sequence contained within the cassette must be capable of being expressed once associated with a promoter or other regulatory sequences. In one embodiment, the expression cassette itself comprises a promoter. Further, the cassette preferably contains a cloning site for the insertion of a heterologous nucleic acid sequence to be fused/ linked to the genomic streptavidin encoding sequence. One exemplary cassette is set forth in FIG. 1. However, it should be noted that the cloning site need not be 5' of the genomic streptavidin sequence, but could be placed 3' of the streptavidin sequence. Thus, an encoded fusion protein could contain the genomic streptavidin polypeptide either N- or C-terminal to the encoded polypeptide fused thereto. Further, while it should be noted that a variety of other nucleic acid sequences can be linked to the genomic streptavidin encoding sequence, in one embodiment the sequence encodes an antibody fragment, and in certain embodiments a single chain antibody (scFv).

Figure 1:
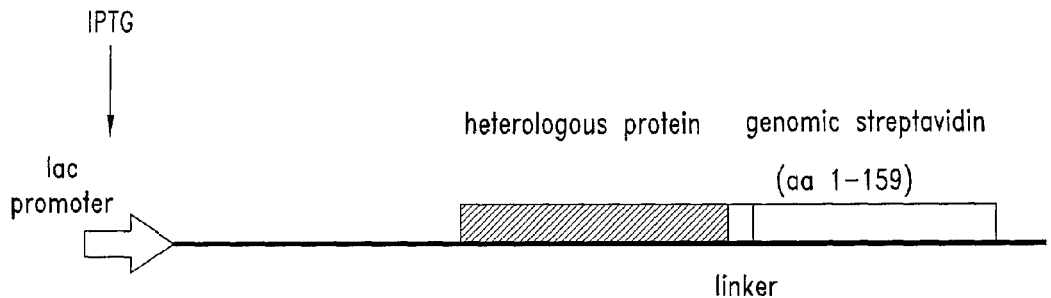
FIG. 1 is a schematic representation of a heterologous protein-genomic streptavidin expressed gene construct.
Figure 2:
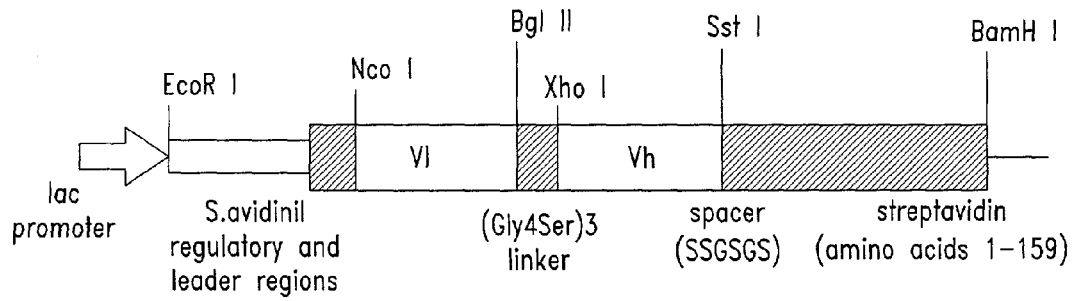
FIG. 2 is a schematic representation of a single chain antibody-genomic streptavidin fusion construct. Shown is the scFV gene consisting of variable regions of the light ($V_L$) and heavy ($V_H$) chains separated b the linker $(Gly_4Ser)_3$ (SEQ ID NO:10). Streptavidin (amino acids 25–183 of SEQ ID NO:2) is joined to the 3' terminus of the scFV gene separated by a second linker, SSGSGS (SEQ ID NO:70).

In addition to a cloning site, the cassette may include a linker molecule. Linker molecules are typically utilized within the context of fusion proteins and are well known in the art. As exemplified in FIG. 2, linkers are typically utilized to separate the genomic streptavidin sequence from the other sequences linked thereto and to separate the $V_H$ and the $V_L$ of the scFv. The linking sequence can encode a short peptide or can encode a longer polypeptide. Preferable linker sequences encode at least two amino acids, but may encode as many amino acids as desired as long as functional activity is retained. Such retained activity may include the ability to bind biotin, increased expression into the periplasmic space, or the ability of a fused antibody, antibody derived domain or fragment, to specifically bind at antigen. In the various embodiments, the linker sequence encodes 5, 6, 7, 8, 9, 10, 11, 12, 13, 14, 15, 16, 17, 18, 19, 20, 21, 22, 23, 24, 25, and 35 amino acids. In certain embodiments an encoded linker may be a standard linker such as $(Gly_4Ser)_X$ (SEQ ID NO: 47) where x may be any integer, but is preferably 1 to 10. The length and composition can be empirically determined to give the optimum expression and biochemical characteristics. For example, the composition of the linker can be changed to raise or lower the isoelectric point of the molecule. Additionally, one of ordinary skill in the art will appreciate that the length of linker between variable light and heavy chains need be at least long enough to facilitate association between the two domains, while the linker between streptavidin and the antibody fragment may vary from zero amino acids to 100 or more as long as functionality is maintained. Accordingly, the linker between the light and heavy chain is typically greater than five amino acids, and preferably greater than ten, and more preferably greater than fifteen amino acids in length.

The expression cassette may be used in a vector to direct expression in a variety of host organisms. In certain embodiments, the genomic streptavidin expressed gene fusion is produced in bacteria, such as *E. coli*, or mammalian cells (e.g., CHO and COS-7), for which many expression vectors have been developed and are available. Other suitable host organisms include other bacterial species, and eukaryotes, such as yeast (e.g., *Saccharomyces cerevisiae*), plants, and insect cells (e.g., Sf9).

In one embodiment, a DNA sequence encoding a genomic streptavidin fusion protein is introduced into an expression vector appropriate for the host cell. As discussed above, the sequence may contain alternative codons for each amino acid with multiple codons. The alternative codons can be chosen as "optimal" for the host species. Restriction sites are typically incorporated into the primer sequences and are chosen with regard to the cloning site of the vector. If necessary, translational initiation and termination codons can be engineered into the primer sequences.

At a minimum, the vector will contain a promoter sequence. As used herein, a "promoter" refers to a nucleotide sequence that contains elements that direct the transcription of a linked gene. At a minimum, a promoter contains an RNA polymerase binding site. More typically, in eukaryotes, promoter sequences contain binding sites for other transcriptional factors that control the rate and timing of gene expression. Such sites include TATA box, CAAT box, POU box, AP1 binding site, and the like. Promoter regions may also contain enhancer elements. When a promoter is linked to a gene so as to enable transcription of the gene, it is "operatively linked."

The expression vectors used herein include a promoter designed for expression of the proteins in a host cell (e.g., bacterial). Suitable promoters are widely available and are well known in the art. Inducible or constitutive promoters are preferred. Such promoters for expression in bacteria include promoters from the T7 phage and other phages, such as T3, T5, and SP6, and the trp, lpp, and lac operons. Hybrid promoters (see, U.S. Pat. No. 4,551,433), such as tac and trc, may also be used. Promoters for expression in eukaryotic cells include the P10 or polyhedron gene promoter of baculovirus/insect cell expression systems (see, e.g., U.S. Pat. Nos. 5,243,041, 5,242,687, 5,266,317, 4,745,051, and 5,169,784), MMTV LTR, CMV IE promoter, RSV LTR, SV40, metallothionein promoter (see, e.g., U.S. Pat. No. 4,870,009), ecdysone response element system, tetracycline-reversible silencing system (tet-on, tet-off), and the like.

The promoter controlling transcription of the genomic streptavidin fusion construct may itself be controlled by a repressor. In some systems, the promoter can be derepressed by altering the physiological conditions of the cell, for example, by the addition of a molecule that competitively binds the repressor, or by altering the temperature of the growth media. Preferred repressor proteins include, the *E. coli* lacI repressor responsive to IPTG induction, the temperature sensitive λcI857 repressor, and the like.

Other regulatory sequences may be included. Such sequences include a transcription termination sequence, secretion signal sequence (e.g., see FIGS. 10 and 22 as well as nucleotides 480–551 of FIG. 2B of U.S. Pat. No. 5,272, 254), ribosome binding sites, origin of replication, selectable marker, and the like. The regulatory sequences are operationally associated with one another to allow transcription, translation, or to facilitate secretion. The regulatory sequences of the present invention also include the upstream region of the streptavidin gene as described in U.S. Pat. No. 5,272,254 (e.g., nucleic acid residues 174–551 depicted in FIGS. 2A–2B of U.S. Pat. No. 5,272,254). Accordingly, an upstream sequence of 100 to 300 base pairs may be utilized in expression constructs to facilitate secretion and/or expression. Such an upstream untranslated region is depicted in U.S. Pat. No. 5,272,254 FIGS. 2A and 2B as nucleotides 174–479. In preferred embodiments nucleic acid residues 408–479 of those described above are utilized in the expression construct.

In other optional embodiments, the vector also includes a transcription termination sequence. A "transcription terminator region" has either a sequence that provides a signal that terminates transcription by the polymerase that recognizes the selected promoter and/or a signal sequence for polyadenylation.

In one aspect, the vector is capable of replication in the host cells. Thus, when the host cell is a bacterium, the vector preferably contains a bacterial origin of replication. Bacterial origins of replication include the f1-ori and col E1 origins of replication, especially the ori derived from pUC plasmids. In yeast, ARS or CEN sequences can be used to assure replication. A well-used system in mammalian cells is SV40 ori.

The plasmids also preferably include at least one selectable marker that is functional in the host. A selectable marker gene includes any gene that confers a phenotype on the host that allows transformed cells to be identified and selectively grown. Suitable selectable marker genes for bacterial hosts include the ampicillin resistance gene ($Amp^r$), tetracycline resistance gene ($Tc^r$) and the kanamycin resistance gene ($Kan^r$). The ampicillin resistance and kanamycin resistance genes are presently preferred. Suitable markers for eukaryotes usually require a complementary deficiency in the host (e.g., thymidine kinase (tk) in tk-hosts). However, drug markers are also available (e.g., G418 resistance and hygromycin resistance).

The nucleotide sequence encoding the genomic streptavidin fusion protein may also include a secretion signal (e.g., a portion of the leader sequence, the leader sequence being the upstream region of a gene including a portion of a secretion signal), whereby the resulting peptide is a precursor protein processed and secreted. The resulting processed protein may be recovered from the periplasmic space or the fermentation medium. Secretion signals suitable for use are widely available and are well known in the art (von Heijne,

*J. Mol. Biol.* 184:99–105, 1985; von Heijne, *Eur. J. Biochem.* 133:17–21, 1983). Prokaryotic and eukaryotic secretion signals that are functional in *E. coli* (or other host) may be employed. The presently preferred secretion signals include, but are not limited to, those encoded by the following bacterial genes: streptavidin, pelB (Lei et al., *J. Bacteriol.* 169:4379, 1987), phoA, ompA, ompT, ompF, ompC, beta-lactamase, and alkaline phosphatase.

Other components which increase expression may also be included either within the vector directing expression of the streptavidin fusion or on a separate vector. Such components include, for example, bacterial chaperone proteins such as SicA, GroEL, GroE, DnaK, CesT, SecB, FkpA, SkpA, etc.

One skilled in the art will appreciate that there are a wide variety of vectors which are suitable for expression in bacterial cells and which are readily obtainable. Vectors such as the pET series (Novagen, Madison, Wis.), the tac and trc series (Pharmacia, Uppsala, Sweden), pTTQ 18 (Amersham International plc, England), pACYC 177, pGEX series, and the like are suitable for expression of a genomic streptavidin fusion protein. The choice of a host for the expression of a genomic streptavidin fusion protein is dictated in part by the vector. Commercially available vectors are paired with suitable hosts.

A wide variety of suitable vectors for expression in eukaryotic cells are also available. Such vectors include pCMVLacI, pXT1 (Stratagene Cloning Systems, La Jolla, Calif.); pcDNA series, pREP series, pEBVHis, pDisplay (Invitrogen, Carlsbad, Calif.). In certain embodiments, the genomic streptavidin fusion protein encoding nucleic acid molecule is cloned into a gene targeting vector, such as pMC1neo, a pOG series vector (Stratagene Cloning Systems).

As noted above, preferred host cells include, by way of example, bacteria such as *Escherichia coli*; mammalian cells such as Chinese Hamster Ovary (CHO) cells, COS cells, myeloma cells; yeast cells such as *Saccharomyces cerevisiae*; insect cells such as *Spodoptera frugiperda*; plant cells such as maize, among other host cells.

Insect cells are capable of high expression of recombinant proteins. In this regard, baculovirus vectors, such as pBlueBac (see, e.g., U.S. Pat. Nos. 5,278,050, 5,244,805, 5,243,041, 5,242,687, 5,266,317, 4,745,051 and 5,169,784; available from Invitrogen, San Diego, Calif.) may be used for expression in insect cells, such as *Spodoptera frugiperda* Sf9 cells (see, U.S. Pat. No. 4,745,051). Expression in insect cells or insects is preferably effected using a recombinant baculovirus vector capable of expressing heterologous proteins under the transcriptional control of a baculovirus polyhedrin promoter. (e.g., U.S. Pat. No. 4,745,051 relating to baculovirus/insect cell expression system). Polyhedrin is a highly expressed protein, therefore its promoter provides for efficient heterologous protein production. The preferred baculovirus is *Autographa californica* (ACMNPV). Suitable baculovirus vectors are commercially available from Invitrogen.

Also, the fusion construct of the present invention may be expressed in transgenic animals. For example, the genomic streptavidin containing expression cassette may be operatively linked to a promoter that is specifically activated in mammary tissue such as a milk-specific promoter. Such methods are described in U.S. Pat. Nos. 4,873,316 and 5,304,498.

The genomic streptavidin gene fusion may also be expressed in plants, e.g., transgenic plants, plant tissues, plant seeds and plant cells. Such methods are described, e.g., in U.S. Pat. No. 5,202,422.

Regardless of the particular system chosen, the design of systems suitable for expression of recombinant proteins is well known and within the purview of one of ordinary skill in the art, as evidenced by the above-identified references relating to expression of recombinant fusion proteins.

Accordingly, as is evidenced by the text and examples herein, expression of fusion proteins within the context of a genomic streptavidin expressed gene fusion construct provides several key advantages. For example, in one embodiment, the genomic streptavidin fusion protein is expressed as soluble protein into the periplasmic space of bacteria (e.g., XL-1 blue, Stratagene) and undergoes spontaneous folding. Accordingly, such expression offers the advantage that the periplasm is a low biotin, oxidizing environment and produces a soluble, functional molecule. This avoids having to purify and refold the protein under harsh denaturing conditions, which may prove fatal to the polypeptide encoded by the heterologous nucleic acid molecule.

The genomic streptavidin expressed gene fusion may be isolated by a variety of methods known to those skilled in the art. However, preferably the purification method takes advantage of the presence of a functional streptavidin molecule, by utilizing its high affinity binding to aid in purification. Accordingly, preferred purification methods are by the use of iminobiotin immobilized on a solid surface.

C. Antibodies as Fusion Components

While a broad variety of genomic streptavidin expressed gene fusion molecules may be designed by the methods described herein, a particularly useful fusion protein is that of an antibody and genomic streptavidin, in particular an antibody-genomic streptavidin expressed gene fusion (AbSA). In preferred embodiments the expression construct encodes an Fv or scFv portion of an antibody. In a further preferred embodiment the construct encodes a Fab fragment or functional derivative thereof, to which streptavidin may be linked via a terminus of either the heavy chain portion or light chain portion of the molecule. Accordingly, DNA encoding the Fv regions of interest may be prepared by any suitable method, including, for example, amplification techniques such as polymerase chain reaction from cDNA of a hybridoma, using degenerate oligonucleotides, ligase chain reaction (LCR) (see Wu and Wallace, *Genomics,* 4:560, 1989, Landegren et al., *Science,* 241:1077, 1988 and Barringer et al., *Gene,* 89:117, 1990), transcription-based amplification (see Kwoh et al., *Proc. Natl. Acad. Sci. USA,* 86:1173, 1989), and self-sustained sequence replication (see Guatelli et al., *Proc. Natl. Acad. Sci. USA,* 87:1874, 1990), cloning and restriction of appropriate sequences or direct chemical synthesis by methods such as the phosphotriester method of Narang et al., *Meth. Enzymol.* 68:90–99, 1979; the phosphodiester method of Brown et al., *Meth. Enzymol.* 68:109–151, 1979; the diethylphosphoramidite method of Beaucage et al., *Tetra. Lett.,* 22:1859–1862, 1981; and the solid support method of U.S. Pat. No. 4,458,066, as well as U.S. Pat. Nos. 5,608,039 and 5,840,300, as well as PCT Application No. WO 98/41641. DNA encoding regions of interest, for example, Fab or scFv, may also be isolated from phage display libraries.

One of ordinary skill in the art would readily recognize that given the disclosure provided herein, any number of binding pair members may be utilized and thus would not be limited to streptavidin/biotin binding. In this regard, antibody/epitope pairs or any ligand/anti-ligand pair may be utilized. One of ordinary skill in the art would also appreciate that the present disclosure provides a general method for the preparation of tetravalent antibodies. Since the avidity of an antibody for its cognate antigen is generally a function of its valency, there are many applications in which a tetravalent antibody would be preferable to a divalent antibody. Such applications include, but are not limited to, immunoassays, immunotherapy, immunoaffinity chromatography, etc.

Chemical synthesis may also be utilized to produce a single stranded oligonucleotide. This may be converted into double stranded DNA by hybridization with a complementary sequence, or by polymerization with a DNA polymerase using the single strand as a template. While it is possible to chemically synthesize an entire single chain Fv region, it is preferable to synthesize a number of shorter sequences (about 100 to 150 bases) that are later ligated together.

Alternatively, subsequences may be cloned and the appropriate subsequences cleaved using appropriate restriction enzymes. The fragments may then be ligated to produce the desired DNA sequence.

Once the variable light ($V_L$) and heavy chain ($V_H$) DNA is obtained, the sequences may be ligated together, either directly or through a DNA sequence encoding a peptide linker, using techniques well known to those of skill in the art. In a preferred embodiment, heavy and light chain regions are connected by a flexible polypeptide linker (e.g., $(Gly_4Ser)_x$ [SEQ ID NO:47, where x may be any integer, but is preferably 1 to 10, described supra], or the pKOD sequence, or others, such as those provided, infra) which starts at the carboxyl end of the light chain Fv domain and ends at the amino terminus of the heavy chain Fv domain, or vice versa, as the order of the Fv domains can be either light-heavy or heavy-light. The entire sequence encodes the Fv domain in the form of a single-chain antigen binding protein.

A variety of methods exist for the recombinant expression of immunoglobulins, the following references are representative of methods and host systems suitable for expression of recombinant immunoglobulins and fusion proteins in general: Weidle et al., *Gene* 51:21–29, 1987; Dorai et al., *J. Immunol.* 13(12):4232–4241, 1987; De Waele et al., *Eur. J. Biochem.* 176:287–295, 1988; Colcher et al., *Cancer Res.* 49:1738–1745, 1989; Wood et al., *J. Immunol.* 145(a): 3011–3016, 1990; Bulens et al., *Eur. J. Biochem.* 195: 235–242 1991; Beggington et al., *Biol. Technology* 10:169, 1992; King et al., *Biochem. J.* 281:317–323, 1992; Page et al., *Biol. Technology* 9:64, 1991; King et al., *Biochem. J.* 290:723–729, 1993; Chaudary et al., *Nature* 339:394–397, 1989; Jones et al., *Nature* 321:522–525, 1986; Morrison and Oi, *Adv. Immunol.* 44:65–92, 1988; Benhar et al, *Proc. Natl. Acad. Sci. USA* 91:12051–12055, 1994; Singer et al., *J. Immunol.* 150:2844–2857, 1993; Cooto et al., *Hybridoma* 13(3):215–219, 1994; Queen et al., *Proc. Natl. Acad. Sci. USA* 86:10029–10033, 1989; Caron et al., *Cancer Res.* 32:6761–6767, 1992; Dubel et al., *J. Immunol. Methods* 178:201–209, 1995; Batra et al. *J. Biol. Chem.* 265:15198–15202, 1990; Batra et al., *Proc. Natl. Acad. Sci. USA*, 86:8545–8549, 1989; Chaudhary et al., *Proc. Natl. Acad. Sci. USA*, 87:1066–1070, 1990, several of which describe the preparation of various single chain antibody expressed gene fusions.

Accordingly, once a DNA sequence has been identified that encodes an Fv region which when expressed shows specific binding activity, fusion proteins comprising that Fv region may be prepared by methods known to one of skill in the art. The Fv region may be fused to genomic streptavidin directly in the expression cassette of the present invention or, alternatively may be joined directly to genomic streptavidin through a peptide or polypeptide linker, thereby forming a linked product. The linker may be present simply to provide space between the Fv and the fused genomic streptavidin or to facilitate mobility between these regions to enable them to each attain their optimum conformation. The genomic streptavidin-antibody expression cassette, typically, comprises a single vector which provides for the expression of both heavy and light variable sequences fused by an appropriate linker as well as a linker fusing the light and heavy chains with genomic streptavidin, thereby encoding a single chain antibody:genomic streptavidin (scFvSA) conjugate. In one embodiment the linker connecting the variable light and heavy chains is of sufficient length or side group selection to allow for flexibility. In one embodiment the linker is a standard linker such as $(Gly_4Ser)_x$ [SEQ ID NO:47, where x may be any integer, but is preferably 1 to 10], described supra, while in another embodiment the linker is the pKOD linker (GlyLeuGluGlySerProGluAlaGlyLeuSerProAspAlaGlySerGlySer) (SEQ ID NO: 9). It should be understood that a variety of linkers may be used, but in some embodiments it may be preferred that the linker separating the light and heavy antibody chains should allow flexibility and the linker attaching the scFv to the genomic streptavidin sequence can be fairly rigid or fairly flexible. Further, in addition to linkers, additional amino acids may be encoded by the addition of restriction sites to facilitate linker insertion and related recombinant DNA manipulation, as such these amino acids while not necessarily intended to be linkers may or may not be included within the constructs described herein, depending on the construction method utilized.

Exemplary linkers are known by those of skill in the art. For example, Fv portions of the heavy and light chain of antibodies held together by a polypeptide linker can have the same binding properties as their full length two chain counterparts (Bird et al., *Science*, 242:423–26, 1988 and Huston et al., *Proc. Natl. Acad. Sci. USA*, 85:5879–83, 1988). It has also been shown that, in some cases, fusion proteins composed of single chain antibodies linked to toxins may retain the binding capacity of the single chain antibody as well as the activity of the toxin (Chaudary et al., *Nature*, 339: 394–97, 1989; Batra et al., *J. Biol. Chem.*, 265: 15198–15202, 1990; Batra et al., *Proc. Natl. Acad. Sci. USA* 86: 8545–8549, 1989; Chaudary et al., *Proc. Natl. Acad. Sci. USA* 87:1066–1070, 1990). Exemplary fusion constructs containing streptavidin are described by Sheldon et al., *Appl. Radiat. Isot.* 43(11):1399–1402, 1992; Sano and Cantor, *Bio/Technology* 9:1378–1381, 1991; Spooner et al., *Human Pathology* 25(6):606–614, 1994; Dubel et al., *J. Immun. Methods* 178:201–209, 1995; Kipriyanov et al., *Protein Engineering* 9(2):203–211, 1996. The DNA sequence comprising the linker may also provide sequences, such as primer sites or restriction sites, to facilitate cloning or may preserve the reading frame between the sequence encoding the scFv and the sequence encoding genomic streptavidin. The design of such linkers is well known to those of skill in the art.

Further, one skilled in the art would find it routine to test the ability of genomic streptavidin-antibody expressed gene fusions to bind the appropriate ligand. In contemplated embodiments, this ligand antigen may be a cell surface antigen, cell-associated stromal or matrix antigen, or cell-secreted antigens, including, but not limited to, CD19, CD20, CD22, CD25, CD33, CD45, CD52, CD56, CD57, EGP40 (or EPCAM or KSA), NCAM, CEA, TAG-72, a mucin (MUC-1 through MUC-7), β-HCG, EGF receptor and variants thereof, IL-2 receptor, her2/neu, Lewis Y, GD2, GM2, Lewis x, folate receptor, fibroblast activation protein, tenascin, sialylated tenascin, somatostatin, activated tumor stromal antigen, or a neoangiogenic antigen. Moreover, methods for evaluating the ability of antibodies to bind to epitopes of such antigens are known.

B9E9 scFvSA is a genetic fusion of the single-chain variable region of the murine anti-CD20 antibody B9E9 to the genomic streptavidin of *Streptomyces avidinii*. B9E9 scFvSA is a stable tetramer, consisting of 4 identical subunits containing a single chain B9E9 antibody fragment and a streptavidin subunit. The resulting species is tetravalent with respect to both antigen and biotin binding. However, an observed increased antigen-binding avidity should decrease streptavidin dissociation from tumor. In animals the B9E9 scFvSA exhibited more rapid systemic clearance than other antibody/SA conjugates, which is consistent with its smaller size and lack of the Fc region of the antibody. The biochemical uniformity of B9E9 scFvSA alone makes it a superior agent compared with other first-generation antibody/streptavidin conjugates. Similar advantageous characteristics are present with the CC49 scFvSA as well as other antibody streptavidin fusions.

D. Applicable Uses of Genomic Streptavidin Expressed Fusion Constructs

While any heterologous nucleic acid sequence can be joined to that encoding genomic streptavidin and expressed, as described herein, particularly useful expressed fusion constructs are those comprising scFv linked to genomic streptavidin, referred to previously as scFvSA. Accordingly, in one aspect of the invention, scFv fragments of antibodies are useful as tools in methods for medical diagnostic and therapeutic purposes. A diagnostic or therapeutic method, is described for detecting the presence or absence of, or treating, a target site within a mammalian host. When determining the criteria for employing antibodies or antibody conjugates for in vivo administration for therapeutic purposes, it is desirable that the generally attainable targeting ratio is high and that the absolute dose of therapeutic agent delivered to the tumor is sufficient to elicit a significant tumor response. Methods for utilizing such antibodies described in the present invention can be found, for example, in U.S. Pat. Nos. 4,877,868, 5,175,343, 5,213,787, 5,120,526, and 5,200,169. Upon in vivo administration for therapeutic or diagnostic purposes, it is also desirable to limit the exposure of non-target tissues to the therapeutic agent.

One method for reducing non-target tissue exposure to a diagnostic or therapeutic agent involves "pretargeting" the targeting moiety (e.g., scFvSA) to a target site, and then subsequently administering a rapidly clearing diagnostic or therapeutic agent conjugate that is capable of binding to the "pretargeted" targeting moiety at the target site. In this method, as generally described, an optional intermediate step may involve administration of a clearing agent to aid in the efficient removal of the unbound targeting moiety conjugate from the circulation prior to administration of the active agent conjugate. A description of embodiments of the pretargeting technique, including the descriptions of various clearing agents and chelates, such as DOTA, may be found in U.S. Pat. Nos. 4,863,713, 5,578,287, 5,608,060, 5,616,690, 5,630,996, 5,624,896, 5,847,121, 5,911,969, 5,914,312, 5,075,605, 5,976,535, 5,985,826, 6,015,897, 6,022,966, 6,075,010, 6,217,869, 6,287,536; and PCT publication Nos. WO 93/25240, WO 95/15978, WO 97/46098, WO 97/46099, which are incorporated herein in their entirety.

In the pretargeting approach the pharmacokinetics of the active agent is decoupled from that of the targeting moiety. The targeting moiety, conjugated to a member of a ligand/anti-ligand pair, is permitted to accrete to target sites. Accordingly, in one embodiment of the present invention, scFvSA is a conjugate (fusion) of the targeting moiety (scFv) and ligand (streptavidin). After accretion occurs and a substantial fraction of the non-target associated conjugate is cleared from the recipient's circulation, either by intrinsic clearance or via administration of a ligand or anti-ligand containing clearing agent, the active agent is administered as a conjugate to the member of the ligand/anti-ligand pair that is complementary to that of the targeting conjugate (e.g., biotin would be the complementary member in the exemplified embodiment). Preferably, the agent-ligand or agent-anti-ligand has a short serum half life and is excreted via the renal pathway. In this manner, the therapeutic agent either accretes to the target site where exertion of its therapeutic or diagnostic capability is desired, or it is rapidly removed from the recipient. This distribution of active agent facilitates the protection of normal tissues of the recipient from undesired toxicity. To enhance renal excretion, conjugation to a renal excretion-promoting biodistribution-directing molecule, may be employed. Essentially, such pretargeting methods are characterized by an improved targeting ratio or increased absolute dose to the target cell sites in comparison to conventional cancer diagnosis or therapy.

In one embodiment of the pretarget methodology, the targeting moiety will comprise an antibody fusion of the present invention specific for a particular antigen associated with the target cells of interest. In certain embodiments, the targeting moiety will comprise an antibody fusion comprising the CC49 antibody, or a functional homologue or fragment thereof. Such a targeting moiety should be capable of specifically binding CC49's cognate antigen, TAG-72. Specific disease states that may be targeted by such a targeting moiety include, but are not limited to, any TAG-72 positive human carcinoma or adenocarcinoma of the gastrointestinal tract (e.g., colon, rectum, gastric, esophagus), pancreas, ovary, endometrium, breast, prostate, lung, appendix, liver, salivary duct, including metastatic cancers, as well as cholangiocarcinoma.

In other embodiments, the targeting moiety will comprise an antibody fusion comprising the B9E9 antibody, or a functional homologue or fragment thereof, capable of binding its cognate antigen, CD20. Specific disease states targeted by such a targeting moiety include, but are not limited to, lymphomas, such as follicular, mantle cell, diffuse large B-cell, precursor B-lymphoblastic, lymphoplasmacytoid, marginal zone B-cell, splenic marginal zone, Burkitt, high grade B-cell, B-cell chronic lymphocytic, small lymphocytic, lymphoplasmacytoid, and plasmacytoma/melanoma, for example, as well as leukemias, such as prolymphocytic, B-cell chronic lymphocytic, precursor B-lymphoblastic, and hairy cell, for example. Accordingly, the aforementioned diseases serve as appropriate clinical indications for methods of the invention, including diagnostic assays and therapeutic treatment.

The Pretarget Lymphoma regimen is a powerful delivery system for radioimmunotherapy, which exploits the strong affinity of streptavidin for biotin ($Kd=10^{-15}M$). In certain embodiments of this regimen two or three steps are utilized. The first of the three step process involves the injection of a fusion protein that targets CD20, a cell-surface antigen expressed on approximately 90% of B-cell lymphomas. The fusion protein, B9E9 scFvSA, is a genetic fusion of the single-chain variable region of the murine anti-CD20 antibody B9E9 to the genomic streptavidin of Steptomyces avidinii. After allowing accretion of peak fusion protein levels at the tumor, a synthetic clearing agent is injected to remove unbound fusion construct from the circulation. Finally, radiolabeled DOTA-Biotin is injected. Due to the strong affinity between streptavidin and biotin, the radiolabeled DOTA-Biotin firmly binds to the streptavidin pre-localized to tumor cells. Excess radiolabeled DOTA-Biotin is rapidly excreted through the kidneys. Thus, radiation is delivered directly to tumor cells, with little uptake in normal tissues. This allows delivery of more radiation to the tumor, with the hope of improved tumor response.

Metastatic or recurrent gastrointestinal (GI) cancers represent a common and therapeutically frustrating form of cancer. They primarily represent adenocarcinomas arising from the GI tract (colorectal and gastric), pancreas and biliary tract (cholangiocarcinoma). A useful treatment modality is to target such cancer cells utilizing cell surface markers. One such marker is the TAG-72 antigen that has been used as the target in numerous radioimmunotherapy studies. The antigen, characterized as a high-molecular weight glycoprotein with mucin properties, has been purified from a human xenograft colon carcinoma designated LS-174T. TAG-72 is expressed in several epithelial-derived cancers, including most adenocarcinomas of the gastrointestinal tract, invasive ductal carcinomas of the breast, non-small cell lung carcinomas, and common epithelial ovarian carcinomas. TAG-72 expression has not been observed in tumors of neural, hematopoietic or sarcomatous derivation. Immunohistochemical studies have reported that TAG-72 is not appreciably expressed on normal tissues, with the exception of secretory endometrium and colonic epithelium. Another study showed TAG-72 reactivity in extracts of normal lung and stomach tissues by solid phase radioimmunoassay, and with small bowel, testis, lung and stomach by immunohistology. TAG-72 has previously been shown to be distinct from carcinoembryonic antigen, EpCam and other tumor-associated antigens.

Many antibodies to the TAG-72 antigen have been produced. In addition to B72.3, a murine anti-TAG-72 antibody, several second-generation antibodies have been generated using TAG-72 as the immunogen. Nine of these second generation antibodies, including CC49, have been further characterized. CC49 binds to a disaccharide epitope, designated sialyl Tn, on the TAG-72 antigen. This epitope is expressed by about 85% of human adenocarcinomas, including colon, breast, pancreatic, ovarian, endometrial, non-small cell lung and gastric cancers. In studies using human xenografts in athymic mice, CC49 had a 6-fold higher affinity constant and a 16-fold increase in the tumor:blood ratio than B72.3. The pancarcinoma distribution of the antigen and minimal reactivity of anti-TAG-72 antibodies with normal adult tissues suggest potential diagnostic and therapeutic utility for many human carcinomas.

Any other targeting antibodies may be used in the Pretarget regimen for example, CC49 scFvSA may be utilized in the 3-step Pretarget regimen in the treatment of patients with metastatic or locally advanced TAG-72-positive gastrointestinal adenocarcinoma. In the first step, injected CC49 scFvSA binds to the tumor. After allowing fusion protein to accrete to peak levels at the tumor, a synthetic clearing agent is injected to remove unbound CC49 scFvSA from the circulation. And finally, if the residual biotin binding assay indicates adequate blood clearance of CC49 scFvSA, radiolabeled DOTA-Biotin is injected.

In certain therapeutic and diagnostic embodiments, the formulation and dosing of the various components can vary depending the best dosage level identified during the course of clinical trials. In certain embodiments the formulations may be as follows: the scFvSA is produced in an *E. coli* fermentation process contains the antigen binding portion of the antibody of interest genetically linked to genomic streptavidin. The scFvSA though expressed as a monomer, spontaneously fold in to soluble tetramers. The fusion protein is formulated at a concentration of 5 mg/ml in phosphate buffered saline containing 5% sorbitol; one Synthetic Clearing Agent (sCA) (MW=8651.7 Daltons) of use is a non-toxic, synthetic biotin galactosamine compound. It contains no acidic or basic functional residues and is uncharged at physiological pH. It may be supplied as an aseptically filled sterile, pyrogen free solution in water at 12.7 mg sCA/ml and administered in 100 mL saline; the third component in a three part Pretarget regimen is DOTA-Biotin (MW=807 Daltons) that is a synthetic molecule containing a biotin lined to the macrocyclic amino benzyl DOTA chelate through an N-methyl glycine. Amino benzyl DOTA is designed for stable chelation of 3+metals such as Yttrium and Indium. It may be supplied at a concentration of 12 mg/ml.

Dosing in the three component system will be determined by clinical trials but will initially be investigated utilizing the following initial parameters: fusion protein dosing of 16–480 mg/M$^2$, time between fusion dosing and clearing agent dosing 20–72 hours, clearing agent 23–90 mg/m$^2$, time between clearing agent dosing and DOTA-Biotin dosing 10–24 hours, and radiolabeled DOTA-Biotin dosing of 0.33 to 2.6 mg/m$^2$. In most cases a residual biotin binding assay should be performed prior to administering radiolabeled DOTA-biotin. If the assay reveals greater than 5 ug/mL no radiolabeled DOTA-Biotin should be infused as the assay indicates that there is not adequate blood clearance of the fusion construct.

In related embodiments, the antigen marker may be associated with a cancer, including, but not limited to, the following: lymphoma (e.g., CD20); leukemia (e.g., CD45); prostate (e.g., TAG-72); ovarian (e.g., TAG-72); breast (e.g., MUC-1); colon (e.g., CEA, TAG-72); and pancreatic (e.g., TAG-72). For example, the CD20 antigen may be targeted for the treatment of lymphoma wherein the ligand/anti-ligand binding pair may be biotin/avidin (e.g., streptavidin-gene fusion (scFvSA)), and the active agent will be a radionuclide in pretargeting methods. Further, a variety of antigens may be targeted, such as CD45 antigen targeting for pretargeted radioimmunotherapy (PRIT) to treat patients having any one of a broad range of hematologic malignancies by employing antibody-mediated targeting to the CD45 antigen. CD45 is the most broadly expressed of the known hematopoietic antigens, found on essentially all white blood cells and their precursors, including neutrophils, monocytes and macrophages, all lymphocytes, myeloid and lymphoid precursors, and about 90% of acute myelogenous leukemia (AML) cells. Accordingly, as the antigens available for targeting for diagnostic or therapeutic purposes are numerous, the present invention may be used to facilitate targeting to any of these antigens.

An optional step in pretarget methods, including those identified above, comprises the initial administration of a non-conjugated targeting moiety (i.e., not conjugated to a ligand or anti-ligand) or, alternatively, administering this non-conjugated targeting moiety concurrently with the conjugated form in the first step, thus blocking those targets contacted initially. Such blocking may be especially useful, for example, in the treatment of non-Hodgkin's lymphoma, where the first set of targeted tissues may be the spleen, while most tumors are found in the deep lymph nodes. Such pre-blocking allows for substantial protection of the spleen cells from later treatment with the active agent. While the non-conjugated targeting agent need not necessarily bind the same epitope, to be effective it should preclude binding by the targeting moiety conjugate.

One skilled in the art could use multiple targeting moiety conjugates comprising different antibodies that also bind to the same cell type to enhance the therapeutic effect or diagnostic utility. U.S. Pat. No. 4,867,962 issued to Abrams describes such an improved method for delivering active agent to target sites, which method employs active agent-targeting moiety conjugates. Briefly, the Abrams method contemplates administration to a recipient two or more active agent-targeting moiety conjugates, wherein each conjugate includes a different antibody species as the targeting moiety. Each of the utilized antibody species is reactive with a different target site epitope (associated with the same, or a different, target site antigen), while the patterns of cross-reactivity of the antibody species with non-target tissues are non-overlapping. In this manner the different antibodies accumulate additively at the desired target site, while fewer than the total species accumulate at any type of non-target tissue. A higher percentage of the administered agent, therefore, becomes localized in vivo at target sites than at non-target tissues. The present invention encompasses approaches similar to this, as well as in pretargeting formats. In one embodiment, for example, two or more species of targeting conjugates (fusion) with antibodies directed to different epitopes and having non-overlapping cross-reactivity, each prepared according to the present invention, are administered according to the pretarget method so as to improve the diagnostic or therapeutic utility. A further embodiment utilizes the property that streptavidin monomers naturally associate to form tetramers. Thus, two or more antibodies each conjugated (fusion) to the monomeric form of streptavidin, are selectively combined and, upon formation of tetrameric streptavidin, yield single species with specificity for multiple epitopes at the target site.

It should be understood that the methods described may be modified and still achieve the desired effect. For example, two antibodies specific for the same antigen or cell type, regardless of their respective cross-reactivity, may be used. All that is necessary for these methods is that the targeting moiety-ligand/anti-ligand conjugate preferentially binds the target cells and that the active agent-conjugate substantially localizes to the pretargeted cells and is in certain embodiments otherwise substantially cleared from circulation.

Alternatively, antibody-based or non-antibody-based targeting moieties may be employed to deliver a ligand/anti-ligand to a target site bearing an unregulated antigen. Preferably, a natural binding agent for such an unregulated antigen is used for this purpose.

Pretarget methods as described herein optionally include the administration of a clearing agent. The dosage of the clearing agent is an amount which is sufficient to substantially clear the previously administered targeting moiety-ligand/anti-ligand conjugate from the circulation. Generally, the determination of when to administer the clearing agent depends on the target uptake and endogenous clearance of the targeting moiety conjugate. Particularly preferred clearing agents are those which provide for Ashwell receptor-mediated clearance, such as galactosylated proteins, e.g., galactosylated biotinylated human serum albumin, and small molecule clearing agents containing N-acetylgalactosamine and biotin.

Types of active agents (diagnostic or therapeutic) useful herein include radionuclides, toxins, anti-tumor agents, drugs, genes, and cytokines. For example, as described above, conjugates of such agents to biotin may be useful in the pretargeting approach. In this regard, a therapeutic antibody (e.g., an antibody that induces apoptosis or inhibits angiogenesis) may be used in a therapeutic modality such as pretargeting. With regard to diagnostic agent fusions, in contrast to therapeutic agent fusions, enhanced target cell internalization is disadvantageous if one administers diagnostic agent-targeting moiety conjugates Internalization of diagnostic conjugates results in cellular catabolism and degradation of the conjugate. Upon degradation, small adducts of the diagnostic agent or the diagnostic agent per se may be released from the cell, thus eliminating the ability to detect the conjugate in a target-specific manner.

Diagnostic or therapeutic agents useful herein include radionuclides, drugs, anti-tumor agents, toxins, genes, and cytokines. Radionuclides useful within the present invention include gamma-emitters, positron-emitters, Auger electron-emitters, X-ray emitters and fluorescence-emitters, with beta- or alpha-emitters preferred for therapeutic use. Radionuclides are well-known in the art and include $^{123}$I, $^{125}$I, $^{130}$I, $^{131}$I, $^{133}$I, $^{135}$I, $^{47}$Sc, $^{72}$As, $^{72}$Se, $^{90}$Y, $^{88}$Y, $^{97}$Ru, $^{100m}$Rh, $^{119}$Sb, $^{128}$Ba, $^{197}$Hg, $^{211}$At, $^{212}$Bi, $^{153}$Sm, $^{169}$Eu, $^{212}$Pb, $^{109}$Pd, $^{111}$In, $^{67}$Ga, $^{68}$Ga, $^{64}$Cu, $^{67}$Cu, $^{75}$Br, $^{76}$Br, $^{77}$Br, $^{99m}$Tc, $^{11}$C, $^{13}$N, $^{15}$O, $^{166}$Ho and $^{18}$F. Preferred therapeutic radionuclides include $^{188}$Re, $^{186}$Re, $^{203}$Pb, $^{212}$Bi, $^{213}$Bi, $^{109}$Pd, $^{64}$Cu, $^{67}$Cu, $^{90}$Y, $^{125}$I, $^{131}$I, $^{77}$Br, $^{211}$At, $^{97}$Ru, $^{105}$Rh, $^{198}$Au and $^{199}$Ag, $^{166}$Ho or $^{177}$Lu.

As one of ordinary skill in the art can readily appreciate the above streptavidin gene fusions may be utilized in combination therapies, such as when "pretargeting" is combined with the use of radiation-sensitizing agents. Such radiation sensitizing agents include, but are not limited to, gemcitabine, 5-fluorouracil, paclitaxel, and the like.

Several of the potent toxins useful within the present invention consist of an A and a B chain. The A chain is the cytotoxic portion and the B chain is the receptor-binding portion of the intact toxin molecule (holotoxin). Because toxin B chain may mediate non-target cell binding, it is often advantageous to conjugate only the toxin A chain to a targeting moiety (e.g., molecule). However, while elimination of the toxin B chain decreases non-specific cytotoxicity, it also generally leads to decreased potency of the conjugated toxin A chain, as compared to the conjugate of the corresponding holotoxin.

Preferred toxins in this regard include holotoxins, such as abrin, ricin, modeccin, *Pseudomonas* exotoxin A, *Diphtheria* toxin, pertussis toxin, Shiga toxin, and bryototoxin; and A chain or "A chain-like" molecules, such as ricin A chain, abrin A chain, modeccin A chain, the enzymatic portion of *Pseudomonas* exotoxin A, *Diphtheria* toxin A chain, the enzymatic portion of pertussis toxin, the enzymatic portion of Shiga toxin, gelonin, pokeweed antiviral protein, saporin, tritin, barley toxin and snake venom peptides. Ribosomal inactivating proteins (RIPs), naturally occurring protein synthesis inhibitors that lack translocating and cell-binding ability, are also suitable for use herein. Highly toxic toxins, such as palytoxin and the like, are also contemplated for use in the practice of the present invention. However, therapeutic drugs may themselves facilitate internalization of the complex.

Therapeutic drugs, administered as targeted conjugates, are also encompassed herein. Again, the goal is administration of the highest possible concentration of drug (to maximize exposure of target tissue), while remaining below the threshold of unacceptable normal organ toxicity (due to non-target tissue exposure). Unlike radioisotopes, however, many therapeutic drugs need to be taken into a target cell to exert a cytotoxic effect. In the case of targeting moiety-therapeutic drug conjugates, it would be advantageous to combine the relative target specificity of a targeting moiety with a means for enhanced target cell internalization of the targeting moiety-drug conjugate.

Therapeutic drugs suitable for use herein include conventional chemo-therapeutics, such as vinblastine, doxorubicin, bleomycin, methotrexate, 5-fluorouracil, 6-thioguanine, cytarabine, cyclophosphamide and cis-platinum, as well as other conventional chemotherapeutics including those described in *Cancer: Principles and Practice of Oncology*, 2d ed., V. T. DeVita, Jr., S. Hellman, S. A. Rosenberg, J. B. Lippincott Co., Philadelphia, Pa., 1985, Chapter 14, and analogues of such drugs where the analogue has greater potency that the parent molecule. Another drug within the present invention is a trichothecene. Other preferred drugs suitable for use herein as a diagnostic or therapeutic active agent in the practice of the present invention include experimental drugs including those as described in *NCI Investigational Drugs, Pharmaceutical Data* 1987, NIH Publication No. 88–2141, Revised November 1987.

Other anti-tumor agents, e.g., agents active against proliferating cells, are administerable in accordance with the present invention. Exemplary anti-tumor agents include pro-apoptotic antibodies, anti-angiogenic antibodies, cytokines, such as IL-2, tumor necrosis factor or the like, lectin inflammatory response promoters (selectins), such as L-selectin, E-selectin, P-selectin or the like, and similar molecules.

One skilled in the art, based on the teachings in this application and the applications referenced herein, can readily determine an effective diagnostic or therapeutic dosage and treatment protocol. This will depend upon factors such as the particular selected therapeutic or diagnostic agent, the route of delivery, the type of target site(s), affinity of the targeting moiety for the target site of interest, any cross-reactivity of the targeting moiety with normal tissue, condition of the patient, whether the treatment is effected alone or in combination with other treatments, among other factors. A therapeutic effective dosage is one that treats a patient by extending the survival time of the patient. Preferably, the therapy further treats the patient by arresting the tumor growth and, most preferably, the therapy further eradicates the tumor.

All the references, including patents and patent applications, discussed throughout, are hereby incorporated by reference in their entirety.

The present invention is further described through presentation of the following examples. These examples are offered by way of illustration and not by way of limitation.

EXAMPLES

Example I

Construction of huNR-LU-10 Single Chain Antibody-Genomic Streptavidin Fusion

Generically, a single chain Fv/streptavidin (scFvSA) fusion protein is expressed from the genetic fusion of the single chain antibody of the variable regions (scFv) to the genomic streptavidin of *Streptomyces avidinii*. The scFv gene consists of the variable regions of the light ($V_L$) and heavy ($V_H$) chains separated by a DNA linker sequence (e.g., FIG. 2). The streptavidin coding sequence is joined to the 3' terminus of the scFv gene, and the two genes are separated in-frame by a second DNA linker sequence. The signal sequence from the streptavidin gene is fused at the 5' terminus of the scFvSA gene to direct expression to the *E. coli* periplasmic space. The scFvSA gene is under control of the lac promoter, and the expressed fusion protein is extracted and purified from *E. coli* and forms a soluble tetramer of about 173,000 molecular weight.

Figure 6:
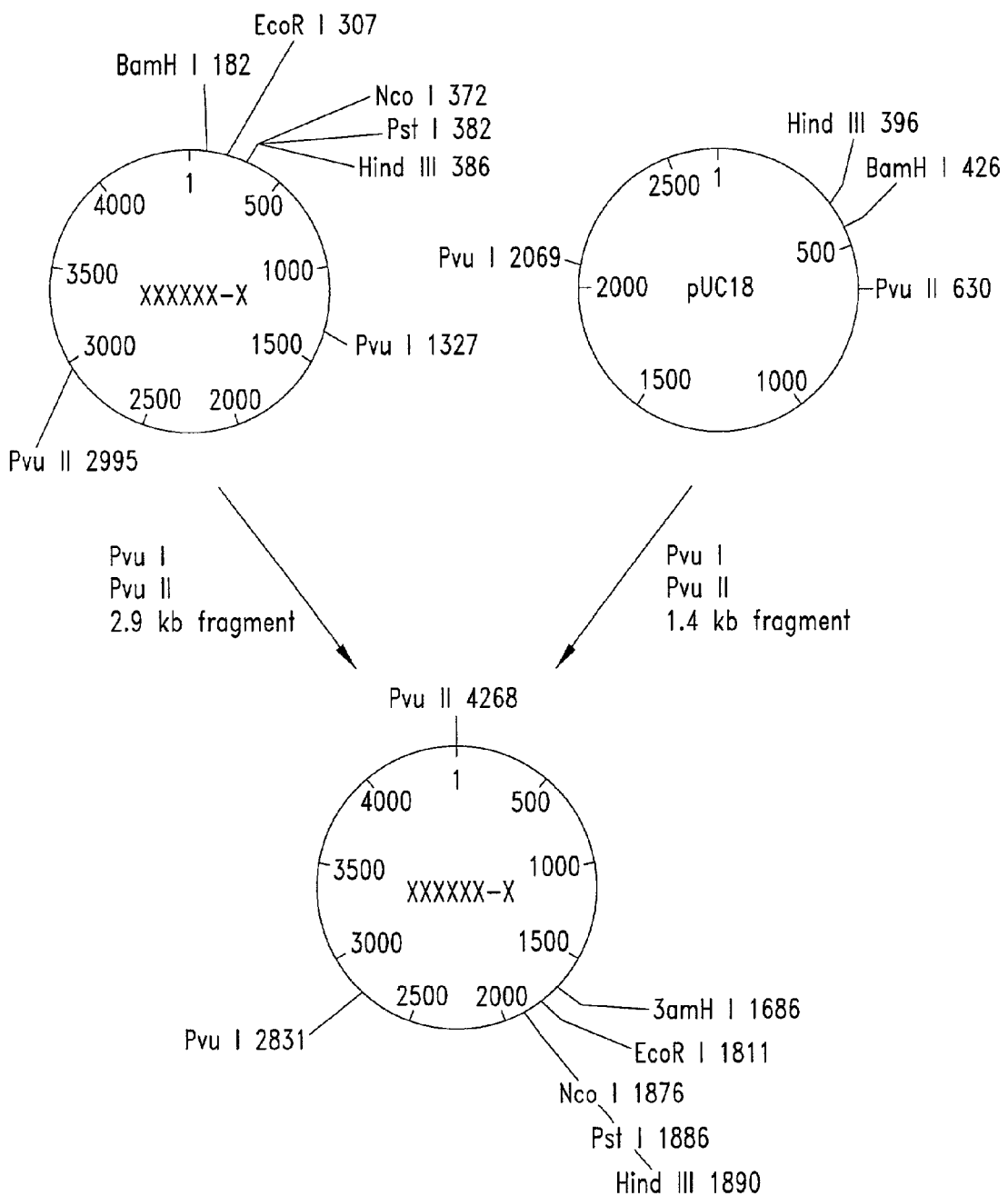
FIG. 6 is a schematic representation of the construction of the pEX-1 vector.

Plasmid pKK233-2 (Amersham Pharmacia Biotech, Piscataway, N.J.) was digested with BamHI and NcoI to remove the trc promoter. The lac promoter was amplified from pBR322 by polymerase chain reaction (PCR) and cloned into the BamHI/NcoI site of pKK233-2. In the process an EcoR[site was introduced immediately 5' to the NcoI site. The plasmid was digested with NcoI and PstI and ligated with oligonucleotides encoding the pelB leader sequence. The accepting NcoI site on the plasmid was not regenerated and a new NcoI site was introduced in the 3' area of the pelB encoding sequence. The resulting plasmid was referred to as pKK-lac/pelB (FIG. 5). pKK-lac/pelB and pUC 18 were digested with PvuI and PvuII. The 2.9 kb fragment of pKK-lac/pelB containing the lac promoter and multi-cloning site was ligated to the 1.4 kb fragment of pUC 18 containing the origin of replication to form plasmid pEX-1 (FIG. 6).

Figure 7:
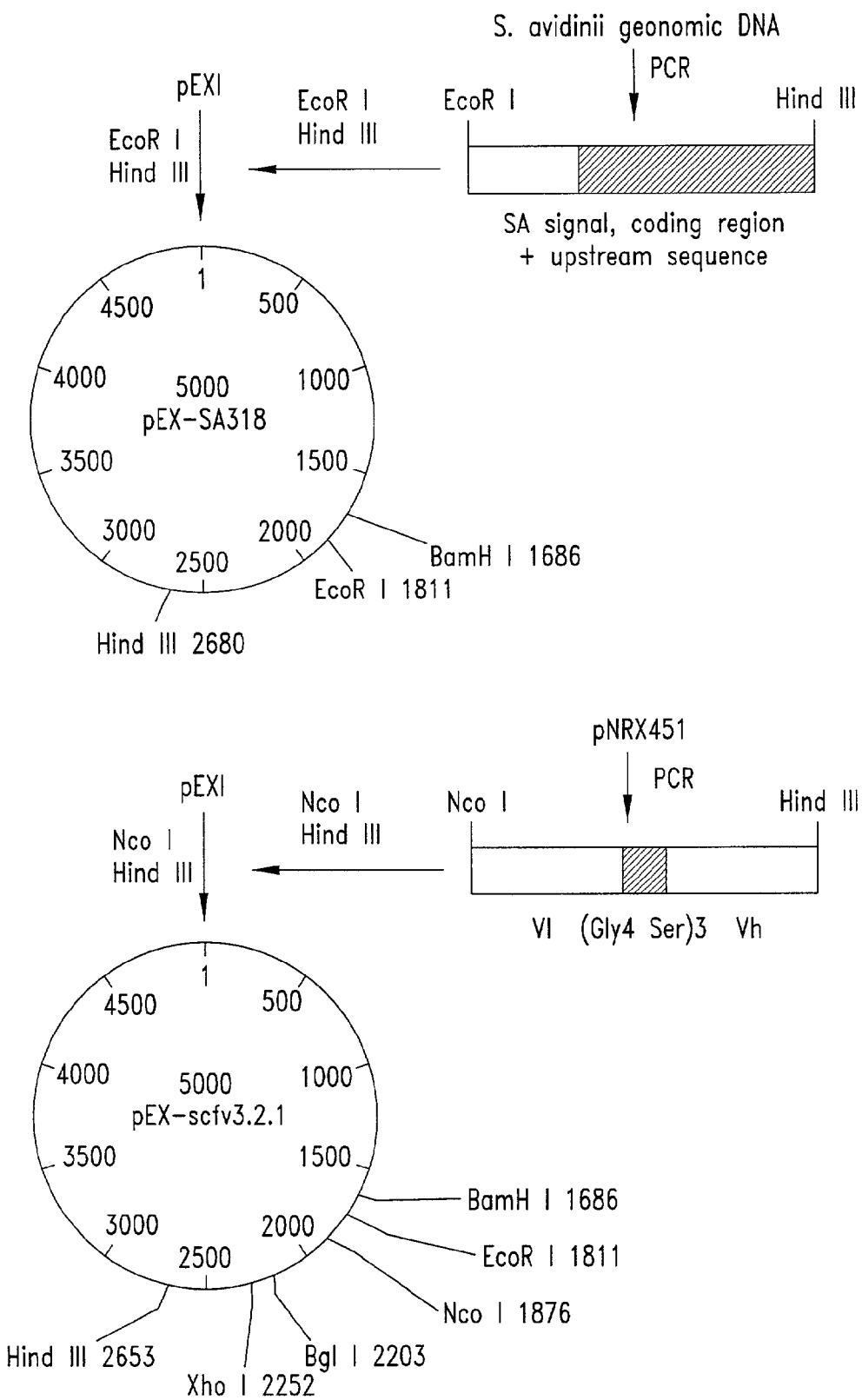
FIG. 7 is a schematic representation of the construction of the pEX-SA318 and pEX-scFv3.2.1 vectors.
Figure 8:
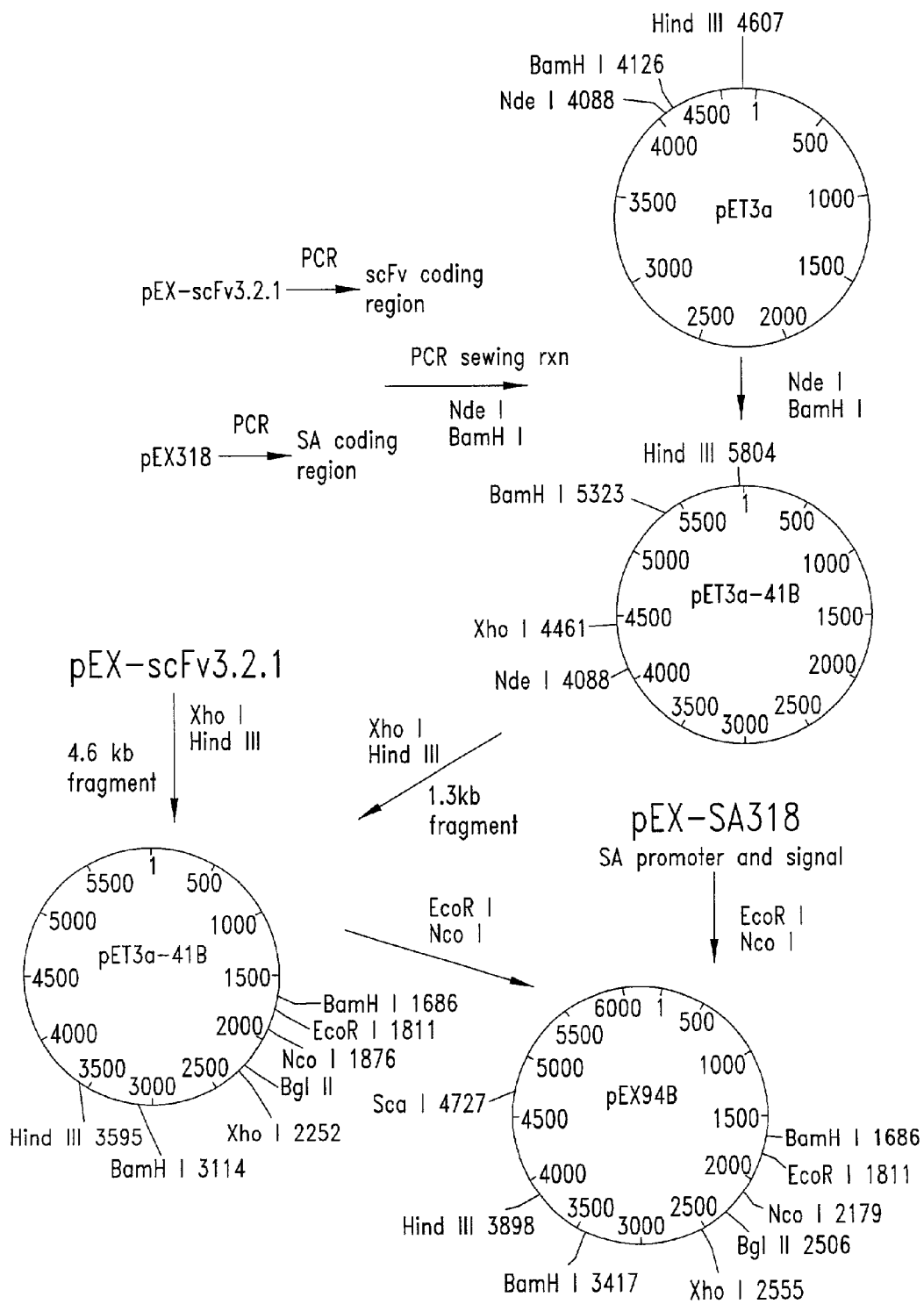
FIG. 8 is a schematic representation of the construction of the pEX94B vector.

The streptavidin and huNR-LU-10 scFv genes (a monoclonal antibody that binds the antigen EGP40 or EPCAM, epithelial glycoprotein, 40 kD) were cloned onto separate plasmids prior to construction of the huNR-LU-10 scFvSA gene. The streptavidin gene, signal sequence and approximately 300 bp of upstream sequence were PCR-amplified from *Streptomyces avidinii* (ATCC 27419) genomic DNA and cloned into pEX-1 as an EcoRI/HindIII fragment to form pEX318 (FIG. 7). The huNR-LU-10 scFv was derived from the humanized antibody plasmid pNRX451 (Graves et al., *Clin. Cancer Res.*, 5:899–908, 1999). The heavy and light chain variable regions were PCR-amplified separately from pNRX451 and then combined in a subsequent PCR. Oligonucleotides used in this process were designed to introduce a (Gly$_4$Ser)$_3$ linker [SEQ ID NO:10] between the leading $V_L$ and the trailing $V_H$. The resulting PCR product was cloned into pEX-1 as a NcoI/HindIII fragment forming the plasmid pEX-scFv3.2.1 (FIG. 7). The scFv and streptavidin genes were PCR-amplified from pEX-scFv3.2.1 and pEX318, respectively, and combined into a fusion, as illustrated in FIG. 8. The oligonucleotides used in these reactions created an overlap between the 3' end of the leading scFv and the 5' end of the trailing streptavidin, which encoded a five amino acid linker (GSGSA; SEQ ID NO:7 1). The fragments were joined by PCR using the outside primers. The resulting 1.25 kb fragment was cloned into the NdeI and BamHI sites of vector pET3a (Novagen), generating pET3a-41B. This plasmid was digested with XhoI and HindIII, and the 1.3 kb fragment containing the $V_H$-SA coding region and transcription terminator was ligated to a 4.6 kb XhoI/HindIII fragment of pEX-scFv3.2.1 containing the $V_L$ coding region, lac promoter, and ampicillin resistance gene (pYL256). The streptavidin regulatory region and signal sequence were PCR-amplified from pEX318 and cloned into the EcoRI/NcoI sites of pYL256 to form pEX94B (FIG. 8).

Figure 9:
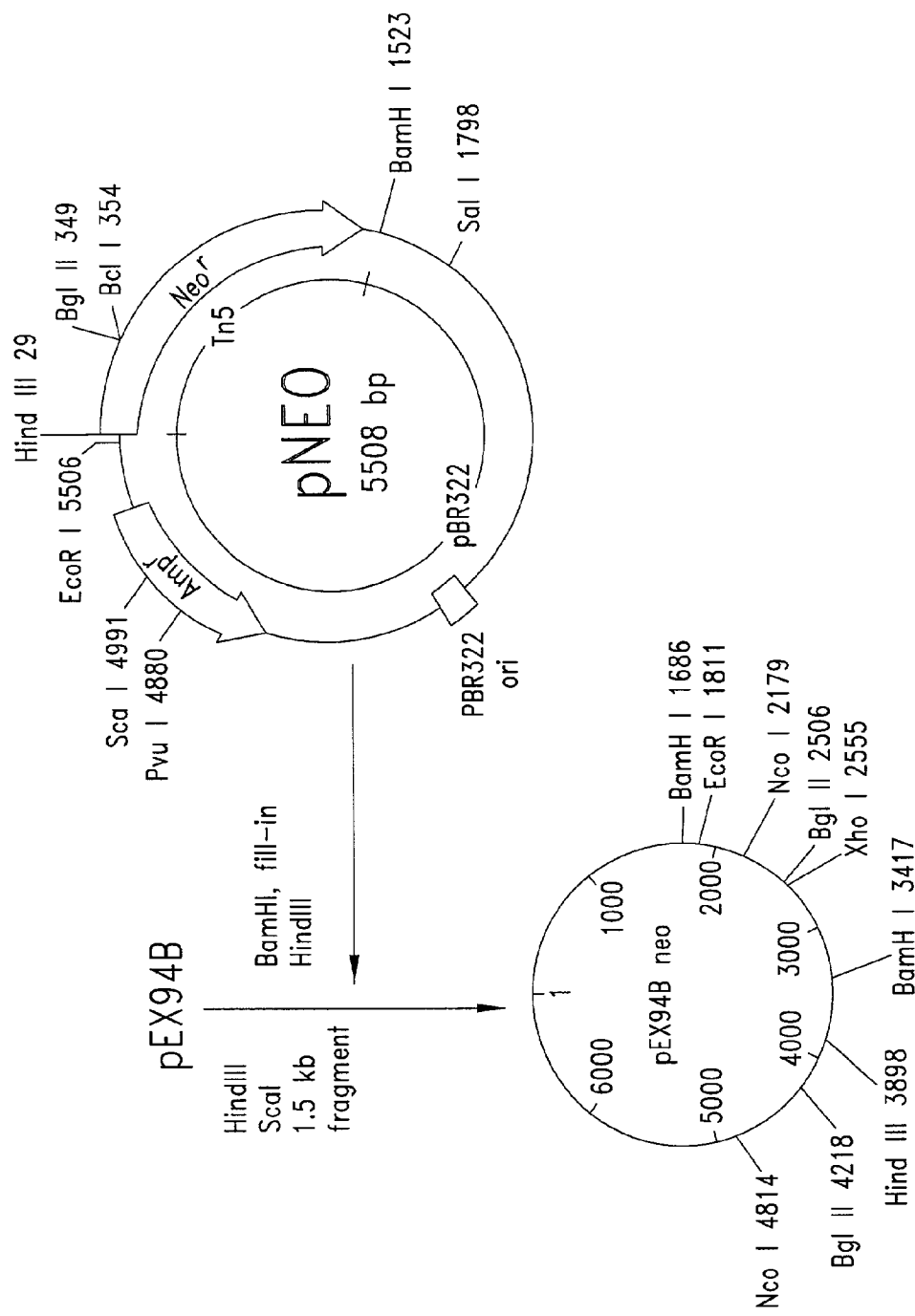
FIG. 9 is a schematic representation of the construction of the pEX94B neo vector.

The Tn5 kanamycin resistance gene (neo) was inserted into the huNR-LU-10 scFvSA expression plasmid pEX94B as follows (FIG. 9): plasmid pNEO (Amersham Pharmacia) was digested with BamHI, blunt-ended with nucleotides using Pfu polymerase (Stratagene, La Jolla, Calif.), then further digested with HindIII. The 1494 bp fragment containing the kanamycin resistance gene was ligated to HindIII/ScaI-digested pEX94B plasmid, generating plasmid pEX94Bneo. The DNA sequence of the 1.6 kb EcoRI to BamHI fragment of plasmids pEX94B and pEX94Bneo is shown in FIG. 10.

Example II

Construction of B9E9 scFvSA Fusions

Additional single chain antibodies containing genomic streptavidin were constructed in a similar manner as noted above. A scFvSA version of the anti-CD20 mAb, B9E9, was constructed in the $V_L V_H$ orientation with either a $(Gly_4Ser)_3$ (SEQ ID NO: 10) linker or a linker termed pKOD (amino acids GLEGSPEAGLSPDAGSGS) (SEQ ID NO: 9). Briefly, B9E9-1D3 hybridoma cells ($1 \times 10^7$)(from Bioprobe BV, Amstelveen, The Netherlands) were harvested, and total RNA was prepared. The cDNAs for kappa chain and heavy chain of B9E9 were obtained by a reverse transcriptase reaction using primers RX207 and RX215, respectively. PCR fragments of variable regions of kappa chain and heavy chain were obtained using above cDNAs and pairs of oligos (RX207 and NX54 for kappa chain; RX215 and NX50 for heavy chain). The PCR fragments were digested with EcoRI and NotI and subsequently cloned into a pPICαA vector (Invitrogen, Sorrento Valley, Calif.), previously restricted with EcoRI and NotI. The resultant plasmids C58-1 and C58-16 carried B9E9 kappa chain and heavy chain, respectively. The two chains were further cloned out from C58-1 and C58-16 by PCR using pairs of oligos (RX468 and RX469 for kappa chain; RX470 and RX471 for heavy chain). The kappa chain fragment was digested with NcoI and BglII and the heavy chain was digested with XhoI-SacI, respectively. The kappa chain was cloned into pEX94B (NcoI-BglII) as vector and heavy chain was cloned at XhoI-SacI sites in pEX94B. The resultant plasmids (C74-2 for kappa chain and C76-10 for heavy chain) were digested with XhoI and HindIII. The small fragment from C76-10 was ligated into C74-2 vector restricted with the same enzymes. A resultant plasmid (C87-14) carried B9E9 scFvSA fusion protein with a $(G_4S)_3$ (SEQ ID NO: 10) linker between kappa chain and heavy chain. The C87-14 was further digested with BglII and XhoI and ligated with a pKOD linker prepared with two oligos (pInew5' and pInew3') to generate C136-1. FIGS. 11A and 11B illustrate the determined nucleic acid sequence and predicted amino acid sequence of B9E9pKOD scFvSA.

Another version of B9E9 scFvSA was constructed in the $V_H V_L$ orientation with an extended 25mer $(Gly_4Ser)_5$ (SEQ ID NO: 11) linker. The NcoI-SacI fragment of C87-14 containing scFv was further subcloned by PCR using a pair of primers (RX633 and RX471) to add a serine residue in the $V_L$ region. The PCR fragment was digested with NcoI and SacI and cloned into the pEX94B vector restricted with NcoI and SacI. The resultant plasmid D59-3 was subject to subcloning to generate the $V_H$ or $V_L$ fragments by PCR using RX781 and RX782 or RX729 and RX780, respectively. The $V_H$ PCR fragment was digested with NcoI and BglII and cloned into the pEX94B vector at the same sites to form D142-6. The $V_L$ PCR fragment was digested with XhoI and SacI and cloned into the pEX94B vector at the same sites to form D142-1. A XhoI-HindIII fragment from D142-1 was isolated and replaced a XhoI-HindIII fragment of D142-6 to generate D148-1 ($V_H$-$V_L$ scFvSA). A HindIII-BamHI fragment, (blunted at BamHI side) containing a neo gene as described previously, was used to replace a HindIII-ScaI fragment of D148-1 to form D164-13. The D148-1 was also digested with BglII and XhoI to remove the linker fragment and ligated with a 25mer linker (annealed with RX838 and RX839) to form E5-2-6. A EcoRI-HindIII fragment of E5-2-6 containing $V_H$-$V_L$ scFvSA was excised and ligated with the D164-13 vector previously restricted with EcoRI and HindIII to form E31-2-20. Both plasmids E5-2-6 (carbenicillin-resistant) and E31-2-20 (kanamycin-resistant) express the B9E9 scFvSA fusion protein. FIG. 11C illustrates the nucleic acid sequence and predicted amino acid sequence of B9E9 scFvSA ($V_H$-$V_L$ 25-mer).

All oligonucleotide primers, as listed below, were synthesized by Operon Technologies, Inc. (Alameda, Calif.).

```
NX50
TGCCGTGAATTCGTSMARCTGCAGSARTCWGG       (SEQ ID NO:12)

NX54
TGCCGTGAATTCCATTSWGCTGACCARTCTC        (SEQ ID NO:13)

RX207
TAGCTGGCGGCCGCCCTGTTGAAGCTCTTGACAAT    (SEQ ID NO:14)

RX215
TAGCTGGCGGCCGCTTTCTTGTCCACCTTGGTGC     (SEQ ID NO:15)

RX468
TTACGGCCATGGCTGACATCGTGCTGCAGTCTCCAG   (SEQ ID NO:16)
CAATCCTGTCT

RX469
CACCAGAGATCTTCAGCTCCAGCTTGGTCCCA       (SEQ ID NO:17)

RX470
CGGAGGCTCGAGCCAGGTTCAGCTGGTCCAGTCAGG   (SEQ ID NO:18)
GGCTGAGCTGGTGAAG

RX471
GAGCCAGAGCTCACGGTGACCGTGGTCCCTGCGCCC   (SEQ ID NO:19)
CA pInew5'
GATCTCTGGTCTGGAAGGCAGCCCGGAAGCAGGTCT   (SEQ ID NO:20)
GTCTCCGGACGCAGGTTCCGGC pInew3'
TCGAGCCGGAACCTGCGTCCGGAGACAGACCTGCTT   (SEQ ID NO:21)
CCGGGCTGCCTTCCAGACCAGA

RX633
TTACGGCCATGGCTGACATCGTGCTGTCGCAGTCTC   (SEQ ID NO:22)
CAGCAATCCTGTCT

RX779
TTCCGGCTCGAGCGACATCGTGCTGTCGCAGTCTCC   (SEQ ID NO:23)
A

RX780
GAGCCAGAGCTCTTCAGCTCCAGCTTGGTCCC       (SEQ ID NO:24)

RX781
TTACGGCCATGGCTCAGGTTCAGCTGGTCCAGTCA    (SEQ ID NO:25)

RX782
AGACCAGAGATCTTGCTCACGGTGACCGTGGTCCC    (SEQ ID NO:26)

RX838
GATCTCTGGTGGCGGTGGCTCGGGCGGTGGTGGGTC   (SEQ ID NO:27)
GGGTGGCGGCGGCTCGGGTGGTGGTGGGTCGGGCGG
CGGCGGC

RX839
TCGAGCCGCCGCCGCCCGACCCACCACCACCCGAGC   (SEQ ID NO:28)
CGCCGCCACCCGACCCACCACCGCCCGAGCCACCGC
CACCAGA
```

Example III

Expression Of huNR-LU-10 scFvSA and B9E9 scFvSA Proteins

Transformants of *E. coli* strain XL1-Blue (Stratagene, La Jolla, Calif.) containing plasmids pEX94B (huNR-LU-10 scFvSA) or E5-2-6 (B9E9 scFvSA) were grown overnight at 30° C. in Terrific broth (20 ml; Sigma) containing carbenicillin (50 µg/ml). The culture was diluted 100-fold into fresh medium and grown in a shaking incubator at 30° C. When the culture attained an $A_{600}$ of 0.3–0.5, IPTG (Amersham Pharmacia Biotech, Piscataway, N.J.) was added to a final concentration of 0.2 mM, and incubation was continued overnight. Periplasmic extracts were prepared for qualitative analysis of the scFvSA expression level. Cells were resuspended in an ice-cold solution of 20% sucrose, 2 mM EDTA, 30 mM Tris, (pH 8.0), and lysozyme (2.9 mg/ml) and were incubated on ice for 30 min. Supernatants were analyzed on 4–20% Tris-glycine SDS-PAGE gels (Novex) under non-reducing, non-boiled conditions, and gels were stained with Coomassie Blue. Expression in shake flasks was optimized by testing different environmental parameters, such as IPTG concentration and timing, temperature, media, or carbon source, or testing genetic factors, such as different promoters or signal sequences.

Clones were further grown in an 8L fermentor and analyzed for expression level. The primary inoculum (50 ml) was grown overnight at 30° C. in shake flasks containing Terrific broth plus 50 µg/ml kanamycin (plasmids pEX94Bneo or E31-2-20) or carbenicillin (plasmids pEX94B or E5-2-6), depending on the selectable marker of the plasmid. The culture was then diluted 100-fold into the same medium and grown at 30° C. for an additional 4–5 h. This secondary inoculum (0.5 liter) was transferred to a 14 liter BIOFLO 3000 fermentor (New Brunswick Scientific) containing 8 liters of complete *E. coli* medium [per liter: 6 g $Na_2HPO_4$, 3 g $KH_2PO_4$, 0.5 g NaCl, 3 g $(NH_4)_2SO_4$, 48 g yeast extract (Difco), 0.25 ml MAZU DF204 antifoam (PPG Industries Inc., Pittsburgh, Pa.), 0.79 g $MgSO_4$-$7H_2O$, 0.044 g $CaCl_2$-$2H_2O$, and 3 ml of trace elements (per liter: 0.23 g $CoCl_2$, 0.57 g $H_3BO_3$, 0.2 g $CuCl_2$-$2H_2O$, 3.5 g $FeCl_3$-$6H_2O$, 4.0 g $MnCl_2$-$4H_2O$, 0.5 g ZnCl, 1.35 g thiamine, and 0.5 g $Na_2MoO_4$-$2H_2O$)]. The medium contained an initial 5 g/liter galactose as carbon source plus 50 µg/ml of kanamycin or carbenicillin for plasmid retention. The culture was grown at 30° C. and induced with IPTG (0.2 mM) at 6 h post-inoculation. The pH was maintained at 7.0 by the automatic addition of either phosphoric acid or NaOH. Dissolved oxygen concentration was maintained at or above 30% throughout the run using agitation speeds of 400–800 rpm and oxygen supplementation as necessary. A galactose solution (50%) was fed over a 9 h period after exhaustion of the initial galactose present in the medium to a total of 20–25 g per liter. Cells were harvested at 24–26 h post-inoculation (for B9E9 scFvSA) or 48–56 h post-inoculation (for huNR-LU-10 scFvSA) in a continuous flow centrifuge (POWERFUGE PILOT, Carr Separations, Franklin, Mass.), washed with PBS (10 mM sodium phosphate, 150 mM NaCl, pH 7.2), and pelleted by centrifugation. A typical fermentation produced 80–90 g of cells (wet wt) per liter culture medium.

For determining expression levels, cells were washed twice in PBS, resuspended to the original volume, and disrupted either by sonication on ice (Branson Ultrasonics, Danbury, Conn.) or through two cycles of microfluidization (Microfluidics International, Newton, Mass.). Two assays were used for quantitating fusion protein in the supernatent of a centrifuged sample of crude lysate. Initially, an ELISA assay was used in which biotinylated albumin (100 ng per well in PBS) was coated overnight in 96-well plates at 4° C. and incubated with serial two-fold dilutions of either HPLC-purified fusion protein (200 ng/ml) or test samples. Detection was using peroxidase-labeled goat anti-streptavidin polyclonal antibody (Zymed, So. San Francisco, Calif.) and ABTS (Sigma) substrate buffer. Plates were read at 415/490 nm with a dual wavelength automated plate reader. A first order, log x/log y regression analysis was performed for quantitation of the fusion protein.

Alternatively, a rhodamine-biotin HPLC assay was devised that provided faster results. The fusion protein in centrifuged lysates was complexed with excess rhodamine-derivatized biotin, which was prepared as follows: 5-(and-6-)-carboxytetramethylrhodamine, succinimidyl ester (Molecular Probes, Eugene Oreg.) was coupled to biocytin (Pierce, Rockford Ill.) through the formation of a stable amide bond. The reaction mixture was purified by HPLC using a DYNAMAX semi-preparative C-18 column (Rainin Instrument Co., Woburn, Mass.). The effluent was monitored at 547 nm and peak fractions collected and analyzed by mass spectrometry. Fractions corresponding in molecular weight to biocytin-rhodamine conjugate were pooled and concentrated by roto-evaporation (Buchii, Switzerland). An excess of purified biocytin-rhodamine conjugate was added to the clarified crude lysate and analyzed by size exclusion chromatography using a ZORBAX GF-250 column (MAC-MOD, Chadds Ford Pa.) equilibrated in 20 mM sodium phosphate containing 15% DMSO at 1.0 ml/mm flow rate. The effluent was monitored at 547 nm using a Varian™ DYNAMAX PDA-2 detector, and the peak area corresponding to fusion protein elution was determined using a Varian™ DYNAMAX HPLC Data System (Walnut Creek, Calif.). The concentration of fusion protein in the crude lysate was calculated by comparison to a standard analyzed under the same conditions. The molar extinction coefficient for the fusion protein standard was calculated using a previously described method summing the relative contributions of amino acids absorbing at 280 nm (Gill and von Hippel, *Analyt. Chem.* 182:319–326, 1989).

Expression levels in fermentor-grown cells were 100–130 mg/liter for huNR-LU-10 scFvSA, 40 mg/liter for B9E9pKOD scFvSA, and 270–300 mg/liter for B9E9 scFvSA ($V_H$-$V_L$ 25-mer).

Example IV

Expression of B9E9 scFvSA Using Various Linkers and Signal Sequences

A number of genetic variants were constructed that contained linkers of different lengths and composition and the variable regions in different order (Table 1). These constructs were initially grown and induced in shake flask cultures and qualitatively assessed for expression by visualizing periplasmic proteins on Coomassie-stained, non-reducing SDS gels. High-expressing constructs were further tested in an 8L fermentor using a galactose fed-batch protocol, and their expression levels were quantitatively determined by size exclusion HPLC using rhodamine-derivatized biotin. The construct that best fulfilled these criteria contained a 25-mer $Gly_4Ser$ linker [SEQ ID NO:11] with the scFv in the $V_H V_L$ orientation.

TABLE 1

Summary of expression levels of B9E9 scFvSA genetic variants.

| $V_L$—$V_H$—SA Linker type[a] | Expression[b] | $V_H$—$V_L$—SA Linker type | Expression |
|---|---|---|---|
| 15 mer G4S | + | 15 mer G4S | 60 mg/L |
| 18 mer G4S | ++ | 18 mer G4S | 195 mg/L |
| 25 mer G4S | ++ | 25 mer G4S | 300 mg/L |
| 35 mer G4S | ++ | | |
| 18 mer pKOD | 40 mg/L | 18 mer pKOD | 60 mg/L |
| 18 mer pKOD2 | ++ | 18 mer pKOD2 | +++ |

[a]Linker sequences (L1):
15 mer G4S: GGGGSGGGGSGGGGS (SEQ ID NO: 10)
18 mer G4S: GGGGSGGGGSGGGGSGGS (SEQ ID NO: 29)
25 mer G4S: GGGGSGGGGSGGGGSGGGGSGGGGS (SEQ ID NO: 11)
35 mer G4S: 7 copies of GGGGS (SEQ ID NO: 30)
18 mer pKOD: GLEGSPEAGLSPDAGSGS (SEQ ID NO: 9)
18 mer pKOD2: GLEGSPEAGLSPDAGSDS (SEQ ID NO: 31)
[b]The expression levels of the fusion proteins were based on 8L fermentor runs except for those qualitative data, designated as plus symbols, based on SDS-PAGE analysis of shake-flask cultures.

Example V

Increased Expression of scFvSA Fusion Proteins in Periplasm of E. coli

The E. coli fkpA gene is a member of the family of FK506-binding proteins (FKBPs) and is one of the periplasmic components involved in protein folding. It is expressed in the E. coli periplasm and has peptidyl-prolyl isomerase (PPIase) activity. The PPIase-independent chaperone activity of the FkpA gene product has also been demonstrated both in vivo and in vitro. The FkpA chaperone protein is involved in a protein-folding process by stabilizing the folding intermediates in the periplasm. It was tested whether co-expression of the single chaperone gene (fkpA) was able to stimulate the expression of scFvSA fusion proteins, especially among those that had not previously expressed well in E. coli.

Figure 19:
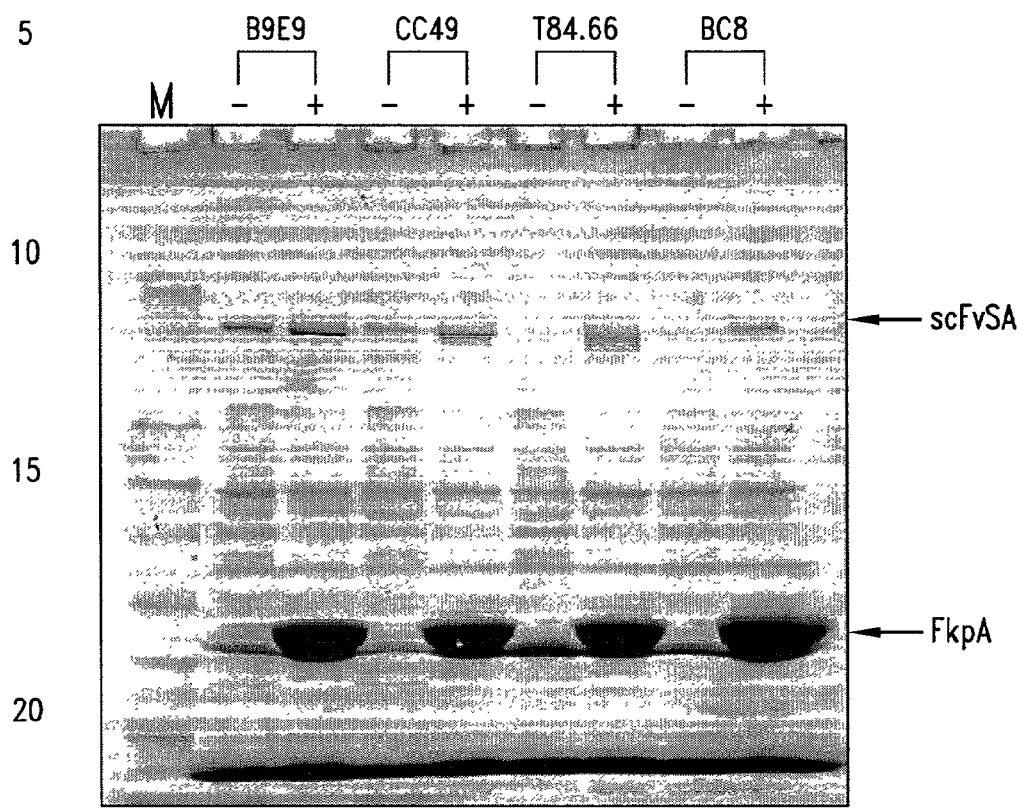
FIG. 19 is a scanned image of SDS-PAGE analysis of scFvSA fusion protein expression in the presence and absence of FkpA.

In order to clone the DNA fragment of the fkpA gene, chromosomal DNA was extracted from E. coli XL1-Blue cells (Stratagene) and digested with XhoI. Thirty-five cycles of PCR were performed using a pair of oligonucleotides (RX1229: ACGACGGTTGCTGCGGCGGTC (SEQ ID NO: 32); RX1231: AGGCTCATFFAAT GATGCGGGT (SEQ ID NO: 33); both obtained from Operon Technologies, Inc.) and 300 ng of the digested genomic DNA as a template. The PCR mixture was subject to a second round of PCR (30 cycles) using a pair of nested oligonucleotides (RX1230: GGATCCAAGCTTACGATCACGGTCATGAACACG (SEQ ID NO: 34); RX1232: CTCGAGAAGCTTTAAC-TAAATTTAATACAGCGGA) (SEQ ID NO: 35). The PCR fragments were resolved on a 1% agarose gel, and the 1.6-kb fragment was isolated. The extracted DNA was cloned into the TA vector (Invitrogen), and the sequence was confirmed by DNA sequencing. The clone was digested with HindIII, using a site that was incorporated into oligonucleotides RX1230 and RX 1232 and was ligated with HindIII-digested vector E84-2-8 (NeoRx Corp.), harboring the anti-CEA T84.66 scFvSA fusion gene (T84.66 cDNA from City of Hope, Duarte, Calif.). The resultant plasmid (F115-1-1) was used to transform XL1-Blue E. coli for shake-flask expression. The periplasmic components were extracted and analyzed on 4–20% SDS-PAGE. For electrophoretic analysis, 20 µl of the solution of scFvSA periplasmic fusion proteins were loaded in each lane of the gel. Following electrophoresis, the gel was stained with Coomassie Blue R250. The FkpA protein, with a molecular weight of about 30,000, was prominently present in all samples carrying the fkpA gene (+), while absent in those lacking the gene (−), as shown, for example, in FIG. 19. The molecular weights of the seven components in the SEEBLUE molecular standard marker (M), obtained from Novex, listed in order of increasing size, from the bottom of the gel, are 16,000; 30,000; 36,000; 50,000; 64,000; 98,000; and 250,000. As seen in FIG. 19, expression of the T84.66 scFvSA fusion protein increased dramatically when co-expressed with the FkpA chaperone protein, in comparison to the parent construct (E84-2-8) lacking the fkpA gene. Additional scFvSA fusions were constructed by moving NcoI-SacI fragments to the F115-1-1 vector, which had previously been restricted with NcoI and SacI. The resultant plasmids were tested in E. coli XL1-Blue shake flask cultures. Upon electrophoretic analysis, several showed increased fusion protein expression, as demonstrated in FIG. 19 and Table 2. The results summarized here involve only the $V_h$-$V_l$-SA fusion configuration incorporating the $(Gly_4Ser)_5$ (SEQ ID NO: 11)linker. As summarized in Table 2, the expression levels of fusion proteins in the shake flask experiments were estimated qualitatively, with the highest level assigned a level of +++++.

TABLE 2

Qualitative expression of scFvSA fusion proteins in E. coli.

| Antigen | scFvSA | SEQ ID NO. | Expression level FkpA⁻ | FkpA⁺ |
|---|---|---|---|---|
| CEA | T84.66 | 36 | − | ++ |
| | Col-1 | 37 | − | + |
| | PR1A3 | 38 | − | − |
| | MFE-23 | 39 | ++++ | ++ |
| | Nrco-2 | 40 | +++ | + |
| Tag-72 | CC49 | 41 | ++ | ++++ |
| MUC-1 | BrE-3 | 42 | − | −+ |
| c-erbB2 | ICR12 | 43 | − | − |
| CD20 | B9E9 | 44 | +++ | +++++ |
| | C2B8 | 45 | − | − |
| CD45 | BC8 | 46 | + | +++ |

Example VI

Purification of huNR-LU-10 scFvSA and B9E9 scFvSA Proteins

The iminobiotin affinity matrix was prepared by reacting epoxide-activated Macro-eprep matrix (BioRad, Hercules Calif.) with 112 µm N-(3-amino-propyl)-1,3 propane diamine (Sigma) per g of matrix in 0.2 M carbonate buffer. The reaction was stopped after 8 h by filtering the slurry through a scintered glass funnel and rinsing the matrix with distilled water. Residual epoxides were inactivated by reacting the matrix with 0.1 M sulfuric acid for 4 h at 80° C., and the matrix was again rinsed. The amine-derivitized matrix was suspended in PBS, and the pH increased to 8.5 by the addition of 10% volume of 0.5 M sodium borate, pH 8.5. NHS-iminobiotin (Pierce) was dissolved in DMSO and added to the suspended matrix at a ratio of 2.6 mg/g of matrix. Following a 4 h reaction, the matrix was rinsed with distilled water followed by several alternating washes with pH 11 sodium carbonate buffer and pH 4 sodium acetate buffer and a final rinse with distilled water. The matrix was stored as a slurry in 20% ethanol.

Cells (650–750 g, wet wt) were washed twice in PBS, resuspended to 10–20% weight per volume with ice-cold 30 mM Tris, 1 mM EDTA, pH 8, and disrupted through two cycles of microfluidization. The lysate was adjusted to 50 mM glycine, 450 mM NaCl, pH 9.6, with a conductivity range of 46–48 mSe per cm, and then centrifuged at 12,000 rpm for 90 min. The supernatant was filtered (0.2 µm), then affinity purified over immobilized iminobiotin. The iminobiotin matrix was packed in a column and equilibrated in 50 mM glycine, 500 mM NaCl, pH 9.6 with a conductivity of 46–48 mSe per cm. Capacity using recombinant streptavidin (Roche Biochemical, Indianapolis, Ind.) was 2 mg per ml of bed volume under a flow of 2 ml/cm$^2$/min. The 0.2 µm filtered cell homogenized supernatant was pumped at room temperature at 2 ml/cm$^2$ per min using 80 ml of bed volume per 100 g of cells. After washing with 20 bed volumes of column equilibrating buffer, the scFvSA fusion protein was eluted with 0.2 M sodium acetate, 0.1 M NaCl, pH 4.0, neutralized with Tris buffer, and then exhaustively dialyzed in refrigerated PBS.

To reduce protein aggregation, purified scFvSA was treated with 10% DMSO for 5–7 h at room temperature and dialyzed in PBS. The purified protein was concentrated using an Amicon YM30 membrane apparatus and filter-sterilized for aseptic storage at 4° C. At concentrations of 2–3 mg/ml, purified preparations typically contained ca. 5–8% aggregate.

Typical recoveries from iminobiotin chromatography were 50–60% with less than 5% appearing in the flow-through and wash. The residual remained as aggregate/entrapped material on the column. Addition of DMSO to the eluting buffer yielded <5% additional purified protein. Use of a variety of ionic and nonionic detergents did not improve recoveries. HPLC size exclusion analysis of the eluted fusion protein showed that up to 40% of the protein was in an aggregated form. Light scattering HPLC indicated aggregate sizes between 400,000 and 4 million. Treatment with 10% DMSO for several hours resulted in the slow de-aggregation of the fusion protein, yielding >92% tetrameric species that remained so when stored refrigerated in PBS at a concentration of <3 mg/mL.

Example VII

Biochemical Characterization of huNR-LU-10 scFvSA and B9E9 scFvSA Proteins

SDS-PAGE Analysis. Purified fusion proteins were analyzed on 4–20% Tris-glycine SDS-PAGE gels (Novex, San Diego, Calif.) under nonreducing conditions. Before electrophoresis, samples were mixed with SDS-loading buffer and incubated at either room temperature or 95° C. for 5 min. Gels were stained with Coomassie blue.

Figure 12:
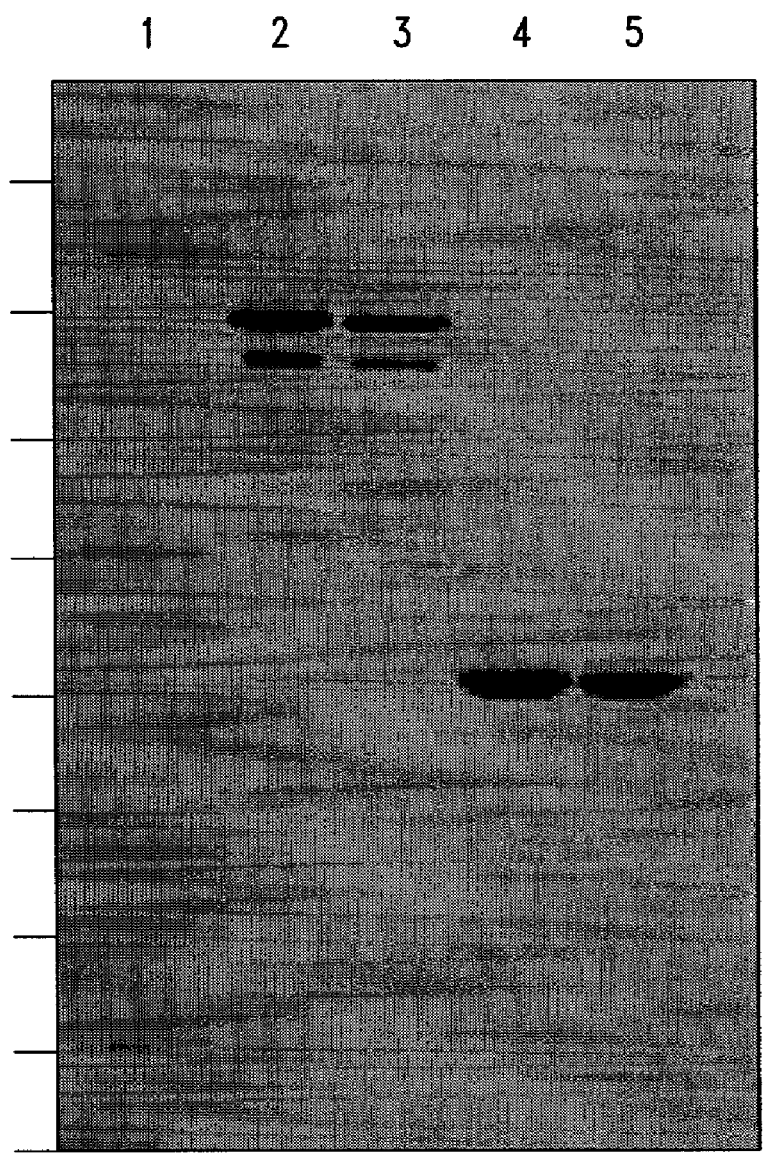
FIG. 12 is a scanned image representing SDS-PAGE analysis of huNR-LU-10 scFvSA.

SDS-PAGE demonstrated that the fusion proteins were purified to >95% homogeneity after iminobiotin chromatography (FIG. 12, lanes 2 & 3; huNR-LU-10 data only). The major band migrated at the expected molecular weight of ~173 kDa with minor isoforms evident. These isoforms were also detected with polyclonal anti-streptavidin antibody on Western gel analysis (data not shown). However, all bands resolved into a single species of ~43 kDa when the protein was boiled prior to electrophoresis, consistent with a single protein entity dissociable into its homogeneous subunit (FIG. 12, lanes 4 & 5). The molecular weights of the seven components in the SEEBLUE molecular standard marker (FIG. 12, lane 1), available from Novex, are described in Example V.

Size exclusion HPLC and Laser Light Scattering Analysis. Purified protein preparations were analyzed by size exclusion HPLC performed on a ZORBAX_GF-250 column with a 20 mM sodium phosphate/0.5 M NaCl mobile phase. The molecular weight of the fusion construct was measured using this ZORBAX system connected in series with a Varian™ STAR 9040 refractive index detector and a MiniDawn light scattering instrument (Wyatt Technologies, Santa Barbara, Calif.). A dn/dc value of 0.185 for a protein in an aqueous buffer solution was used in the molecular weight calculations.

Figure 13:
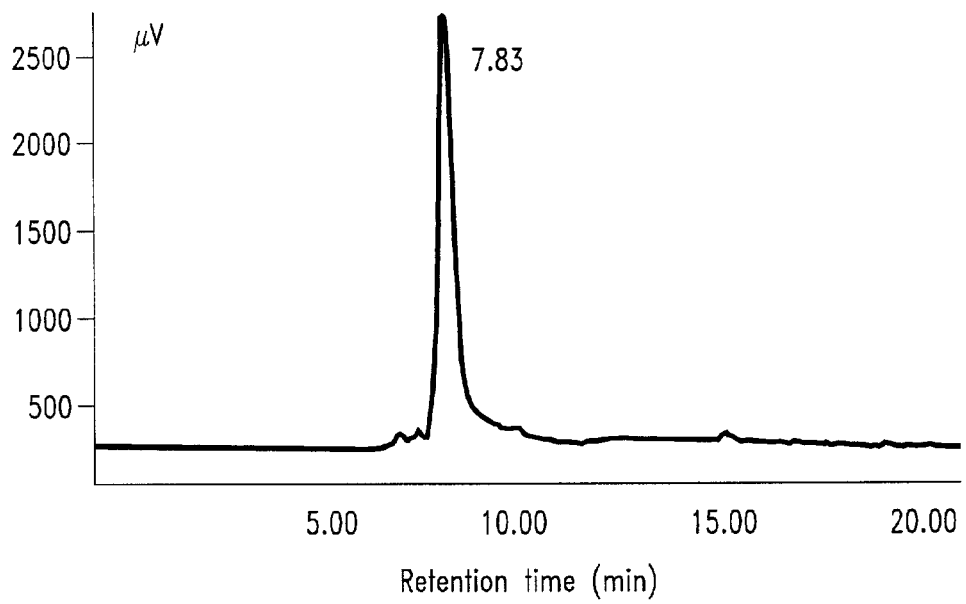
FIG. 13 is a graphic representation of size exclusion HPLC analysis of huNR-LU-10 scFvSA.

HPLC size exclusion chromatography exhibited a major peak with a retention time appropriate for the huNR-LU-10 tetramer with a minor (<8%) aggregate peak (FIG. 13). B9E9 scFvSA showed a very similar profile (graph not shown). These analyses demonstrated that all of the purified protein was tetrameric or an aggregate thereof. Light scattering analysis of huNR-LU-10 scFvSA indicated a molecular weight of 172,600, as predicted for the tetrameric protein.

Amino-terminal sequencing. Automated amino acid sequencing was performed using a PROCISE 494 sequenator (Applied Biosystems, Inc., Foster City, Calif.). This revealed that the leader sequences of both huNR-LU-10 scFvSA and B9E9 scFvSA were cleaved at the expected signal peptidase site adjacent to the first amino acid of the variable region.

Molecular weight determination of B9E9 scFvSA. Liquid chromatographic separation was conducted with an Hewlett Packard series 1100 system, fitted with a JUPITER C18 column (300 Å, 3.2×50 mm, 5µ) and C18 "SafeGuard" column (Phenomenex, Torrance, Calif.) at a flow rate of 500 µl/min. The mobile phase was composed of water/1% formic acid (buffer A) and acetonitrile/1% formic acid (buffer B). The gradient applied was 2% B for 3 mm rising to 99% B within 7 mm. B9E9 scFvSA (10 µl) was eluted at a retention time of 8.7 mm. The analytical column was interfaced with a Thermoquest/Finnigan ESI LCQ ion trap mass spectrometer (San Jose, Calif.). The instrument was calibrated with myoglobin and operated in the positive ion mode with the heated capillary set to 200° C. and 5.1 kV applied to the electrospray needle. The data were acquired in a full scan MS mode (m/z [500–2000 Da/z]) using automated gain control with 3 microscans and a maximum ion time of 500 ms.

The mass spectrum of the B9E9 monomer showed a deconvoluted molecular weight of 43,401, which is in agreement with the calculated most abundant mass of 43,400.

Figure 14:
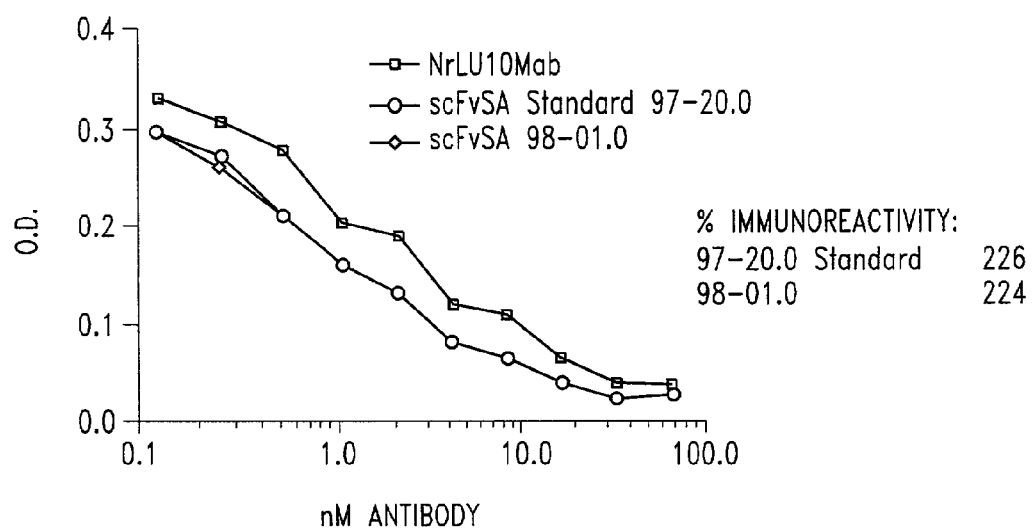
FIG. 14 is a plot illustrating a competitive immunoreactivity assay of huNR-LU-10 scFvSA (97-20.0 and 98-01.0) as compared to huNR-LU-10 mAb.

HuNR-LU-10 Competitive Immunoreactivity ELISA. Serial dilutions of the humanized NR-LU-10 whole antibody or the huNR-LU-10 fusion protein were allowed to compete with peroxidase-labeled murine NR-LU-10 whole antibody for binding to an 0.1% NP40 membrane extract from the human carcinoma cell line, LS-174 (ATCC #CL188). Following a log-logit transformation of the data in which curves were fit to the same slope, the concentration of competitor antibody that gave 50% inhibition (k) was calculated. Percent immunoreactivity was determined according the formula: k (fusion protein standard)/k (whole antibody standard)×100. The huNR-LU-10 fusion protein was found to possess immunoreactivity superior (~225%) to the intact divalent humanized antibody (FIG. 14).

B9E9 Competitive Immunoreactivity FACS Assay. Immunoreactivity was assessed in a competitive binding assay using flow cytometry that measured the binding of fluorescein-labeled B9E9 to the CD20-positive Ramos cell line (Burkitt's lymphoma; ATCC CRL-1596) in the presence of various concentrations of unlabeled antibody. B9E9 mAb was labeled using fluorescein N-hydroxysuccinimidate, and an optimized amount of this conjugate was mixed with serial dilutions (3–200 ng/ml) of B9E9 mAb standard or molar equivalents of B9E9 scFvSA and incubated with $1\times10^6$ cells at 4° C. for 30 minutes. Samples were washed and then analyzed on a single laser FACSCalibur (Becton Dickinson). After gating on single cells, the geometric mean fluorescence intensity was determined from a histogram plot of fluorescence. The concentration of competitor antibody required for 50% inhibition ($IC_{50}$) of fluorescein-B9E9 binding was calculated using nonlinear regression analysis for one-site binding. Percent immunoreactivity=[$IC_{50}$ scFvSA/$IC_{50}$ mAb]×100.

The scFvSA was about twice as immunoreactive (~185%) as the divalent B9E9 antibody on a molar basis, and nearly equivalent (~93%) to B9E9 mAb when adjusted for tetravalency (graph not shown).

B9E9 scFvSA Avidity. Avidity was determined using saturation binding experiments that measure specific binding of radiolabeled mAb or fusion protein (0.025–50 ng/ml) at equilibrium in the presence of excess antigen ($10^7$ cells). Nonspecific binding was determined in the presence of excess cold mAb or fusion protein (50 µg/ml). Mixtures were incubated and centrifuged as described above. The equilibrium dissociation constant (Kd) was calculated from nonlinear regression analysis of nM bound vs. nM radioligand using immunoreactivity-adjusted antibody concentrations. The B9E9 fusion protein retained the same relative nanomolar avidity as the B9E9 mAb, as determined by radiolabeled binding to Ramos cells (Table 3).

TABLE 3

Avidity of B9E9 mAb and scFvSA fusion protein.

| Antibody | $K_d$ (nM)[a] | $K_a$ (× $10^8 M^{-1}$) |
|---|---|---|
| B9E9 mAb | 9.75 | 1.02 |
| B9E9 scFvSA (25-mer) | 12.44 | 0.80 |

[a]Antibody concentrations were adjusted for immunoreactivity (67% and 79% for mAb and scFvSA, respectively). $K_d$ and $K_a$ were calculated using nonlinear regression analysis of nM bound vs. nM radioligand.

Biotin Binding and Dissociation. Biotin binding capacity was determined by incubation of a known quantity of fusion protein with a 9-fold molar excess of [3H]biotin (NEN Research Products, Boston, Mass.). After removal of uncomplexed biotin using streptavidin-immobilized beads (Pierce Chemical; Rockford, Ill.), the amount of [$^3$H]biotin associated with the fusion protein was determined.

HuNR-LU-10 scFvSA and B9E9 scFvSA were capable of binding an average of 3.0 and 3.6 biotins, respectively, as compared to 4 biotin binding sites for recombinant streptavidin.

Figure 15:
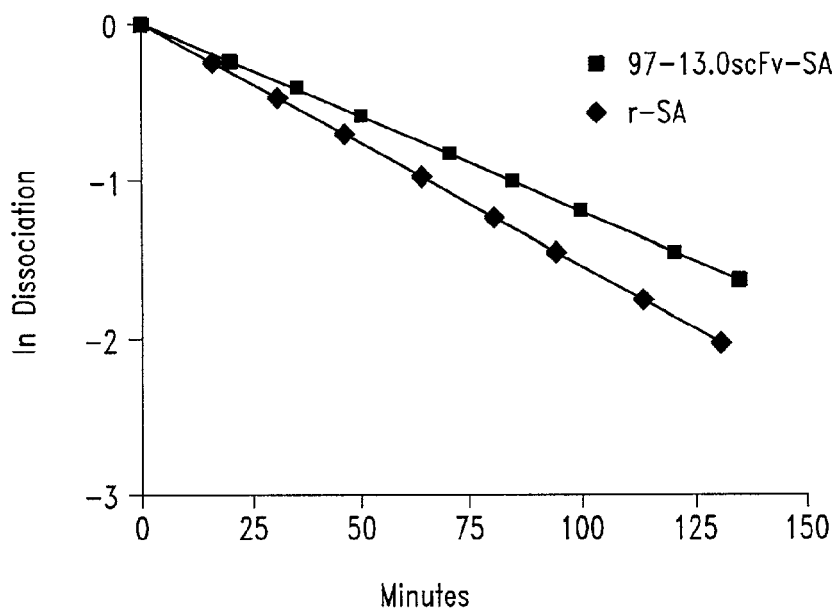
FIG. 15 is a plot illustrating the rate of dissociation of DOTA-biotin from huNR-LU-10 scFvSA (97-13.0) as compared to recombinant streptavidin (r-SA).

For huNR-LU-10 scFvSA, the rate of DOTA-biotin dissociation was assessed at 37° C. in 0.25 M phosphate, 0.15 M sodium chloride, pH 7.0 containing either 10 µM fusion protein or recombinant streptavidin and a subsaturating level of [$^{90}$Y]DOTA-biotin. A 100-fold saturating level of biocytin (Sigma) was added to initiate the dissociation measurement. At timed intervals, aliquots of incubate were diluted in PBS containing 0.5% bovine serum albumin. In order to precipitate the protein, zinc sulfate was added to each diluted aliquot, followed by sodium hydroxide, each to yield a final concentration of 0.06 M. Following microcentrifugation, free [$^{90}$Y]DOTA-biotin in the supernatant was assessed using a Hewlett Packard beta counter. The DOTA-biotin dissociation rate of huNR-LU-10 scFvSA was comparable to that of recombinant streptavidin ($t_{1/2}$ of 58 min for huNR-LU-10 scFvSA vs. 47 min for recombinant streptavidin; FIG. 15).

For B9E9 scFvSA, biotin dissociation was measured as described above, except [$^3$H]biotin was used instead of [$^{90}$Y]DOTA-biotin. The calculated $t_{1/2}$ for biotin dissociation was 379 min for B9E9 scFvSA vs. 364 min for recombinant streptavidin (graph not shown).

Example VIII

Analysis of Biodistribution of $^{111}$In-DOTA-Biotin After Pretargeting with huNR-LU-10 scFvSA The expressed huNR-LU-10 scFvSA gene fusion was tested in a full pretarget protocol in female nude mice bearing SW-1222 human colon cancer xenografts (100–200 mg), subcutaneously implanted on the right flank. In these experiments, 575 µg of $^{125}$I-labeled fusion protein was injected intravenous (iv) and allowed to circulate for 18 hours prior to iv injection of 100 µg of synthetic clearing agent (sCA) (See e.g., PCT Publication Nos. WO 97/46098 and WO 95/15978). Three hours after the sCA injection, there was an injection of 1.0 µg of $^{111}$In-DOTA-biotin, essentially a chelating agent containing a radionuclide, conjugated to biotin (see U.S. Pat. Nos. 5,578,287 and 5,608,060). Mice were sampled for blood, then sacrificed and dissected at 2, 24, 48, and 120 hours after $^{111}$In-DOTA-biotin injection.

The concentration of $^{125}$I-huNR-LU-10 scFvSA radioactivity in blood and most well-perfused soft tissues was very low, due to the low blood pool concentration induced by the sCA complexation and subsequent hepatic clearance. The exceptions were liver and tumor. Liver uptake and retention of fusion protein was due to the mechanism of clearing agent action, and the somewhat retarded degradation of the streptavidin-containing fusion protein, which was consistent with similar results observed in studies of both streptavidin and the chemical conjugate of huNR-LU-10 and streptavidin (huNR-LU-10/SA) (data not shown). The $^{125}$I-huNR-LU-10 scFvSA exhibited evidence of in vivo immunoreactivity by the retention of relatively high radiolabel concentration at the tumor (both stoichiometrically and relative to blood pool concentration) at all time points. The ratio of tumor concentration to blood concentration continuously increased from 23 to 143 hours. The lower blood pool values induced by clearing agent have led to a dramatic increase in the ratio, achieving average values over twice those observed in the absence of clearing agent (data not shown).

Figure 16:
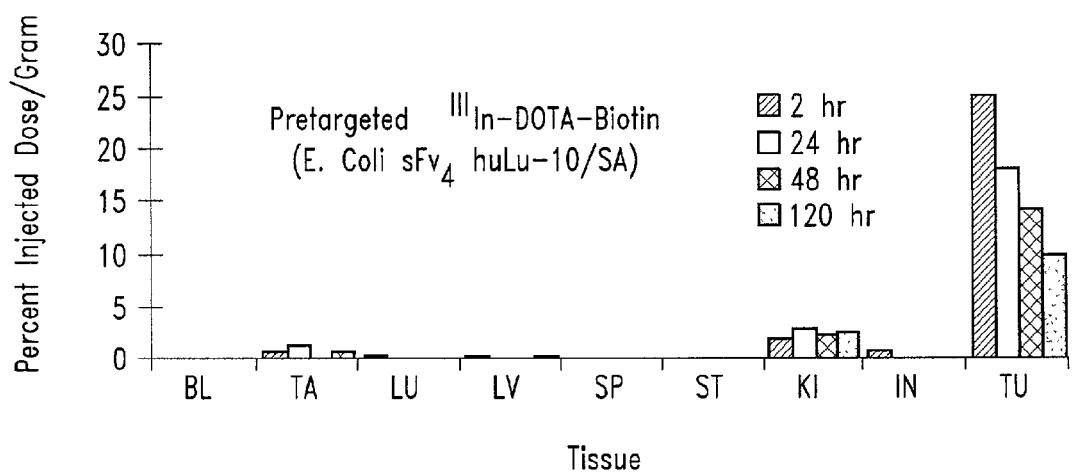
FIG. 16 is a graph illustrating biodistribution of pretargeted huNR-LU-10 scFvSA.

The pretargeted $^{111}$In-DOTA-biotin biodistribution is shown in FIG. 16. Consistent with pretargeting results employing the chemical conjugate huNR-LU-10/SA, the concentration of $^{111}$In-DOTA-biotin radioactivity in blood and all non-xenograft soft tissues was very low. Despite the high concentrations of fusion protein in the liver noted above, $^{111}$In-DOTA-biotin uptake and retention in this organ was not evident, indicating that the fusion protein had been efficiently internalized and was unavailable to bind the subsequently administered radiobiotin. The highest concentration of $^{111}$In-DOTA-biotin was at the tumor at all time points. (The tissues in order in FIG. 16 are blood, tail, lung, liver, spleen, stomach, kidney, intestine, and tumor.) The rapid uptake, achieving peak concentrations at the earliest time point sampled, is a hallmark of pretargeting. Efficient, consistent delivery and retention of $^{111}$In-DOTA-biotin at the tumor was also observed. Peak concentrations of $^{111}$In- DOTA-biotin at the tumor were within the range consistently achieved by use of the chemical NR-LU-10/SA conjugate (20–25% injected dose/g) (data not shown).

Example IX

Figure 17:
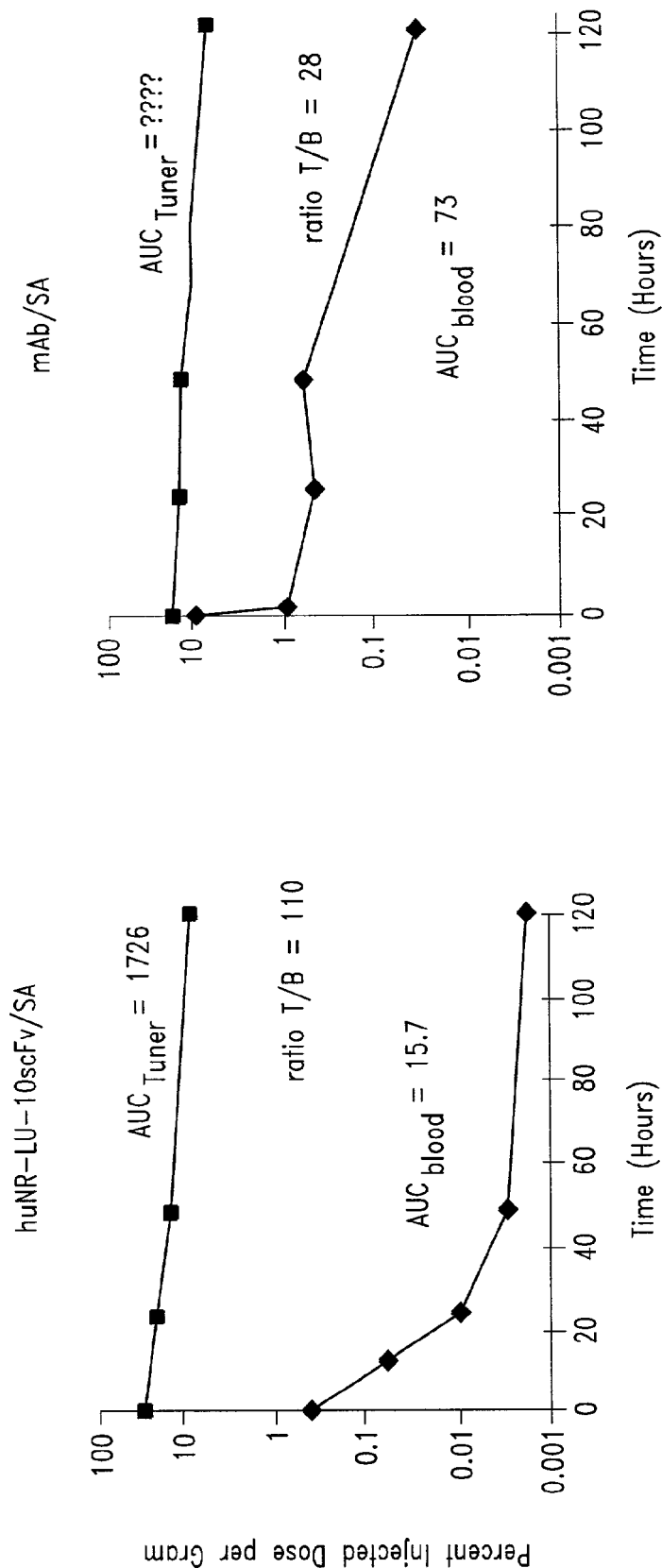
FIG. 17 is a graph depicting blood clearance and tumor uptake of huNR-LU-10 scFvSA versus a chemically conjugated form (mAb/SA).

Analysis of Blood Clearance and Tumor Uptake of huNR-LU-10 scFvSA Versus huNR-LU-10/Streptavidin Chemical Conjugate Tumor to blood ratios of huNR-LU-10 scFvSA increased from nearly 100, two hours after DOTA-biotin injection, to several thousand by 24 hours. Comparative results for the huNR-LU-10/SA chemical conjugate and fusion protein, showing the efficiency of radiobiotin delivery to tumor and corresponding area-under-the-curve (AUC) values for blood, and tumor are shown in FIG. 17.

The overall tumor AUC using the fusion protein was somewhat less than that of the chemical conjugate (1726, for the time interval between 0–120 hours, versus 2047 for a typical chemical conjugate experiment). However, there was a dramatic difference in the concentration of $^{111}$In-DOTA-biotin in the blood pool, with the concentration in the fusion protein group consistently lower at all time points. The greatest ramification of this decreased retention of radioactivity in the blood is that animals treated with the fusion protein experience a higher therapeutic index (tumor/blood) than those treated with the chemical conjugate.

Example X

Pretargeted Biodistribution of B9E9 scFvSA

Pretargeted radioimmunotherapy studies were conducted in female nude mice bearing well-established Ramos human cancer xenografts (100–400 mg). Tumored Bk1:BALB/c/nu/nu nude mice were obtained by implanting 5–25×10$^6$ cultured cells subcutaneously in the side midline 10–25 days prior to study initiation. Mice received intravenous injections of the $^{125}$I-labeled B9E9 scFvSA (600 µg), and 20 hours later were injected intravenously with 100 µg of synthetic clearing agent. $^{111}$In-labeled DOTA-biotin (1.0 µg) was injected intravenously into each mouse 4 hours after clearing agent. Groups of three mice per time point were bled and sacrificed at 2, 24, and 48 hours after injection of $^{111}$In-DOTA-biotin. Whole organs and tissue were isolated, weighed, and counted for radioactivity using a gamma counter.

Figure 18:
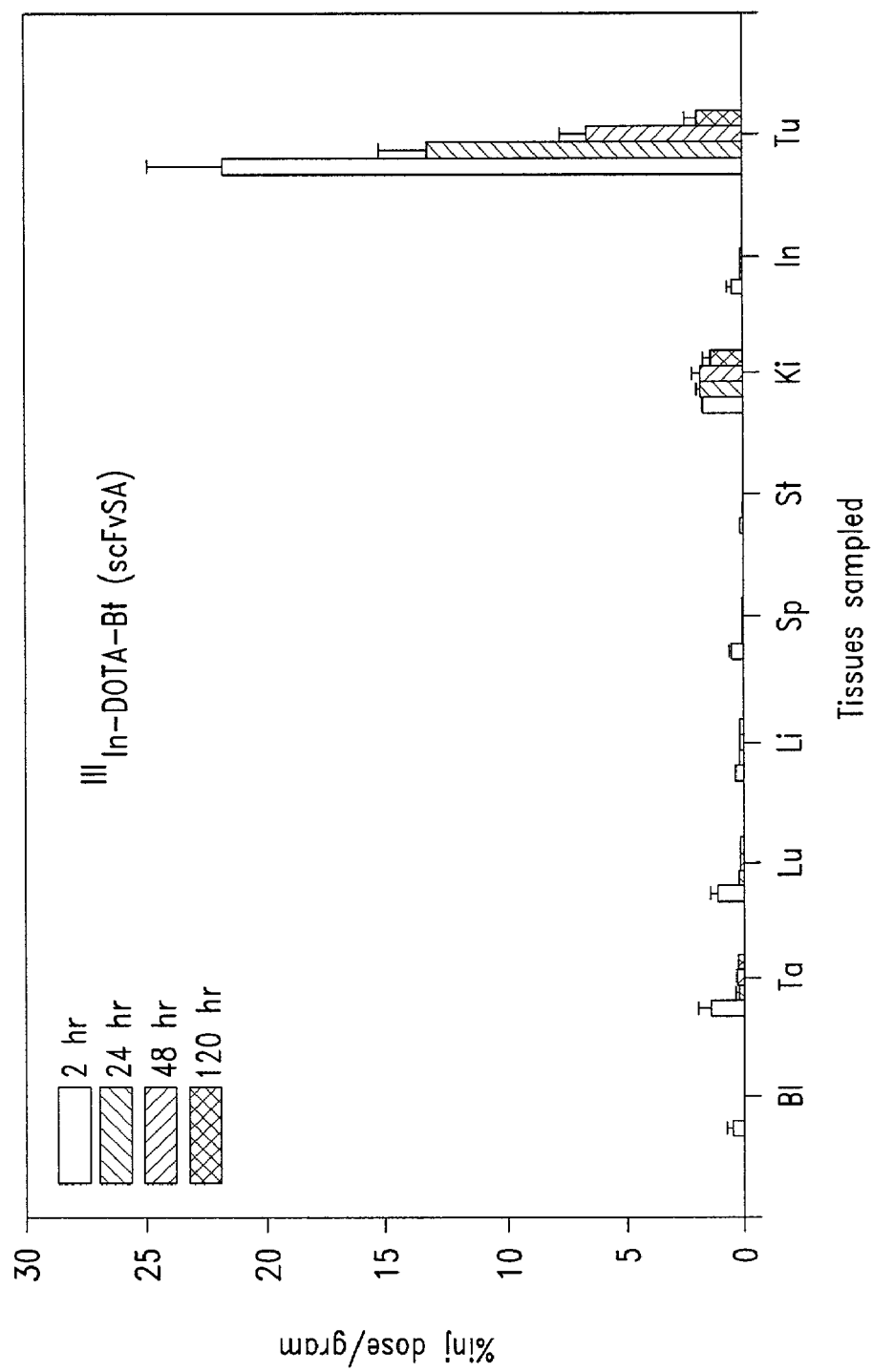
FIG. 18 is a bar graph illustrating biodistribution of pretargeted B9E9 scFvSA.

As shown in FIG. 18, the $^{111}$In-DOTA-biotin radioactivity in blood and all non-xenograft soft tissues was below 2% of the injected dose/g. Further, $^{111}$In-DOTA-biotin uptake and retention in liver is not seen, indicating that the fusion protein has been efficiently internalized by the liver, via the added clearing agent, and is unavailable to bind the subsequently administered radiobiotin. Stable delivery and retention of $^{111}$In-DOTA-biotin at the tumor were observed. The highest concentration of radiobiotin at all time points was at the tumor (both stoichiometrically and relative to blood pool concentration). Peak concentrations of $^{111}$In-DOTA-biotin at the tumor were 17–24% of injected dose/g (mean 21.66, s.d. 3.17). Tumor to blood ratios increased from about 90, 2 hours after DOTA-biotin injection, to greater than 700 by 24 hours. In these experiments no effort was made to optimize the dose of the fusion protein, clearing agent, or DOTA-biotin, nor was any effort made to optimize the schedule of administration of these components. (In FIG. 18, the tissues in order are blood, tail, lung, liver, spleen, stomach, kidney, intestine, and tumor.)

Example XI

Figure 20:
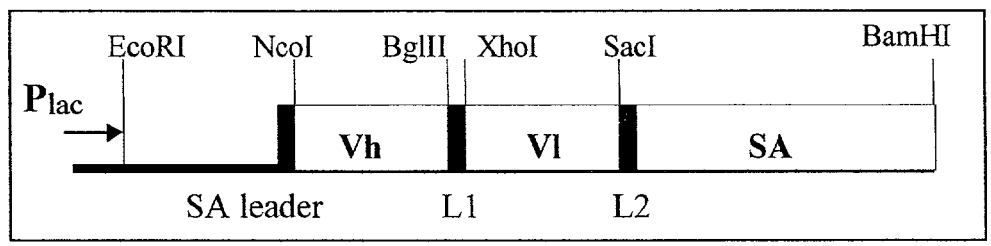
FIG. 20 is a schematic representation of a CC49 single chain antibody scFvSA fusion.

Construction of Anti-TAG-72 CC49 Single Chain Antibody-Genomic Streptavidin Fusion The murine CC49 single chain Fv/streptavidin (scFvSA) fusion protein is expressed from the genetic fusion of the single chain antibody of the variable regions (scFv) to the genomic streptavidin of *Streptomyces avidinii*. The scFv gene comprises the variable regions of the heavy ($V_H$) and light ($V_L$) chains separated by a DNA linker sequence (e.g., FIG. 20). The streptavidin coding sequence is joined to the 3' terminus of the scFv gene, and the two genes are separated in-frame by a second DNA linker sequence. The signal sequence from the streptavidin gene is fused at the 5' terminus of the scFvSA gene to direct expression to the *E. coli* periplasmic space. The scFvSA gene is under control of the lac promoter, and the expressed fusion protein is extracted and purified from *E. coli* and forms a soluble tetramer of about 176,000 molecular weight.

The cDNA sequences of the murine CC49 heavy chain (Vh) and light chain (Vl) were obtained from the GENBANK database (accession numbers L14549 and L14553, respectively) and were further optimized based on *E. coli* codon usage. The scFvSA fusion gene consists of the Vh and Vl regions, which are separated by a 25-mer Gly4Ser linker (SEQ ID NO: 11), fused to the genomic streptavidin coding region.

Figure 21:
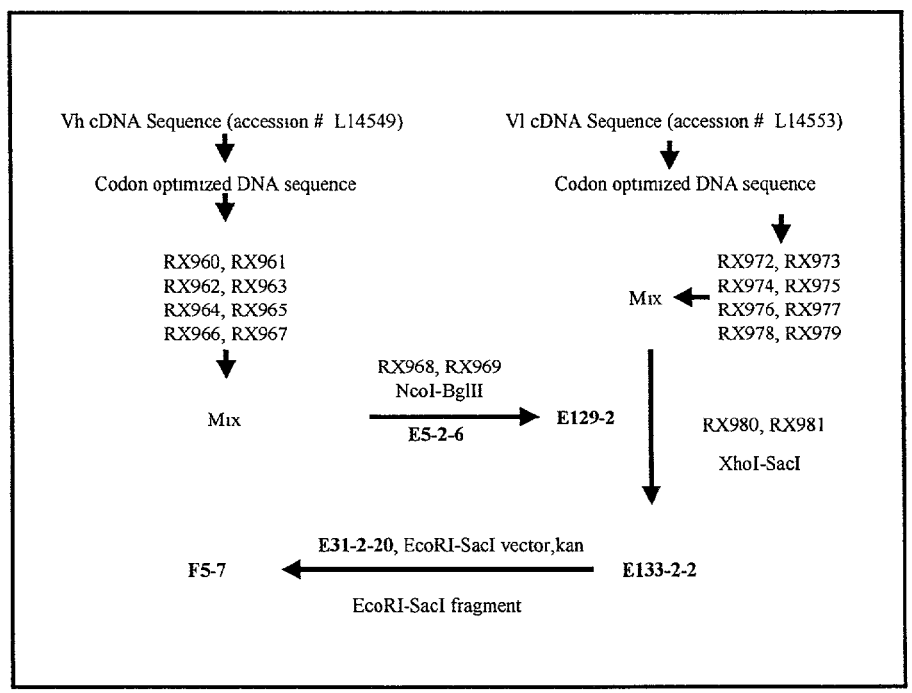
FIG. 21 is a schematic representation of the construction of the F5-7 CC49 expression plasmid.

Pairwise oligos such as RX960-RX961, RX962-RX963, etc. (see list below) were annealed together using 5 cycles of the following polymerase chain reaction (PCR) protocol (95° C. for 45 sec; 50° C. for 45 sec; 74° C. for 1 mm with Pfu polymerase). The products were passed through CENTRISEP columns (Princeton Separations) to desalt. Five µl of each of the PCR products were combined as templates, and 30 cycles of PCR were performed using RX968 and RX969 oligonucleotides for the heavy chain or RX980 and RX981 for the light chain. The PCR products were purified on a 1.5% agarose gel, and the DNAs were extracted. The PCR products were digested with restriction enzymes as indicated in FIG. 21 at 37° C. overnight, and the mixture was desalted on CENTRISEP columns. The heavy chain fragment was cloned in NcoI/BglII-digested vector E5-2-6 to generate the E 129-2, and the light chain fragment was cloned in XhoI/SacI-digested vector E129-2 to generate E133-2-2. The EcoRI-SacI fragment containing murine scFv of CC49 was excised from the E 133-2-2 plasmid and cloned into E31-2-20 vector containing a kanamycin-resistant neo gene. The resultant F5-7 plasmid expressed the murine CC49 scFvSA fusion gene and exhibited kanamycin resistance when transformed into *E. coli*. The DNA and amino acid sequences of CC49 scFvSA (plasmid F5-7) are shown in FIG. 22.

The host organism is *E. coli* XL1-Blue, which has the genotype recA1 endA1 gyrA96 thi-1 hsdR17 supE44 relA1 lac [F' proAB lacI$^q$ZΔM15 Tn10 (Tet$^r$)]The organism was purchased from Stratagene (La Jolla, Calif.), frozen at −70° C. as DNA competent cells, and the manufacturer's directions were followed to perform the transformation. Aliquots (50 L) were plated on LB agar containing 50 µg per mL kanamycin, and were incubated for 2 days at 30° C. One colony was streaked for isolation on an LB plus kanamycin plate. The final construct is plasmid F5-7 in *E. coli* strain XL1-Blue.

All nucleotide primers, as listed below, were synthesized by Operon Technologies, Inc. (Alameda, Calif.).

RX960
CAGGTTCAGT TGCAGCAGTC TGATGCTGAA    (SEQ ID NO:50)
TTGGTGAAAC CGGGTGCTTC AGTGAAAATT

RX961
TGCATGATCG GTGAAGGTGT AGCCAGAAGC    (SEQ ID NO:51)
TTTGCAGGAA ATTTTCACTG AAGCACCCGG

RX962
TACACCTTCA CCGATCATGC AATTCATTGG    (SEQ ID NO:52)
GTGAAACAGA ACCCGGAACA GGGCCTGGAA

RX963
TTTGAAATCA TCATTACCCG GAGAGAAATA    (SEQ ID NO:53)
ACCAATCCAT TCCAGGCCCT GTTCCGGGTT

RX964
CCGGGTAATG ATGATTTCAA ATACAATGAA    (SEQ ID NO:54)
CGTTTCAAAG GCAAAGCCAC GCTGACCGCA

RX965
GCTGTTGAGC TGCACGTAGG CGGTGCTGGA    (SEQ ID NO:55)
GGATTTATCT GCGGTCAGCG TGGCTTTGCC

RX966
GCCTACGTGC AGCTCAACAG CCTGACGTCT    (SEQ ID NO:56)
GAAGATTCTG CAGTGTATTT CTGTACGCGT

RX967
GACTGAGGTA CCTTGACCCC AGTAGGCCAT    (SEQ ID NO:57)
ATTCAGGGAA CGCGTACAGA AATACACTGC

RX968
GAATTCCCAT GGCTCAGGTT CAGTTGCAGC    (SEQ ID NO:58)
AGTCT

RX969
CACCAGAGAT CTTGGAGACG GTGACTGAGG    (SEQ ID NO:59)
TACCTTGACC CCA

RX972
GATATTGTGA TGTCACAGTC TCCGTCCTCC    (SEQ ID NO:60)
CTACCGGTGT CAGTTGGCGA AAAAGTTACC

RX973
ACCACTATAT AAAAGGCTCT GACTGGATTT    (SEQ ID NO:61)
GCAGCTCAAG GTAACTTTTT CGCCAACTGA

RX974
CAGAGCCTTT TATATAGTGG TAATCAGAAA    (SEQ ID NO:62)
AACTACTTGG CCTGGTACCA GCAGAAACCG

RX975
AGCGGATGCC CAGTAAATCA GCAGTTTCGG    (SEQ ID NO:63)
AGACTGACCC GGTTTCTGCT GGTACCAGGC

RX976
CTGATTTACT GGGCATCCGC TCGTGAATCT    (SEQ ID NO:64)
GGGGTCCCGG ATCGCTTCAC CGGCAGTGGT

RX977
TTTCACACTG CTGATGGAGA GGGTGAAATC    (SEQ ID NO:65)
GGTCCCAGAA CCACTGCCGG TGAAGCGATC

RX978
CTCTCCATCA GCAGTGTGAA AACCGAAGAC    (SEQ ID NO:66)
CTGGCAGTTT ATTACTGTCA GCAGTATTAT

RX979
CACCAGTTTG GTCCCAGCAC CGAACGTGAG    (SEQ ID NO:67)
CGGATAGCTA TAATACTGCT GACAGTAATA

RX980
CGGCGGCTCG AGCGATATTG TGATGTCACA    (SEQ ID NO:68)
GTCT

RX981
GAGCCAGAGC TCTTCAGCAC CAGTTTGGTC    (SEQ ID NO:69)
CCAGCACC

Example XII

Expression and Purification of CC49 scFvSA Protein

Transformants of *E. coli* strain XL1-Blue containing plasmid F5-7 (CC49 scFvSA) were grown overnight at 30° C. in Terrific broth (20 ml; Sigma) containing kanamycin (50 µg/ml). The culture was diluted 100-fold into fresh medium and grown in a shaking incubator at 30° C. When the culture attained an $A_{600}$ of 0.3–0.5, IPTG (Amersham Pharmacia Biotech, Piscataway, N.J.) was added to a final concentration of 0.2 mM, and incubation was continued overnight. Periplasmic extracts were prepared for qualitative analysis of the scFvSA expression level. Cells were resuspended in an ice-cold solution of 20% sucrose, 2 mM EDTA, 30 mM Tris, (pH 8.0), and lysozyme (2.9 mg/ml) and were incubated on ice for 30 min. Supernatants were analyzed on 4–20% Tris-glycine SDS-PAGE gels (Novex) under non-reducing, non-boiled conditions, and gels were stained with Coomassie Blue.

Clones were further grown in an 8L fermentor and analyzed for expression level. The primary inoculum (50 ml) was grown overnight at 30° C. in shake flasks containing Terrific broth plus 50 µg/ml kanamycin. The culture was then diluted 100-fold into the same medium and grown at 30° C. for an additional 4–5 h. This secondary inoculum (0.5 liter) was transferred to a 14 liter BIOFLO 3000 fermentor (New Brunswick Scientific) containing 8 liters of complete *E. coli* medium (essentially as as previously described above with respect to B9E9 scFvSA). Cells were harvested at 48 h post-inoculation in a continuous flow centrifuge (POWER-FUGE PILOT, Carr Separations, Franklin, Mass.), washed with PBS (10 mM sodium phosphate, 150 mM NaCl, pH 7.2), and pelleted by centrifugation. A typical fermentation produced 80–90 g of cells (wet wt) per liter culture medium.

For determining expression levels, cells were washed twice in PBS, resuspended to the original volume, and disrupted either by sonication on ice (Branson Ultrasonics, Danbury, Conn.) or through two cycles of microfluidization (Microfluidics International, Newton, Mass.). A rhodamine-biotin HPLC assay was used for quantitating fusion protein in the supernatent of a centrifuged sample of crude lysate, as described previously as described previously in Example VI, above and in Schultz et al., *Cancer Res.* 60:6663–9, 2000). The concentration of fusion protein in the crude lysate was calculated by comparison to a standard analyzed under the same conditions. The molar extinction coefficient for the fusion protein standard was calculated using a previously described method summing the relative contributions of amino acids absorbing at 280 nm (Gill and von Hippel, *Analyt. Chem.* 182:319–326, 1989). Expression levels of CC49 scFvSA in fermentor-grown cells were 100–130 mg/liter.

The iminobiotin affinity matrix was prepared as described previously in Example VI, above and in Schultz et al., *Cancer Res* 60:6663–9, 2000. The fusion protein was purified from *E. coli* cells (650–750 g) by iminobiotin affinity chromatography as described above.

Typical recoveries from iminobiotin chromatography were 50–60% with less than 5% appearing in the flow-through and wash. The residual remained as aggregate/entrapped material on the column.

Example XIII

Biochemical Characterization of CC49 scFvSA Protein

The CC49 scFvSA is secreted into the periplasm of genetically engineered *E. coli* as monomeric subunits (43, 952 Daltons) that spontaneously fold into a tetrameric protein with a molecular weight of 175,808 Daltons. The tetrameric fusion protein contains four antigen binding sites and four biotin binding sites.

Figure 23:
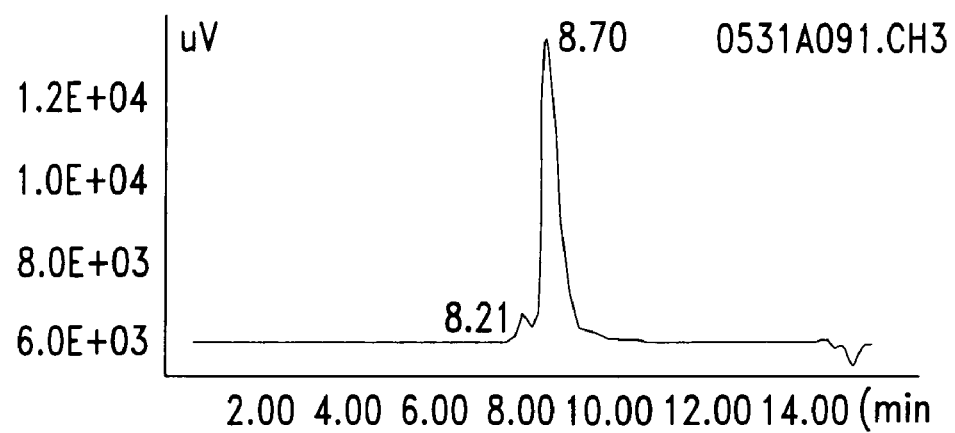
FIG. 23 is a graphical representation of size exclusion HPLC analysis of CC49 scFvSA.

Size exclusion HPLC. Purified protein preparations were analyzed by size exclusion HPLC performed on a ZORBAX GF-250 column with a 20 mM sodium phosphate/0.5 M NaCl mobile phase. The eluent is monitored at 254 nm. FIG. 23 shows the HPLC chromatogram of iminobiotin-purified CC49 scFvSA. The peak at retention time 8.70 minutes is the tetrameric fusion protein with a 5% aggregate eluting at 8.21 minutes. This analysis demonstrated that all of the purified protein was tetrameric or an aggregate thereof.

SDS-PAGE Analysis. Purified CC49 scFvSA was analyzed on 4–20% Tris-glycine SDS-PAGE gels (Novex, San Diego, Calif.) under nonreducing conditions. Before electrophoresis, samples were mixed with SDS-loading buffer and incubated at either room temperature or 95° C. for 5 min. Gels were stained with Coomassie blue.

Figure 24:
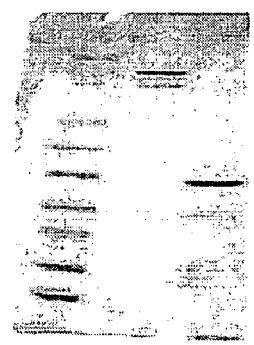
FIG. 24 is a scanned image representing SDS-PAGE analysis of CC49 scFvSA.

SDS-PAGE demonstrated that the fusion protein was purified to >95% homogeneity after iminobiotin chromatography (FIG. 24, lane 2). The major band migrated at the expected molecular weight of ~176 kDa with minor isoforms evident. However, all bands resolved into a single species of ~44 kDa when the protein was boiled prior to electrophoresis, consistent with a single protein entity dissociable into its homogeneous subunit (FIG. 24, lane 3).

Molecular weight determination. Liquid chromatographic separation was conducted with an Hewlett Packard series 1100 system, fitted with a JUPITER C18 column (300 Å, 3.2×50 mm, 5µ) and C18 "SafeGuard" column (Phenomenex, Torrance, Calif.) at a flow rate of 500 µl/mm. The mobile phase was composed of water/1% formic acid (buffer A) and acetonitrile/1% formic acid (buffer B). The gradient applied was 2% B for 3 mm rising to 99% B within 7 mm CC49 scFvSA (10 µl) was eluted at a retention time of 6.8 mm. The analytical column was interfaced with a Thermoquest/Finnigan ESI LCQ ion trap mass spectrometer (San Jose, Calif.). The instrument was calibrated with myoglobin and operated in the positive ion mode with the heated capillary set to 200° C. and 5.1 kV applied to the electrospray needle. The data were acquired in a full scan MS mode (m/z [500–2000 Da/z]) using automated gain control with 3 microscans and a maximum ion time of 500 ms, performed essentially as described in Example VII above.

Figure 25:
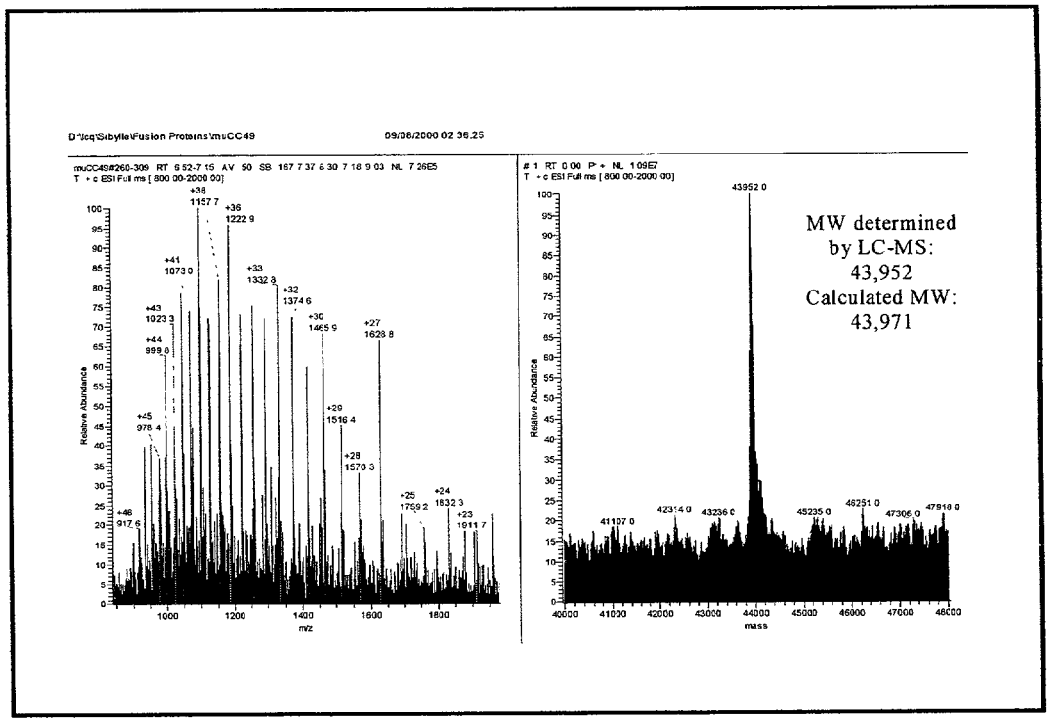
FIG. 25 is a graphical representation of liquid chromatography/electrospray mass spectrometry of CC49 scFvSA.

The mass spectrum of the CC49 monomer showed a deconvoluted molecular weight of 43,952, which is in agreement with the calculated most abundant mass of 43,971 (FIG. 25).

Amino-terminal sequencing. Automated amino acid sequencing was performed using a PROCISE 494 sequenator (Applied Biosystems, Inc., Foster City, Calif.). This revealed that the leader sequences of CC49 scFvSA were cleaved at the expected signal peptidase site adjacent to the first amino acid of the heavy chain variable region.

Figure 26:
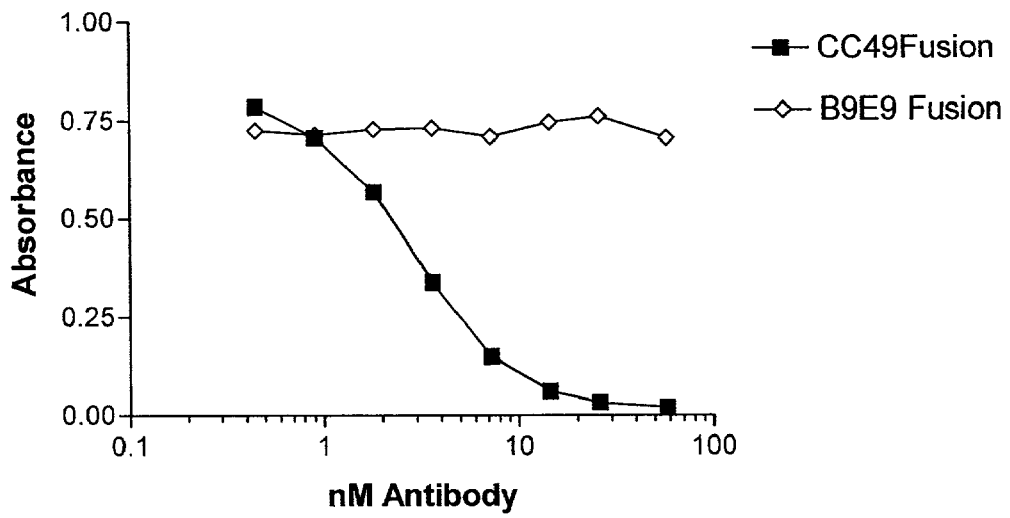
FIG. 26 is a plot illustrating a competitive immunoreactivity assay of CC49 scFvSA and B9E9 scFvSA.

Competitive Immunoreactivity ELISA. Serial dilutions of the anti-TAG-72 CC49 scFvSA or a control anti-CD20 B9E9 scFvSA were allowed to compete with horseradish peroxidase-labeled murine CC49 whole antibody for binding to bovine submaxillary mucin (Sigma Chemical, St. Louis, Mo.), which is a source of TAG-72 antigen. Binding of CC49 scFvSA was specific, and the curve exhibited the sigmoidal shape consistent with a one-site competition model (FIG. 26).

Biotin Binding Capacity. Biotin binding capacity was determined by incubation of a known quantity of fusion protein with a 9-fold molar excess of [$^3$H]biotin (NEN Research Products, Boston, Mass.). After removal of uncomplexed biotin using streptavidin-immobilized beads (Pierce Chemical; Rockford, Ill.), the amount of [$^3$H]biotin associated with the fusion protein was determined.

CC49 scFvSA was capable of binding an average of 3.7 biotins as compared to 4.0 biotin binding sites for recombinant streptavidin.

Figure 27:
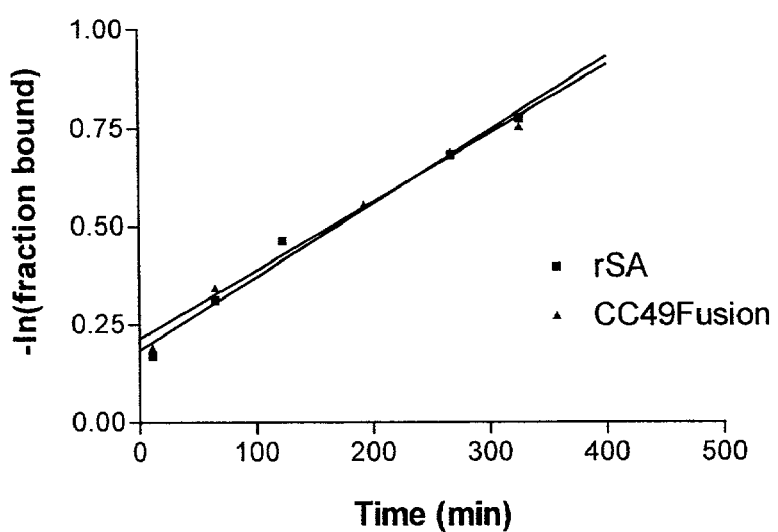
FIG. 27 is a plot illustrating the rate of dissociation of biotin from CC49 scFvSA as compared to recombinant streptavidin (r-SA).

Biotin Dissociation Rate. The rate of biotin dissociation was determined at 37° C. in 0.25 M sodium phosphate, 0.15 M NaCl, 0.25% bovine serum albumin (pH 7.0) containing 10 µM CC49 scFvSA or recombinant streptavidin (control), 0.06 µM [$^3$H] biotin (58 mCi/l mole) and 30 mM ascorbate as [$^3$H] biotin stabilizer. After incubation to reach equilibrium, biocytin (4 mM) was added to initiate irreversible dissociation of [3H] biotin. Aliquots were withdrawn periodically and diluted 20-fold in phosphate-buffered saline containing 0.5% bovine serum albumin. The samples were split for assessment of "total" and "free" [$^3$H] biotin, the latter after protein precipitation using zinc sulfate/NaOH (60 µM each) added sequentially. Radioactivity was assessed in a fluoroscintillate using a Hewlett Packard beta counter. Linear regression analysis of a plot of the ln (fraction bound) versus time yielded a dissociation rate constant. The biotin dissociation rate of CC49 scFvSA was identical to that of recombinant streptavidin (r-SA) ($T_{1/2}$=397 min and 371 min, respectively), indicating fully functional biotin binding (FIG. 27). The above experiments were performed essentially the same as set forth in Example VII, above.

Example XIV

Interaction of CC49 scFvSA with Clearing Agent

To function in the Pretarget® regimen, CC49 scFvSA in circulation must complex efficiently with the synthetic clearing agent (sCA) and be removed rapidly from circulation by subsequent uptake into the liver via the Ashwell receptors. Reactivity of CC49 scFvSA with sCA was assessed in a non-tumored mouse model (n=3/group) where $^{125}$I-CC49 scFvSA (600 µg) was injected i.v. at t=0, followed 18 hours later by a single i.v. bolus injection of approximately a 20-fold stoichiometric excess of sCA.

Figure 28:
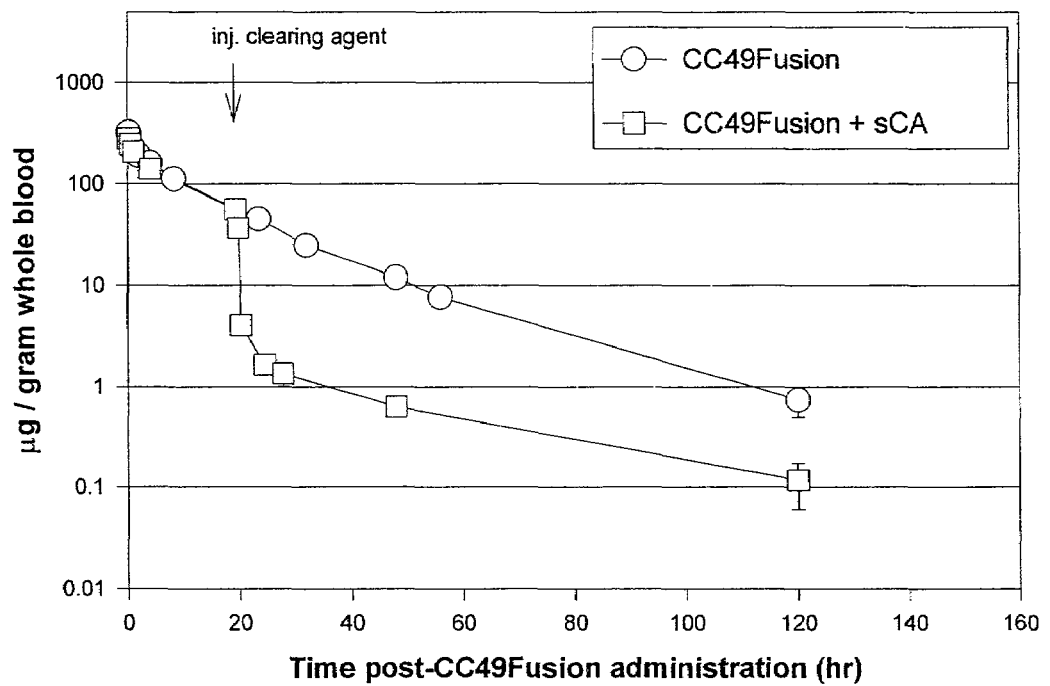
FIG. 28 is a plot demonstrating blood clearance of CC49 scFvSA with and without addition of a clearing agent.

FIG. 28 shows that CC49 scFvSA was rapidly removed from the blood by sCA. The first 2 hours after sCA administration are characterized by a very rapid decline in serum CC49 scFvSA concentration, followed by resumption of its initial, pre-sCA rate. This is consistent with prior results utilizing the sCA with a variety of streptavidin-containing constructs.

Example XV

Biodistribution of $^{111}$In-DOTA-Biotin after Pretargeting with CC49 scFvSA The expressed CC49 scFvSA gene fusion was tested in a full pretarget protocol, essentially as described above in Example VIII except that the tests were performed in female nude mice bearing TAG-72 antigen-positive LS-174T human colon cancer xenografts (100–300 mm³), subcutaneously implanted on the right flank. In these experiments, 600 µg of $^{125}$I-labeled fusion protein was injected intravenous (iv) and allowed to circulate for 20 hours prior to iv injection of 100 µg of synthetic clearing agent (sCA) (See e.g., PCT Publication Nos. WO 97/46098 and WO 95/15978). Four hours after the sCA injection, there was an injection of $^{1.0}$ µg of $^{111}$In-DOTA-biotin, essentially a chelating agent containing a radionuclide, conjugated to biotin (see U.S. Pat. Nos. 5,578,287 and 5,608,060). Mice were sampled for blood, then sacrificed and dissected at 26, 48, 72, and 144 hours after injection of CC49 scFvSA.

Figure 29:
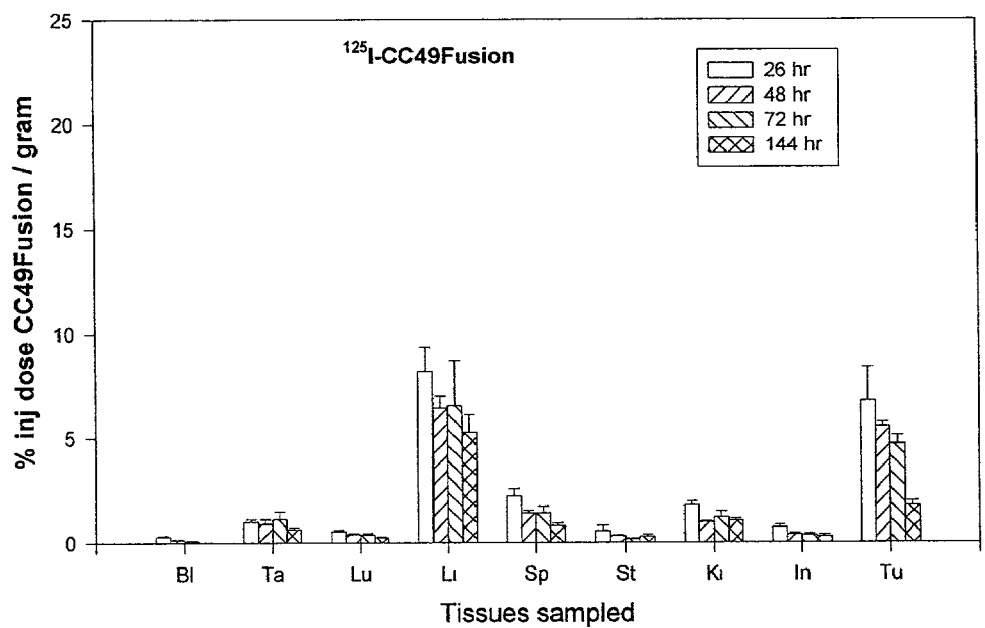
FIG. 29 is a bar graph illustrating biodistribution of radiolabled CC49 scFvSA in a pretargeting regimen. Times are post administration of fusion construct.
Figure 30:
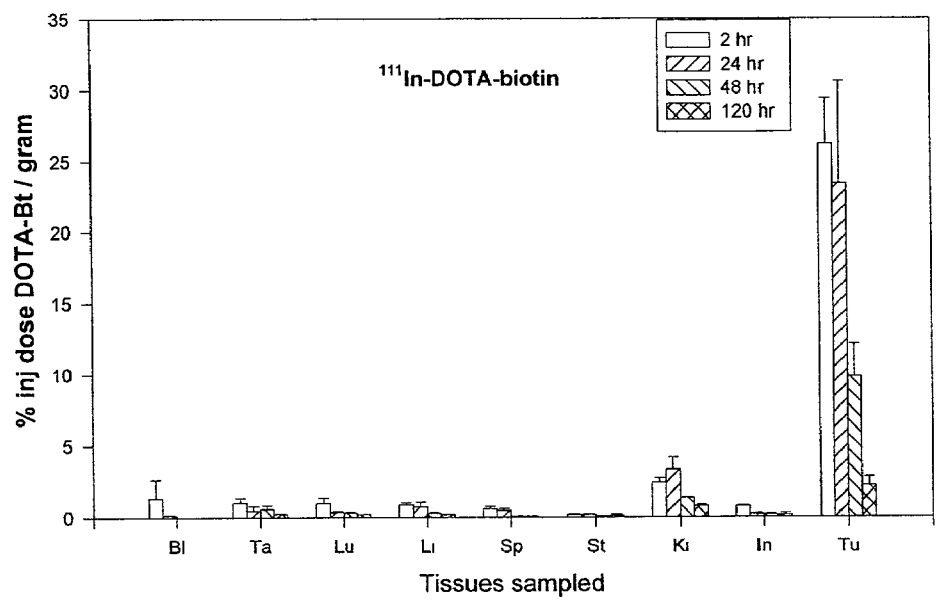
FIG. 30 is a bar graph illustrating biodistribution of pretargeted CC49 scFvSA as measured by radiolabled DOTA-biotin binding. Times are post administration of fusion construct.

The concentration of $^{125}$I-CC49 scFvSA radioactivity in blood and most well-perfused soft tissues is very low, due to the low blood pool concentration induced by the sCA complexation and subsequent hepatic clearance (FIG. 29). (The tissues in order in FIGS. 29 and 30 are blood, tail, lung, liver, spleen, stomach, kidney, intestine, and tumor.) The exceptions were liver and tumor. Liver uptake and retention of fusion protein is due to the mechanism of clearing agent action. The $^{125}$I-CC49 scFvSA exhibits evidence of in vivo immunoreactivity by the retention of relatively high radiolabel concentration at the tumor (both stoichiometrically and relative to blood pool concentration) at all time points.

The concentration of pretargeted $^{111}$In-DOTA-biotin radioactivity in blood and all non-xenograft soft tissues is very low (FIG. 30). Despite the high concentrations of fusion protein in the liver noted above, $^{111}$In-DOTA-biotin uptake and retention in this organ is not in evident, indicating that the fusion protein has been efficiently internalized and is unavailable to bind the subsequently administered radiobiotin. The highest concentration of $^{111}$In-DOTA-biotin is at the tumor at all time points. The rapid uptake, achieving peak concentrations at the earliest time point sampled is a hallmark of pretargeting. Stable delivery and retention of $^{111}$n-DOTA-biotin at the tumor is also observed. Peak concentrations of $^{111}$In-DOTA-biotin at the tumor are 22–28% injected dose/g and occurred within 2 hours post administration of the DOTA-biotin. Tumor-to-blood ratios increased from ca. 40, 2 hours post administration, to >1600 by 24 hours. The area under the curve for blood was 28, while the area under the curve for tumor was 1394, resulting in a high specificity index of 49.

The invention claimed is:

1. A recombinant fusion protein consisting of amino acids 23 to 444 of SEQ ID NO:49.

* * * * *